United States Patent
Heil et al.

(10) Patent No.: US 9,345,247 B2
(45) Date of Patent: May 24, 2016

(54) AZAINDOLE CARBOXYLIC ACID AMIDES AND AZAINDOLE THIOCARBOXYLIC ACID AMIDES FOR USE AS INSECTICIDES AND ACARICIDES

(71) Applicant: BAYER CROPSCIENCE AG, Monheim (DE)

(72) Inventors: Markus Heil, Leichlingen (DE); Roland Andree, Langenfeld (DE); Eike Kevin Heilmann, Duesseldorf (DE); Peter Jeschke, Bergisch Gladbach (DE); Matthias Riedrich, Cologne (DE); Kerstin Iig, Cologne (DE); Ulrich Goergens, Ratingen (DE); Arnd Voerste, Cologne (DE)

(73) Assignee: BAYER CROPSCIENCE AG, Monheim (DE)

( * ) Notice: Subject to any disclaimer, the term of this patent is extended or adjusted under 35 U.S.C. 154(b) by 0 days.

(21) Appl. No.: 14/421,848

(22) PCT Filed: Aug. 13, 2013

(86) PCT No.: PCT/EP2013/066905
§ 371 (c)(1),
(2) Date: Feb. 16, 2015

(87) PCT Pub. No.: WO2014/026984
PCT Pub. Date: Feb. 20, 2014

(65) Prior Publication Data
US 2015/0216175 A1 Aug. 6, 2015

(30) Foreign Application Priority Data
Aug. 17, 2012 (EP) .................... 12180826

(51) Int. Cl.
*C07D 471/04* (2006.01)
*A01N 53/00* (2006.01)
*A01N 43/90* (2006.01)

(52) U.S. Cl.
CPC ............... *A01N 53/00* (2013.01); *A01N 43/90* (2013.01); *C07D 471/04* (2013.01)

(58) Field of Classification Search
CPC ....... C07D 471/04; A01N 53/00; A01N 43/90
USPC .......................................... 514/256; 546/113
See application file for complete search history.

(56) References Cited

U.S. PATENT DOCUMENTS

| 8,710,242 B2 * | 4/2014 | Heil ................. A01N 37/18 |
| | | 548/492 |
| 9,107,411 B2 * | 8/2015 | Heil ................. A01N 43/38 |
| 2011/0105532 A1 | 5/2011 | Heil et al. |
| 2014/0088167 A1 | 3/2014 | Heil et al. |

FOREIGN PATENT DOCUMENTS

| CA | 2 829 822 | 9/2012 |
| EP | 1 479 680 | 11/2004 |
| WO | 2004/104001 | 12/2004 |
| WO | 2007/057329 | 5/2007 |
| WO | 2011/054436 | 5/2011 |
| WO | 2012119984 | 9/2012 |

OTHER PUBLICATIONS

Database Registry, XP-002691245 "1H-Pyrrolo [3,2-B] Pyridine-2,6-Dicarboxylic Acid, 6-Ethyl Ester", Chemical Catalog (2012) p. 1.
Database Registry, XP-002691246 "1H-Pyrrolo [2,3-B] Pyridine-2-Carboxylic Acid, 5-Cyano-", Sinova Inc. (2011) p. 1.
Database Registry, XP-002691247 "1H-Pyrrolo [3,2-B] Pyridine-2-Carboxylic Acid, 6-Cyano", Provence Technologies SAS (2012) p. 1.
Chowdhury et al. Discovery and Optimization of Indoles and 7-Azaindoles as RHO Kinase (Rock) Inhibitors (Part-I), Bioorganic & Medicinal Chemistry Letters, vol. 21 (2011), p. 7107-7112.
European Search Report of EP 12 18 0826 Dated Feb. 1, 2013.
International Search Report of PCT/EP2013/066905 Dated November 27, 2013.

* cited by examiner

*Primary Examiner* — Janet L Andres
*Assistant Examiner* — Daniel Carcanague
(74) *Attorney, Agent, or Firm* — McBee Moore Woodward Vanik IP, LLC

(57) ABSTRACT

The present invention relates to compounds of the general formula (I)

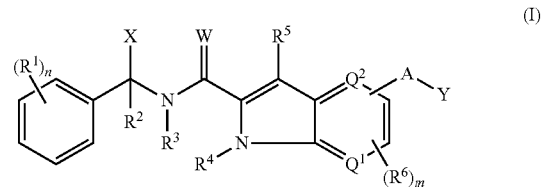

in which R1 to R6, A, Y, X, Q1, Q2, n and m are each as defined in the description—and to a process for their preparation and to their use as insecticides and acaricides.

18 Claims, No Drawings

AZAINDOLE CARBOXYLIC ACID AMIDES AND AZAINDOLE THIOCARBOXYLIC ACID AMIDES FOR USE AS INSECTICIDES AND ACARICIDES

CROSS REFERENCE TO RELATED APPLICATIONS

This application is a §371 National Stage Application of PCT/EP2013/066905, filed Aug. 13, 2013, which claims priority to EP 12180826.5, filed Aug. 17, 2012.

BACKGROUND

1. Field of the Invention

The present invention relates to novel pesticides, to a process for preparation thereof and to the use thereof as active compounds, especially to the use thereof as insecticides and acaricides.

2. Description of Related Art

Insecticidal indolecarboxamides are already known, see WO2011/054436 and WO2012/119984. Also described in the literature are certain azaindolecarboxamides and their use as medicaments, see, for example, Bioorganic & Medicinal Chemistry Letters (2011), 21(23), 7107-7112; WO 2011/050245 or WO 2007/057329. It has now been found that, surprisingly, certain novel azaindolecarboxamides have strong insecticidal and acaricidal properties with simultaneously good plant tolerance, favourable homeotherm toxicity and good environmental compatibility. The novel compounds according to the invention have not been disclosed to date.

SUMMARY

The present invention therefore provides compounds of the general formula (I)

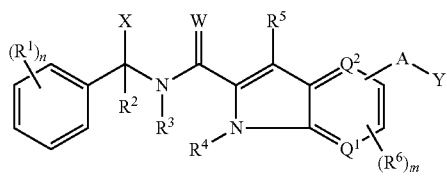

where $R^1$ represents halogen, nitro, cyano, amino, hydroxy, represents $C_1$-$C_6$-alkyl, $C_2$-$C_6$-alkenyl, $C_2$-$C_6$-alkynyl, $C_3$-$C_6$-cycloalkyl, $C_1$-$C_6$-alkoxy, ($C_1$-$C_6$-alkoxy)carbonyl, $C_1$-$C_6$-alkylamino, formyl, ($C_1$-$C_6$-alkyl)carbonyl, $C_1$-$C_6$-alkoxyimino-$C_1$-$C_6$-alkyl, $C_1$-$C_6$-dialkylamino, ($C_1$-$C_6$-alkylamino)carbonyl, ($C_1$-$C_6$-dialkylamino)carbonyl, $C_1$-$C_6$-alkylthio, $C_1$-$C_6$-alkylsulphinyl, $C_1$-$C_6$-alkylsulphonyl, $C_1$-$C_6$-alkylaminosulphonyl, $C_1$-$C_6$-alkylsulphonylamino which are optionally mono- or polysubstituted by identical or different substituents, where the substituents are independently of one another selected from the group consisting of halogen, cyano, nitro, $C_1$-$C_6$-alkyl, $C_1$-$C_6$-alkoxy and $C_1$-$C_6$-haloalkoxy, n represents 1, 2, 3, 4 or 5, or $R^1$ represents —OCF$_2$O—, —(CF$_2$)$_2$O— or —O(CF$_2$)$_2$O— and is attached to two adjacent carbon atoms, in which case n represents 1, $R^2$ represents hydrogen or represents $C_1$-$C_4$-alkyl which is optionally mono- or polysubstituted by identical or different substituents, where the substituents are independently of one another selected from the group consisting of halogen and $C_1$-$C_4$-alkyl, $R^3$ represents hydrogen, represents $C_1$-$C_4$-alkyl, $C_1$-$C_4$-alkylcarbonyl, or $C_1$-$C_4$-alkoxycarbonyl which are optionally mono- or polysubstituted by identical or different substituents, where the substituents are independently of one another selected from the group consisting of cyano, halogen, $C_1$-$C_4$-alkyl and $C_1$-$C_4$-alkoxy, $R^4$ represents $C_1$-$C_6$-alkyl, $C_2$-$C_6$-alkenyl, $C_3$-$C_6$-alkynyl, $C_3$-$C_6$-cycloalkyl, $C_3$-$C_6$-cycloalkyl-$C_1$-$C_4$-alkyl or aryl-$C_1$-$C_4$-alkyl which are optionally mono- or polysubstituted by identical or different substituents, where the substituents are independently of one another selected from the group consisting of halogen, cyano, $C_1$-$C_4$-alkyl and $C_1$-$C_4$-alkoxy, $C_1$-$C_4$-alkoxycarbonyl and from aryloxy and aryl-$C_1$-$C_3$-alkoxy which are optionally mono- or polysubstituted by identical or different substituents, where the substituents are independently of one another selected from the group consisting of halogen, cyano, $C_1$-$C_4$-alkyl, $C_1$-$C_4$-alkoxy, $R^5$ represents hydrogen, $C_1$-$C_4$-alkyl, halogen or cyano, $R^6$ represents hydrogen, halogen, nitro, cyano, amino, hydroxy, represents $C_1$-$C_6$-alkyl, $C_2$-$C_6$-alkenyl, $C_2$-$C_6$-alkynyl, $C_3$-$C_6$-cycloalkyl, $C_1$-$C_6$-alkoxy, ($C_1$-$C_6$-alkoxy)carbonyl, $C_1$-$C_6$-alkylamino, formyl, ($C_1$-$C_6$-alkyl)carbonyl, $C_1$-$C_6$-alkoxyimino-$C_1$-$C_6$-alkyl, $C_1$-$C_6$-dialkylamino, ($C_1$-$C_6$-alkylamino)carbonyl, ($C_1$-$C_6$-dialkylamino)carbonyl, $C_1$-$C_6$-alkylthio, $C_1$-$C_6$-alkylsulphinyl, $C_1$-$C_6$-alkylsulphonyl, $C_1$-$C_6$-alkylaminosulphonyl, $C_1$-$C_6$-alkylsulphonylamino, aryl, hetaryl, aryl-$C_1$-$C_4$-alkyl or hetaryl-$C_1$-$C_4$-alkyl which are optionally mono- or polysubstituted by identical or different substituents, where the substituents are independently of one another selected from the group consisting of halogen, cyano, nitro, hydroxy, amino, $C_1$-$C_6$-alkyl, $C_1$-$C_6$-alkoxy, $C_3$-$C_6$-cycloalkyl, $C_1$-$C_6$-haloalkoxy, $C_1$-$C_6$-alkylthio, aryl, hetaryl, arylalkyl, hetarylalkyl, where the substituents aryl, hetaryl, arylalkyl, hetarylalkyl are optionally mono- or polysubstituted by identical or different substituents from the group consisting of halogen, cyano, nitro, hydroxy, $C_1$-$C_6$-alkyl, $C_2$-$C_6$-alkenyl, $C_2$-$C_6$-alkynyl, $C_3$-$C_6$-cycloalkyl, $C_1$-$C_6$-alkoxy, $C_1$-$C_6$-haloalkyl, $C_1$-$C_6$-haloalkoxy and $C_1$-$C_6$-alkylthio, m represents 0, 1 or 2, X represents $C_1$-$C_6$-haloalkyl which may optionally additionally be mono- to trisubstituted, where the substituents are independently of one another selected from the group consisting of hydroxy, cyano and $C_1$-$C_4$-alkoxy, W represents O or S, A represents a bivalent chemical moiety which is selected from the —C($R^{11}$)($R^{12}$)N$R^{13}$C(=O)—, —C(=O)N$R^{13}$—, —C(=S)N$R^{13}$—, —C($R^{11}$)(U)N$R^{13}$C(=O)—, —C($R^{11}$)($R^{12}$)N(U)C(=O)—, —N($R^{11}$)N$R^{13}$C(=O)— moieties, where the first (left-hand) point of attachment in each case connects to the ring and the second (right-hand) point of attachment in each case connects to Y, and where U represents optionally substituted $C_2$-$C_4$-alkyl which, together with a carbon atom adjacent to the point of attachment of A at the ring forms a 5- to 7-membered ring, where the substituents are independently of one another selected from the group consisting of $C_1$-$C_4$-alkyl and $C_1$-$C_4$-alkoxy, $R^{11}$ and $R^{12}$ are each independently hydrogen or $C_1$-$C_4$-alkyl, $R^{13}$ represents hydrogen, represents $C_1$-$C_4$-alkyl, $C_3$-$C_6$-cycloalkyl, $C_1$-$C_4$-alkylcarbonyl, $C_1$-$C_4$-alkoxycarbonyl or $C_1$-$C_4$-alkenyl, Y represents $C_1$-$C_6$-alkyl, $C_2$-$C_6$-alkenyl, $C_2$-$C_6$-alkynyl, $C_3$-$C_6$-cycloalkyl, heterocyclyl, oxidoheterocyclyl, dioxido-heterocyclyl, aryl, aryl-$C_1$-$C_4$-alkyl, hetaryl or hetaryl-$C_1$-$C_4$-alkyl which are optionally mono- or polysubstituted by identical or different substituents, where the substituents are selected from the group consisting of halogen, nitro, cyano, hydroxy, aminothiocarbonyl, aminocarbonyl, $C_1$-$C_4$-alkylaminocarbonyl, $C_1$-$C_4$-haloalkylaminocarbonyl, di($C_1$-$C_4$-alkyl)aminocarbonyl, hydroxycarbonyl, $C_1$-$C_4$-alkyl, $C_1$-$C_4$-haloalkyl, $C_3$-$C_6$-cycloalkyl, $C_1$-$C_4$-alkyl-$C_3$-$C_4$-cycloalkyl, $C_2$-$C_6$-alkenyl, $C_2$-$C_6$-alkynyl, $C_1$-$C_6$-alkoxy, $C_1$-$C_6$-alkoxycarbonyl, $C_1$-$C_6$-alkylcarbonyl, $C_1$-$C_4$-alkoxyimino-$C_1$-$C_4$-alkyl, $C_1$-$C_6$-alkylthio, $C_1$-$C_6$-alkylsulphinyl and $C_1$-$C_6$-alkylsulphonyl, $Q^1$ represents N, where simultaneously $Q^2$ represents a carbon atom which is substituted by hydrogen, $R^6$ or A-Y, or $Q^1$ represents a carbon atom which is substituted by hydrogen, $R^6$ or A-Y and $Q^2$ simultaneously represents N, and salts and N-oxides of compounds of the formula (I), and the use thereof for controlling animal pests.

If appropriate, the compounds of the formula (I) may be present in various polymorphic forms or as a mixture of various polymorphic forms. Both the pure polymorphs and the polymorph mixtures form part of the subject-matter of the invention and can be used in accordance with the invention.

The compounds of the formula (I) include any E/Z isomers and diastereomers or enantiomers which exist.

The substituted indole- and benzimidazolecarboxamides are defined in general terms by the formula (I). Preferred radical definitions for the formulae specified above and hereinafter are given below. These definitions apply to the end products of the formula (I) and likewise to all intermediates.

The particular number of substituents n and m in the formula (I) includes only the substituents other than hydrogen. For this reason, hydrogen is also not included in the definition of $R^1$ and $R^6$. Of course, hydrogen is always present as a substituent when no $R^1$ or $R^6$ substituent is present at the particular site.

Preference, particular preference and very particular preference is given to compounds of the formula (I), and to a method for controlling pests using the compounds of the formula (I), where $R^1$ preferably represents halogen, nitro, cyano, represents $C_1$-$C_4$-alkyl, $C_1$-$C_4$-alkoxy, $C_1$-$C_4$-alkylthio, $C_1$-$C_4$-alkylsulphinyl or $C_1$-$C_4$-alkylsulphonyl which are optionally mono- or polysubstituted by halogen, n preferably represents 1, 2, 3, 4 or 5 or $R^1$ represents —$OCF_2O$— or —$O(CF_2)_2O$— and is attached to two adjacent carbon atoms, in which case n represents 1, $R^2$ preferably represents hydrogen or represents $C_1$-$C_4$-alkyl which is optionally mono- to trisubstituted, where the substituents are each independently selected from the group consisting of halogen and $C_1$-$C_4$-alkyl, $R^3$ preferably represents hydrogen, represents $C_1$-$C_4$-alkyl, $C_1$-$C_4$-alkylcarbonyl or $C_1$-$C_4$-alkoxycarbonyl which are optionally mono- or polysubstituted by identical or different substituents, where the substituents are independently of one another selected from the group consisting of cyano, halogen and $C_1$-$C_4$-alkoxy, $R^4$ preferably represents $C_1$-$C_4$-alkyl, $C_2$-$C_6$-alkenyl, $C_3$-$C_6$-alkynyl, $C_3$-$C_6$-cycloalkyl, $C_3$-$C_6$-cycloalkyl-$C_1$-$C_3$-alkyl or aryl-$C_1$-$C_4$-alkyl which are optionally mono- or polysubstituted by identical or different substituents, where the substituents are independently of one another selected from the group consisting of halogen, cyano, $C_1$-$C_4$-alkyl, $C_1$-$C_4$-alkoxy, $C_1$-$C_4$-alkoxycarbonyl or from aryloxy and aryl-$C_1$-$C_3$-alkoxy which are optionally mono- or polysubstituted by identical or different substituents, where the substituents are independently of one another selected from the group consisting of halogen, cyano, $C_1$-$C_4$-alkyl, $C_1$-$C_4$-alkoxy, $R^5$ preferably represents hydrogen, $C_1$-$C_4$-alkyl, halogen or cyano, $R^6$ preferably represents hydrogen, halogen, nitro, cyano, represents $C_1$-$C_4$-alkyl, $C_2$-$C_4$-alkenyl, $C_2$-$C_4$-alkynyl, $C_1$-$C_4$-alkoxy, ($C_1$-$C_4$-alkyl)carbonyl, ($C_1$-$C_4$-alkylamino)carbonyl, ($C_1$-$C_4$-dialkylamino)carbonyl, $C_1$-$C_4$-alkylthio, $C_1$-$C_4$-alkylsulphinyl, $C_1$-$C_4$-alkylsulphonyl, $C_1$-$C_4$-alkylaminosulphonyl or $C_1$-$C_4$-alkylsulphonylamino which are optionally mono- or polysubstituted by identical or different substituents, where the substituents are independently of one another selected from the group consisting of halogen, cyano, nitro, $C_1$-$C_6$-alkyl, $C_1$-$C_6$-alkoxy, $C_1$-$C_6$-haloalkoxy and $C_1$-$C_6$-alkylthio, m preferably represents 0, 1 or 2, X preferably represents $C_1$-$C_4$-haloalkyl which may optionally additionally be mono- to trisubstituted by hydroxy, cyano or $C_1$-$C_4$-alkoxy, W preferably represents O, A preferably represents a bivalent chemical moiety which is selected from the —$C(R^{11})(R^{12})NR^{13}C(=O)$— and —$C(=O)NR^{13}$— moieties, where the first (left-hand) point of attachment in each case connects to the ring and the second (right-hand) point of attachment in each case connects to Y, $R^{11}$ and $R^{12}$ independently of one another preferably represent hydrogen or represent $C_1$-$C_4$-alkyl, $R^{13}$ preferably represents hydrogen, represents $C_1$-$C_4$-alkyl, $C_3$-$C_6$-cycloalkyl, $C_1$-$C_4$-alkylcarbonyl, $C_1$-$C_4$-alkoxycarbonyl or $C_2$-$C_4$-alkenyl, Y preferably represents $C_1$-$C_4$-alkyl, $C_2$-$C_4$-alkenyl, $C_2$-$C_4$-alkynyl, $C_3$-$C_6$-cycloalkyl, phenyl, phenylmethyl, oxetanyl, thietanyl, oxidothietanyl, dioxidothietanyl, pyridinyl, pyridinylmethyl, pyrimidinyl or pyrimidinylmethyl which are optionally mono- or polysubstituted by identical or different substituents, where the substituents are selected from the group consisting of halogen, nitro, cyano, hydroxyl, aminothiocarbonyl, aminocarbonyl, $C_1$-$C_4$-alkyl, $C_1$-$C_4$-haloalkyl, $C_3$-$C_5$-cycloalkyl, $C_1$-$C_4$-alkyl-$C_3$-$C_4$-cycloalkyl, $C_2$-$C_4$-alkenyl, $C_2$-$C_4$-alkynyl, $C_1$-$C_4$-alkoxy, $C_1$-$C_4$-alkylthio, $C_1$-$C_4$-alkylsulphinyl, $C_1$-$C_4$-alkylsulphonyl, $C_1$-$C_4$-alkoxycarbonyl, $C_1$-$C_6$-alkylcarbonyl and $C_1$-$C_4$-alkoxyimino-$C_1$-$C_4$-alkyl, $Q^1$ preferably represents N, where simultaneously $Q^2$ represents a carbon atom which is substituted by hydrogen, $R^6$ or A-Y, or $Q^1$ preferably represents a carbon atom which is substituted by hydrogen, $R^6$ or A-Y and $Q^2$ simultaneously represents N, $R^1$ particularly preferably represents halogen, nitro, cyano, represents $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl which are optionally mono- or polysubstituted by fluorine or chlorine, n particularly preferably represents 1, 2, 3, 4 or 5 or $R^1$ represents —$OCF_2O$— and is attached to two adjacent carbon atoms, in which case n represents 1, $R^2$ particularly preferably represents hydrogen or represents methyl, $R^3$ particularly preferably represents hydrogen, methyl, ethyl, methylcarbonyl, ethylcarbonyl, methoxycarbonyl or ethoxycarbonyl, $R^4$ particularly preferably represents $C_1$-$C_4$-alkyl, $C_2$-$C_4$-alkenyl, $C_3$-$C_4$-alkynyl, $C_3$-$C_5$-cycloalkyl, $C_3$-$C_5$-cycloalkyl-$C_1$-$C_3$-alkyl or phenyl-$C_1$-$C_4$-alkyl which are optionally mono- to trisubstituted, where the substituents are independently of one another selected from the group consisting of fluorine, cyano, methoxy, ethoxy, methyl, ethyl, methoxycarbonyl, ethoxycarbonyl, phenyloxy and phenyl-$C_1$-$C_3$-alkoxy, $R^5$ particularly preferably represents hydrogen, methyl, ethyl, fluorine, chlorine, bromine or cyano, $R^6$ particularly preferably represents halogen, nitro, cyano, or represents $C_1$-$C_4$-alkyl or $C_1$-$C_4$-alkoxy which are optionally mono- to trisubstituted by halogen, m particularly preferably represents 0, 1 or 2, X particularly preferably represents $C_1$-$C_4$-haloalkyl, W particularly preferably represents O, A particularly preferably represents a bivalent chemical moiety which is selected from the —$C(R^{11})(R^{12})NR^{13}C(=O)$— and —$C(=O)NR^{13}$— moieties, where the first (left-hand) point of attachment in each case connects to the ring and the second (right-hand) point of attachment in each case connects to Y, and where $R^{11}$ and $R^{12}$ particularly preferably represent hydrogen, and where $R^{13}$ particularly preferably represents hydrogen, methyl, ethyl, cyclopropyl, methylcarbonyl, ethylcarbonyl, methoxycarbonyl, ethoxycarbonyl or prop-2-en-1-yl, Y particularly preferably represents $C_1$-$C_4$-alkyl, $C_2$-$C_4$-alkenyl, $C_2$-$C_4$-alkynyl, $C_3$-$C_6$-cycloalkyl, phenyl, phenylmethyl, 3-oxetan-1-yl, pyridin-2-yl, pyridin-2-ylmethyl, 1,3-pyrimidin-2-yl or 1,3-pyrimidin-2-ylmethyl which are optionally mono- to trisubstituted by identical or different substituents, where the substituents are selected from the group consisting of fluorine, chlorine, nitro, cyano, $C_1$-$C_4$-alkyl, trifluoromethyl, $C_3$-$C_4$-cycloalkyl, $C_1$-$C_4$-alkyl-$C_3$-$C_4$-cycloalkyl, $C_2$-$C_4$-alkenyl, $C_3$-$C_4$-alkynyl $C_1$-$C_4$-alkoxy, $C_1$-$C_4$-alkylthio, $C_1$-$C_4$-alkylsulphinyl, $C_1$-$C_4$-alkylsulphonyl, $C_1$-$C_4$-alkoxycarbonyl and aminothiocarbonyl, $Q^1$ particularly preferably represents N, where simultaneously $Q^2$ represents a carbon atom which is substituted by hydrogen, or $Q^1$ particularly preferably represents a carbon atom which is substituted by hydrogen and $Q^2$ simultaneously represents N, $R^1$ very particularly preferably represents cyano, fluorine, chlorine, bromine, iodine, methyl, ethyl, 2-methylethyl, difluoromethyl, dichlorofluoromethyl, chlorodifluoromethyl, trifluoromethyl, pentafluoroethyl, chlorotetrafluoroethyl, methoxy, difluoromethoxy, trifluoromethoxy, methylthio, trifluoromethylthio, trifluoromethylsulphinyl, trifluoromethylsulphonyl, n very particularly preferably represents 1, 2, 3, 4 or 5, $R^2$ very particularly preferably represents hydrogen, $R^3$ very particularly preferably represents hydrogen or methyl, $R^4$ very particularly preferably represents methyl, ethyl, prop-1-yl, prop-2-en-1-yl, propyn-3-yl, ethenyl, but-2-yn-1-yl, cyclopropyl, cyclopropylmethyl, cyclobutyl, $R^5$ very particularly preferably represents hydrogen or bromine, $R^6$ very particularly preferably represents cyano, fluorine, chlorine, bromine, iodine, methyl, ethyl or trifluoromethyl, m very particularly preferably represents 0 or 1, X very particularly preferably represents trifluoromethyl, W very particularly preferably represents O, A very particularly preferably represents the bivalent chemical moieties —$C(=O)NR^{13}$— or —$CH_2$—NH—C(=O)$$—, where the first (left-hand) point of attachment connects to the ring and the second (right-hand) point of attachment connects to Y, and where $R^{13}$ very particularly preferably represents hydrogen, methyl or ethyl, Y very particularly preferably represents methyl, ethyl, propan-1-yl, propan-2-yl, propyn-3-yl, butan-1-yl, butan-2-yl, 2-methylpropan-1-yl, 2-methylpropan-2-yl, cyclopropyl, cyclobutyl, cyanomethyl, 1-methoxycarbonylmethyl, 1-cyanoethyl, 2-cyanoethyl, 1-cyanoprop-1-yl, 2-cyanoprop-1-yl, 3-cyanoprop-1-yl, 1-cyanoprop-2-yl, 2-cyanoprop-2-yl, 1-cyanocyclopropyl, 2-cyanoprop-2-en-1-yl, 2-cyanocyclopropyl, 1-cyanocyclobutyl, 2-cyanocyclobutyl, 3-cyanocyclobutyl, 2-fluoroethyl, 2,2-difluoroethyl, 2,2,2-trifluoroethyl, 1-fluoropropan-2-yl, 2,2-difluoroprop-1-yl, 1,3-difluoropropan-2-yl, 1-methylcyclopropyl, 2-methylcyclopropyl, 1-ethylcyclopropyl, 1-ethynylcyclopropyl, 1-ethynylcyclobutyl, 1-methoxycyclopropyl, 1-ethoxycyclopropyl, 1-methoxycarbonylcyclopropyl, 1-ethoxycarbonylcyclopropyl, cyclopropylmethyl, 1-cyclopropyleth-1-yl, 1-trifluoromethylcyclopropyl, pyridin-2-yl, 5-chloropyridin-2-yl, 5-fluoropyridin-2-yl, 1-(aminothiocarbonyl)cyclopropyl, 1-cyano-2-methylpropan-1-yl, 1-cyanobut-3-yn-1-yl, 1-cyano-2-methylpropan-1-yl, 1-cyanopropan-2-yl, 1-cyano-1-cyclopropylethyl, 1-cyano-1-ethylprop-1-yl, 1-cyano-1-methylcyclopropylmethyl, (2-R)-1-(methylthio)propan-2-yl, (2-R)-1-(methylsulphinyl)propan-2-yl or 1,3-dimethoxy-2-cyanopropan-2-yl, 3-oxetan-1-yl, pyridin-2-ylmethyl, 1,3-pyrimidin-2-yl-methyl when A represents the $C(=O)NR^{13}$— moiety, or Y very particularly preferably represents methyl, ethyl, propan-1-yl, propan-2-yl, butan-1-yl, 2-fluoroethyl, 2,2-difluoroethyl, 2,2,2-trifluoroethyl, cyclopropyl, cyclobutyl or cyclopropylmethyl when A represents the —$CH_2NHC(=O)$— moiety, $Q^1$ very particularly preferably represents N, where simultaneously $Q^2$ represents a carbon atom which is substituted by hydrogen.

DETAILED DESCRIPTION OF A PREFERRED EMBODIMENT

The above-specified individual general, preferred, more preferred and most preferred definitions for the substituents $R^1$ to $R^6$, n, m, X, W, A, Y, $Q^1$ and $Q^2$ can be combined with one another as desired in accordance with the invention.

In the preferred definitions, unless stated otherwise, halogen is selected from the group of fluorine, chlorine, bromine and iodine, preferably in turn from the group of fluorine, chlorine and bromine.

In the more preferred definitions, unless stated otherwise, halogen is selected from the group of fluorine, chlorine, bromine and iodine, preferably in turn from the group of fluorine, chlorine and bromine.

In the most preferred definitions, unless stated otherwise, halogen is selected from the group of fluorine, chlorine, bromine and iodine, preferably in turn from the group of fluorine, chlorine and bromine.

Halogen-substituted radicals, for example haloalkyl, are mono- or polyhalogenated up to the maximum possible number of substituents. In the case of polyhalogenation, the halogen atoms can be identical or different. In this case, halogen is fluorine, chlorine, bromine or iodine, especially fluorine, chlorine or bromine.

Preference, particular preference and very particular preference is given to compounds which bear the substituents specified under preferred, particularly preferred and very particularly preferred, respectively.

Saturated or unsaturated hydrocarbyl radicals such as alkyl, alkenyl or alkynyl may each be straight-chain or branched to the extent possible, including in combination with heteroatoms, as, for example, in alkoxy.

Unless defined differently elsewhere, aryl denotes a mono-, bi- or tricyclic ring system group where at least one cycle is aromatic, preferably having $(C_6-C_{14})$-, $(C_6-C_8)$- or $(C_6)$-ring atoms. Aryl preferably represents phenyl.

Unless defined differently elsewhere, hetaryl denotes a mono-, bi- or tricyclic heterocyclic group of carbon atoms and at least one heteroatom, where at least one cycle is aromatic. Preferably, the hetaryl group contains 3, 4, 5 or 6 carbon atoms. Hetaryl preferably represents pyridinyl or pyrimidinyl.

Unless defined differently elsewhere, heterocyclyl denotes a monocyclic saturated or partially saturated 4-, 5-, 6- or 7-membered ring of carbon atoms and at least one heteroatom in the ring. Preferably, the heterocyclyl group contains 3, 4, 5 or 6 carbon atoms and 1 or 2 heteroatoms from the group consisting of oxygen, sulphur and nitrogen. Unless defined differently elsewhere, oxidoheterocyclyl and dioxidoheterocyclyl denote heterocyclyl which contains in at least one position in the ring a ring atom which is substituted by one and two (=O) groups, respectively. Here, preferably a heteroatom such as sulphur is substituted by one or two (=O) groups resulting in the groups S(=O)— and —S(=O)$_2$—, respectively, where the sulphur atom is a constituent of the ring.

Optionally substituted radicals may be mono- or polysubstituted, where the substituents in the case of polysubstitution may be the same or different.

The radical definitions or elucidations given above in general terms or within areas of preference apply to the end products and correspondingly to the starting materials and intermediates. These radical definitions can be combined with one another as desired, i.e. including combinations between the respective preferred ranges.

Preference is given in accordance with the invention to compounds of the formula (I) in which a combination of the definitions listed above as preferred is present.

Particular preference is given in accordance with the invention to compounds of the formula (I) in which a combination of the definitions listed above as particularly preferred is present.

In a preferred embodiment, the invention relates to the compounds of the formula (I-1)

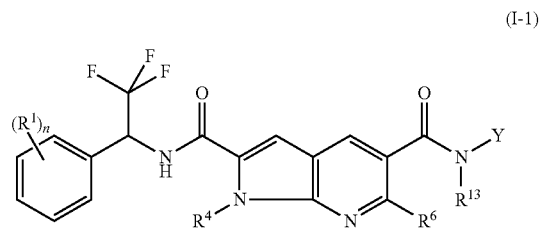

(I-1)

where $R^1$, $R^4$, $R^6$, $R^{13}$, Y and n each have the meanings described above.

In a further preferred embodiment, the invention relates to the compounds of the formula (I-2)

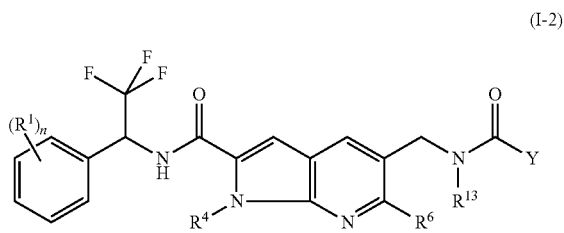

(I-2)

where $R^1$, $R^4$, $R^6$, $R^{13}$, Y and n each have the meanings described above.

In a further preferred embodiment, the invention relates to the compounds of the formula (I-3)

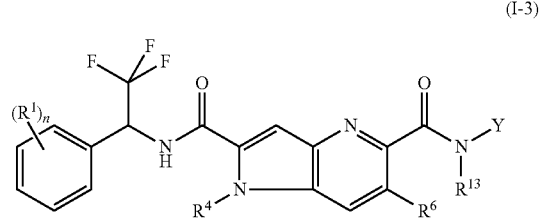

(I-3)

where $R^1$, $R^4$, $R^6$, $R^{13}$, Y and n each have the meanings described above.

In a further preferred embodiment, the invention relates to the compounds of the formula (I-4)

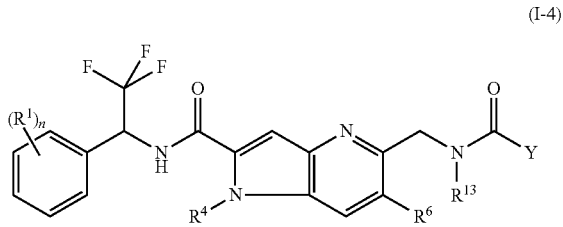

(I-4)

where $R^1$, $R^4$, $R^6$, $R^{13}$, Y and n each have the meanings described above.

Preferred compounds according to the invention also include the compounds of the general formula (I-5) shown in Table 1 and the compounds shown in Table 2.

The present compounds of the general formula (I) may optionally have a chiral carbon atom.

According to the rules of Cahn, Ingold and Prelog (CIP rules), these substituents may have either an (R) configuration or an (S) configuration.

The present invention encompasses compounds of the general formula (I) both with (S) and with (R) configuration at the particular chiral carbon atoms, i.e. the present invention encompasses the compounds of the general formula (I) in which the carbon atoms in question each independently have
(1) an (R) configuration; or
(2) an (S) configuration.

When more than one chiral centre is present in the compounds of the general formula (I), any desired combinations of the configurations of the chiral centres are possible, which means that
(1) one chiral centre may have the (R) configuration and the other chiral centre the (S) configuration;
(2) one chiral centre may have the (R) configuration and the other chiral centre the (R) configuration; and
(3) one chiral centre may have the (S) configuration and the other chiral centre the (S) configuration.

The compounds of the formula (I) likewise encompass any diastereomers or enantiomers and E/Z isomers which exist, and also salts and N-oxides of compounds of the formula (I), and the use thereof for control of animal pests.

The invention also relates to the use of the compounds of the general formula (I) according to the invention for production of pesticides.

The invention also relates to pesticides comprising compounds of the general formula (I) according to the invention and/or salts thereof in biologically effective contents of >0.00000001% by weight, preferably >0.001% by weight to 95% by weight, based on the weight of the pesticide.

The invention also relates to methods for controlling animal pests, in which compounds of the general formula (I) according to the invention are allowed to act on animal pests and/or their habitat. The control of the animal pests is preferably conducted in agriculture and forestry, and in material protection. Preferably excluded is the treatment, more particularly the therapeutic treatment, of the human or animal body.

The active compounds or active compound combinations according to the invention, in combination with good plant tolerance and favourable toxicity to warm-blooded animals and being tolerated well by the environment, are suitable for protecting plants and plant organs, for increasing the harvest yields, for improving the quality of the harvested material and for controlling animal pests, in particular insects, arachnids, helminths, nematodes and molluscs, which are encountered in agriculture, in horticulture, in animal husbandry, in forests, in gardens and leisure facilities, in the protection of stored products and of materials, and in the hygiene sector. They can preferably be used as crop protection agents. They are effective against normally sensitive and resistant species and against all or some stages of development. The abovementioned pests include:

pests from the phylum of the Arthropoda, more particularly from the class of the Arachnida, for example *Acarus* spp., *Aceria sheldoni*, *Aculops* spp., *Aculus* spp., *Amblyomma* spp., *Amphitetranychus viennensis*, *Argas* spp., *Boophilus* spp., *Brevipalpus* spp., *Bryobia graminum*, *Bryobia praetiosa*, *Centruroides* spp., *Chorioptes* spp., *Dermanyssus gallinae*, *Dermatophagoides pteronyssinus*, *Dermatophagoides farinae*, *Dermacentor* spp., *Eotetranychus* spp., *Epitrimerus pyri*, *Eutetranychus* spp., *Eriophyes* spp., *Glycyphagus domesticus*, *Halotydeus destructor*, *Hemitarsonemus* spp., *Hyalomma* spp., *Ixodes* spp., *Latrodectus* spp., *Loxosceles* spp., *Metatetranychus* spp., *Neutrombicula autumnalis*, *Nuphersa* spp., *Oligonychus* spp., *Ornithodorus* spp., *Ornithonyssus* spp., *Panonychus* spp., *Phyllocoptruta oleivora*, *Polyphagotarsonemus latus*, *Psoroptes* spp., *Rhipicephalus* spp., *Rhizoglyphus* spp., *Sarcoptes* spp., *Scorpio maurus*, *Steneotarsonemus* spp., *Steneotarsonemus spinki*, *Tarsonemus* spp., *Tetranychus* spp., *Trombicula alfreddugesi*, *Vaejovis* spp., *Vasates lycopersici.*;

from the class of the Chilopoda, for example *Geophilus* spp., *Scutigera* spp.;

from the order or the class of the Collembola, for example *Onychiurus armatus.*;

from the class of the Diplopoda, for example *Blaniulus guttulatus;* from the class of the Insecta, for example from the order of the Blattodea, for example *Blattella asahinai*, *Blattella germanica*, *Blatta orientalis*, *Leucophaea maderae*, *Panchlora* spp., *Parcoblatta* spp., *Periplaneta* spp., *Supella longipalpa;* from the order of the Coleoptera, for example *Acalymma vittatum*, *Acanthoscelides obtectus*, *Adoretus* spp., *Agelastica alni*, *Agriotes* spp., *Alphitobius diaperinus*, *Amphimallon solstitialis*, *Anobium punctatum*, *Anoplophora* spp., *Anthonomus* spp., *Anthrenus* spp., *Apion* spp., *Apogonia* spp., *Atomaria* spp., *Attagenus* spp., *Bruchidius obtectus*, *Bruchus* spp., *Cassida* spp., *Cerotoma trifurcata*, *Ceutorrhynchus* spp., *Chaetocnema* spp., *Cleonus mendicus*, *Conoderus* spp., *Cosmopolites* spp., *Costelytra zealandica*, *Ctenicera* spp., *Curculio* spp., *Cryptolestes ferrugineus*, *Cryptorhynchus lapathi*, *Cylindrocopturus* spp., *Dermestes* spp., *Diabrotica* spp., *Dichocrocis* spp., *Dicladispa armigera*, *Diloboderus* spp., *Epilachna* spp., *Epitrix* spp., *Faustinus* spp., *Gibbium psylloides*, *Gnathocerus cornutus*, *Hellula undalis*, *Heteronychus arator*, *Heteronyx* spp., *Hylamorpha elegans*, *Hylotrupes bajulus*, *Hypera postica*, *Hypomeces squamosus*, *Hypothenemus* spp., *Lachnosterna consanguinea*, *Lasioderma serricorne*, *Latheticus oryzae*, *Lathridius* spp., *Lema* spp., *Leptinotarsa decemlineata*, *Leucoptera* spp., *Lissorhoptrus oryzophilus*, *Lixus* spp., *Luperodes* spp., *Lyctus* spp., *Megascelis* spp., *Melanotus* spp., *Meligethes aeneus*, *Melolontha* spp., *Migdolus* spp., *Monochamus* spp., *Naupactus xanthographus*, *Necrobia* spp., *Niptus hololeucus*, *Oryctes rhinoceros*, *Oryzaephilus surinamensis*, *Oryzaphagus oryzae*, *Otiorrhynchus* spp., *Oxycetonia jucunda*, *Phaedon cochleariae*, *Phyllophaga* spp., *Phyllophaga helleri*, *Phyllotreta* spp., *Popillia japonica*, *Premnotrypes* spp., *Prostephanus truncatus*, *Psylliodes* spp., *Ptinus* spp., *Rhizobius ventralis*, *Rhizopertha dominica*, *Sitophilus* spp., *Sitophilus oryzae*, *Sphenophorus* spp., *Stegobium paniceum*, *Sternechus* spp., *Symphyletes* spp., *Tanymecus* spp., *Tenebrio molitor*, *Tene-

*brioides mauretanicus*, *Tribolium* spp., *Trogoderma* spp., *Tychius* spp., *Xylotrechus* spp., *Zabrus* spp.;

from the order of the Diptera, for example *Aedes* spp., *Agromyza* spp., *Anastrepha* spp., *Anopheles* spp., *Asphondylia* spp., *Bactrocera* spp., *Bibio hortulanus*, *Calliphora erythrocephala*, *Calliphora vicina*, *Ceratitis capitata*, *Chironomus* spp., *Chrysomyia* spp., *Chrysops* spp., *Chrysozona pluvialis*, *Cochliomyia* spp., *Contarinia* spp., *Cordylobia anthropophaga*, *Cricotopus sylvestris*, *Culex* spp., *Culicoides* spp., *Culiseta* spp., *Cuterebra* spp., *Dacus oleae*, *Dasyneura* spp., *Delia* spp., *Dermatobia hominis*, *Drosophila* spp., *Echinocnemus* spp., *Fannia* spp., *Gasterophilus* spp., *Glossina* spp., *Haematopota* spp., *Hydrellia* spp., *Hydrellia griseola*, *Hylemya* spp., *Hippobosca* spp., *Hypoderma* spp., *Liriomyza* spp., *Lucilia* spp., *Lutzomyia* spp., *Mansonia* spp., *Musca* spp., *Oestrus* spp., *Oscinella frit*, *Paratanytarsus* spp., *Paralauterborniella subcincta*, *Pegomyia* spp., *Phlebotomus* spp., *Phorbia* spp., *Phormia* spp., *Piophila casei*, *Prodiplosis* spp., *Psila rosae*, *Rhagoletis* spp., *Sarcophaga* spp., *Simulium* spp., *Stomoxys* spp., *Tabanus* spp., *Tetanops* spp., *Tipula* spp.;

from the order of the Heteroptera, for example *Anasa tristis*, *Antestiopsis* spp., *Boisea* spp., *Blissus* spp., *Calocoris* spp., *Campylomma livida*, *Cavelerius* spp., *Cimex* spp., *Collaria* spp., *Creontiades dilutus*, *Dasynus piperis*, *Dichelops furcatus*, *Diconocoris hewetti*, *Dysdercus* spp., *Euschistus* spp., *Eurygaster* spp., *Heliopeltis* spp., *Horcias nobilellus*, *Leptocorisa* spp., *Leptocorisa varicornis*, *Leptoglossus phyllopus*, *Lygus* spp., *Macropes excavatus*, *Miridae*, *Monalonion atratum*, *Nezara* spp., *Oebalus* spp., *Pentomidae*, *Piesma quadrata*, *Piezodorus* spp., *Psallus* spp., *Pseudacysta persea*, *Rhodnius* spp., *Sahlbergella singularis*, *Scaptocoris castanea*, *Scotinophora* spp., *Stephanitis nashi*, *Tibraca* spp., *Triatoma* spp.;

from the order of the Homoptera, for example *Acizzia acaciaebaileyanae*, *Acizzia dodonaeae*, *Acizzia uncatoides*, *Acrida turrita*, *Acyrthosipon* spp., *Acrogonia* spp., *Aeneolamia* spp., *Agonoscena* spp., *Aleyrodes proletella*, *Aleurolobus barodensis*, *Aleurothrixus floccosus*, *Allocaridara malayensis*, *Amrasca* spp., *Anuraphis cardui*, *Aonidiella* spp., *Aphanostigma pini*, *Aphis* spp., *Arboridia apicalis*, *Arytainilla* spp., *Aspidiella* spp., *Aspidiotus* spp., *Atanus* spp., *Aulacorthum solani*, *Bemisia tabaci*, *Blastopsylla occidentalis*, *Boreioglycaspis melaleucae*, *Brachycaudus helichrysi*, *Brachycolus* spp., *Brevicoryne brassicae*, *Cacopsylla* spp., *Calligypona marginata*, *Carneocephala fulgida*, *Ceratovacuna lanigera*, *Cercopidae*, *Ceroplastes* spp., *Chaetosiphon fragaefolii*, *Chionaspis tegalensis*, *Chlorita onukii*, *Chondracris rosea*, *Chromaphis juglandicola*, *Chrysomphalus ficus*, *Cicadulina mbila*, *Coccomytilus halli*, *Coccus* spp., *Cryptomyzus ribis*, *Cryptoneossa* spp., *Ctenarytaina* spp., *Dalbulus* spp., *Dialeurodes citri*, *Diaphorina citri*, *Diaspis* spp., *Drosicha* spp., *Dysaphis* spp., *Dysmicoccus* spp., *Empoasca* spp., *Eriosoma* spp., *Erythroneura* spp., *Eucalyptolyma* spp., *Euphyllura* spp., *Euscelis bilobatus*, *Ferrisia* spp., *Geococcus coffeae*, *Glycaspis* spp., *Heteropsylla cubana*, *Heteropsylla spinulosa*, *Homalodisca coagulata*, *Hyalopterus arundinis*, *Icerya* spp., *Idiocerus* spp., *Idioscopus* spp., *Laodelphax striatellus*, *Lecanium* spp., *Lepidosaphes* spp., *Lipaphis erysimi*, *Macrosiphum* spp., *Macrosteles facifrons*, *Mahanarva* spp., *Melanaphis sacchari*, *Metcalfiella* spp., *Metopolophium dirhodum*, *Monellia costalis*, *Monelliopsis pecanis*, *Myzus* spp., *Nasonovia ribisnigri*, *Nephotettix* spp., *Nettigoniclla spectra*, *Nilaparvata lugens*, *Oncometopia* spp., *Orthezia praelonga*, *Oxya chinensis*, *Pachypsylla* spp., *Parabemisia myricae*, *Paratrioza* spp., *Parlatoria* spp., *Pemphigus* spp., *Peregrinus maidis*, *Phenacoccus* spp., *Phloeomyzus passerinii*, *Phorodon humuli*, *Phylloxera* spp., *Pinnaspis aspidistrae*, *Planococcus* spp., *Prosopidopsylla flava*, *Protopulvinaria pyriformis*, *Pseudaulacaspis pentagona*, *Pseudococcus* spp., *Psyllopsis* spp., *Psylla* spp., *Pteromalus* spp., *Pyrilla* spp., *Quadraspidiotus* spp., *Quesada gigas*, *Rastrococcus* spp., *Rhopalosiphum* spp., *Saissetia* spp., *Scaphoideus titanus*, *Schizaphis graminum*, *Selenaspidus articulatus*, *Sogata* spp., *Sogatella furcifera*, *Sogatodes* spp., *Stictocephala festina*, *Siphoninus phillyreae*, *Tenalaphara malayensis*, *Tetragonocephela* spp., *Tinocallis caryaefoliae*, *Tomaspis* spp., *Toxoptera* spp., *Trialeurodes vaporariorum*, *Trioza* spp., *Typhlocyba* spp., *Unaspis* spp., *Viteus vitifolii*, *Zygina* spp.;

from the order of the Hymenoptera, for example *Acromyrmex* spp., *Athalia* spp., *Atta* spp., *Diprion* spp., *Hoplocampa* spp., *Lasius* spp., *Monomorium pharaonis*, *Sirex* spp., *Solenopsis invicta*, *Tapinoma* spp., *Urocerus* spp., *Vespa* spp., *Xeris* spp.;

from the order of the Isopoda, for example *Armadillidium vulgare*, *Oniscus asellus*, *Porcellio scaber*;

from the order of the Isoptera, for example *Coptotermes* spp., *Cornitermes cumulans*, *Cryptotermes* spp., *Incisitermes* spp., *Microtermes obesi*, *Odontotermes* spp., *Reticulitermes* spp.;

from the order of the Lepidoptera, for example *Achroia grisella*, *Acronicta major*, *Adoxophyes* spp., *Aedia leucomelas*, *Agrotis* spp., *Alabama* spp., *Amyelois transitella*, *Anarsia* spp., *Anticarsia* spp., *Argyroploce* spp., *Barathra brassicae*, *Borbo cinnara*, *Bucculatrix thurberiella*, *Bupalus piniarius*, *Busseola* spp., *Cacoecia* spp., *Caloptilia theivora*, *Capua reticulana*, *Carpocapsa pomonella*, *Carposina niponensis*, *Cheimatobia brumata*, *Chilo* spp., *Choristoneura* spp., *Clysia ambiguella*, *Cnaphalocerus* spp., *Cnaphalocrocis medinalis*, *Cnephasia* spp., *Conopomorpha* spp., *Conotrachelus* spp., *Copitarsia* spp., *Cydia* spp., *Dalaca noctuides*, *Diaphania* spp., *Diatraea saccharalis*, *Earias* spp., *Ecdytolopha aurantium*, *Elasmopalpus lignosellus*, *Eldana saccharina*, *Ephestia* spp., *Epinotia* spp., *Epiphyas postvittana*, *Etiella* spp., *Eulia* spp., *Eupoecilia ambiguella*, *Euproctis* spp., *Euxoa* spp., *Feltia* spp., *Galleria mellonella*, *Gracillaria* spp., *Grapholitha* spp., *Hedylepta* spp., *Helicoverpa* spp., *Heliothis* spp., *Hofmannophila pseudospretella*, *Homoeosoma* spp., *Homona* spp., *Hyponomeuta padella*, *Kakivoria flavofasciata*, *Laphygma* spp., *Laspeyresia molesta*, *Leucinodes orbonalis*, *Leucoptera* spp., *Lithocolletis* spp., *Lithophane antennata*, *Lobesia* spp., *Loxagrotis albicosta*, *Lymantria* spp., *Lyonetia* spp., *Malacosoma neustria*, *Maruca testulalis*, *Mamstra brassicae*, *Melanitis leda*, *Mocis* spp., *Monopis obviella*, *Mythimna separata*, *Nemapogon cloacellus*, *Nymphula* spp., *Oiketicus* spp., *Oria* spp., *Orthaga* spp., *Ostrinia* spp., *Oulema oryzae*, *Panolis flammea*, *Parnara* spp., *Pectinophora* spp., *Perileucoptera* spp., *Phthorimaea* spp., *Phyllocnistis citrella*, *Phyllonorycter* spp., *Pieris* spp., *Platynota stultana*, *Plodia interpunctella*, *Plusia* spp., *Plutella xylostella*, *Prays* spp., *Prodenia* spp., *Protoparce* spp., *Pseudaletia* spp., *Pseudaletia unipuncta*, *Pseudoplusia includens*, *Pyrausta nubilalis*, *Rachiplusia nu*, *Schoenobius* spp., *Scirpophaga* spp., *Scirpophaga innotata*, *Scotia segetum*, *Sesamia* spp., *Sesamia inferens*, *Sparganothis* spp., *Spodoptera* spp., *Spodoptera praefica*, *Stathmopoda* spp., *Stomopteryx subsecivella*, *Synanthedon* spp., *Tecia solanivora*, *Thermesia gemmatalis*, *Tinea cloacella*, *Tinea pellionella*, *Tineola bisselliella*, *Tortrix* spp., *Trichophaga tapetzella*, *Trichoplusia* spp., *Tryporyza incertulas*, *Tuta absoluta*, *Virachola* spp.;

from the order of the Orthoptera or Saltatoria, for example *Acheta domesticus*, Dichroplus spp., *Gryllotalpa* spp., *Hieroglyphus* spp., *Locusta* spp., *Melanoplus* spp., *Schistocerca gregaria*;

from the order of the Phthiraptera, for example *Damalinia* spp., *Haematopinus* spp., *Linognathus* spp., *Pediculus* spp., *Phylloera vastatrix*, *Phtirus pubis*, *Trichodectes* spp.;

from the order of the Psocoptera, for example *Lepinotus* spp., *Liposcelis* spp.;

from the order of the Siphonaptera, for example *Ceratophyllus* spp., *Ctenocephalides* spp., *Pulex irritans*, *Tunga penetrans*, *Xenopsylla cheopsis*;

from the order of the Thysanoptera, for example *Anaphothrips obscurus*, *Baliothrips biformis*, *Drepanothrips reuteri*, *Enneothrips flavens*, *Frankliniella* spp., *Heliothrips* spp., *Hercinothrips femoralis*, *Rhipiphorothrips cruentatus*, *Scirtothrips* spp., *Taeniothrips cardamomi*, *Thrips* spp.;

from the order of the Zygentoma (=Thysanura), for example *Ctenolepisma* spp., *Lepisma saccharina*, *Lepismodes inquilinus*, *Thermobia domestica*;

from the class of the Symphyla, for example *Scutigerella* spp.;

pests from the phylum of the Mollusca, more particularly from the class of the Bivalvia, for example *Dreissena* spp., and also from the class of the Gastropoda, e.g. *Anion* spp., *Biomphalaria* spp., *Bulinus* spp., *Deroceras* spp., *Galba* spp., *Lymnaea* spp., *Oncomelania* spp., *Pomacea* spp., *Succinea* spp.;

animal parasites from the phyla of the Plathelminthes and Nematoda, for example *Ancylostoma duodenale*, *Ancylostoma ceylanicum*, *Ancylostoma braziliensis*, *Ancylostoma* spp., *Ascaris* spp., *Brugia malayi*, *Brugia timori*, *Bunostomum* spp., *Chabertia* spp., *Clonorchis* spp., *Cooperia* spp., *Dicrocoelium* spp., *Dictyocaulus filaria*, *Diphyllobothrium latum*, *Dracunculus medinensis*, *Echinococcus granulosus*, *Echinococcus multilocularis*, *Enterobius vermicularis*, *Faciola* spp., *Haemonchus* spp., *Heterakis* spp., *Hymenolepis nana*, *Hyostrongulus* spp., *Loa Loa*, *Nematodirus* spp., *Oesophagostomum* spp., *Opisthorchis* spp., *Onchocerca volvulus*, *Ostertagia* spp., *Paragonimus* spp., *Schistosomen* spp., *Strongyloides fuelleborni*, *Strongyloides stercoralis*, *Strongyloides* spp., *Taenia saginata*, *Taenia solium*, *Trichinella spiralis*, *Trichinella nativa*, *Trichinella britovi*, *Trichinella nelsoni*, *Trichinella pseudopsiralis*, *Trichostrongulus* spp., *Trichuris trichiura*, *Wuchereria bancrofti*;

plant pests from the phylum of the Nematoda, i.e. plant-parasitic nematodes, more particularly *Aphelenchoides* spp., *Bursaphelenchus* spp., *Ditylenchus* spp., *Globodera* spp., *Heterodera* spp., *Longidorus* spp., *Meloidogyne* spp., *Pratylenchus* spp., *Radopholus* spp., *Trichodorus* spp., *Tylenchulus* spp., *Xiphinema* spp., *Helicotylenchus* spp., *Tylenchorhynchus* spp., *Scutellonema* spp., *Paratrichodorus* spp., *Meloinema* spp., *Paraphelenchus* spp., *Aglenchus* spp., *Belonolaimus* spp., *Nacobbus* spp., *Rotylenchulus* spp., *Rotylenchus* spp., *Neotylenchus* spp., *Paraphelenchus* spp., *Dolichodorus* spp., *Hoplolaimus* spp., *Punctodera* spp., *Criconemella* spp., *Quinisulcius* spp., *Hemicycliophora* spp., *Anguina* spp., *Subanguina* spp., *Hemicriconemoides* spp., *Psilenchus* spp., *Pseudohalenchus* spp., *Criconemoides* spp., *Cacopaurus* spp.

In addition, it is possible to control, from the sub-kingdom of the Protozoa, the order of the Coccidia, for example *Eimeria* spp.

The compounds of the formula (I) can optionally, at certain concentrations or application rates, also be used as herbicides, safeners, growth regulators or agents to improve plant properties, or as microbicides, for example as fungicides, antimycotics, bactericides, viricides (including agents against viroids) or as agents against MLO (*mycoplasma*-like organisms) and RLO (*rickettsia*-like organisms). If appropriate, they can also be used as intermediates or precursors for the synthesis of other active compounds.

The present invention further relates to formulations and use forms prepared therefrom as crop protection compositions and/or pesticides, for example drench, drip and spray liquors, comprising at least one of the active compounds according to the invention. The use forms optionally comprise further crop protection agents and/or pesticides and/or action-improving adjuvants, such as penetrants, e.g. vegetable oils, for example rapeseed oil, sunflower oil, mineral oils, for example paraffin oils, alkyl esters of vegetable fatty acids, for example rapeseed oil methyl ester or soybean oil methyl ester, or alkanol alkoxylates, and/or spreaders, for example alkylsiloxanes, and/or salts, for example organic or inorganic ammonium or phosphonium salts, for example ammonium sulphate or diammonium hydrogenphosphate, and/or retention promoters, for example dioctyl sulphosuccinate or hydroxypropyl guar polymers, and/or humectants, for example glycerol, and/or fertilizers, for example ammonium-, potassium- or phosphorus-containing fertilizers.

Customary formulations are, for example, water-soluble liquids (SL), emulsion concentrates (EC), emulsions in water (EW), suspension concentrates (SC, SE, FS, OD), water-dispersible granules (WG), granules (GR) and capsule concentrates (CS); these and further possible formulation types are described, for example, by Crop Life International and in Pesticide Specifications, Manual on development and use of FAO and WHO specifications for pesticides, FAO Plant Production and Protection Papers—173, prepared by the FAO/WHO Joint Meeting on Pesticide Specifications, 2004, ISBN: 9251048576. The formulations, in addition to one or more active compounds according to the invention, optionally comprise further agrochemically active compounds.

These are preferably formulations or use forms which comprise auxiliaries, for example extenders, solvents, spontaneity promoters, carriers, emulsifiers, dispersants, frost protectants, biocides, thickeners and/or further auxiliaries, for example adjuvants. An adjuvant in this context is a component which enhances the biological effect of the formulation, without the component itself having any biological effect. Examples of adjuvants are agents which promote retention, spreading, attachment to the leaf surface or penetration.

These formulations are prepared in a known manner, for example by mixing the active compounds with auxiliaries, for example extenders, solvents and/or solid carriers, and/or further auxiliaries, for example surfactants. The formulations are produced either in suitable facilities or else before or during application.

Auxiliaries used may be substances capable of imparting particular properties, such as certain physical, technical and/or biological properties, to the formulation of the active compound, or the application forms prepared from these formulations (such as ready-to-use crop protection compositions, for example, such as spray liquors or seed dressings).

Suitable extenders are, for example, water, polar and non-polar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender utilized is water, it is also possible to use, for example, organic solvents as auxiliary solvents. Useful liquid solvents are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, and also water.

In principle, it is possible to use all suitable solvents. Examples of suitable solvents are aromatic hydrocarbons such as xylene, toluene or alkylnaphthalenes, chlorinated aromatic or aliphatic hydrocarbons such as chlorobenzene, chloroethylene or methylene chloride, aliphatic hydrocarbons such as cyclohexane, paraffins, petroleum fractions, mineral and vegetable oils, alcohols such as methanol, ethanol, isopropanol, butanol or glycol and their ethers and esters, ketones such as acetone, methyl ethyl ketone, methyl isobutyl ketone or cyclohexanone, strongly polar solvents such as dimethyl sulphoxide, and water.

In principle, it is possible to use all suitable carriers. Useful carriers especially include: for example ammonium salts and ground natural minerals such as kaolins, clays, talc, chalk, quartz, attapulgite, montmorillonite or diatomaceous earth, and ground synthetic materials such as finely divided silica, alumina and natural or synthetic silicates, resins, waxes and/or solid fertilizers. Mixtures of such carriers can likewise be used. Useful carriers for granules include: for example crushed and fractionated natural rocks such as calcite, marble, pumice, sepiolite, dolomite, and synthetic granules of inorganic and organic meals, and also granules of organic material such as sawdust, paper, coconut shells, maize cobs and tobacco stalks.

Liquefied gaseous extenders or solvents can also be used. Particularly suitable extenders or carriers are those which are gaseous at ambient temperature and under atmospheric pressure, for example aerosol propellant gases, such as halohydrocarbons, and also butane, propane, nitrogen and carbon dioxide.

Examples of emulsifiers and/or foam formers, dispersants or wetting agents with ionic or nonionic properties, or mixtures of these surfactants, include salts of polyacrylic acid, salts of lignosulphonic acid, salts of phenolsulphonic acid or naphthalenesulphonic acid, polycondensates of ethylene oxide with fatty alcohols or with fatty acids or with fatty amines, with substituted phenols (preferably alkylphenols or arylphenols), salts of sulphosuccinic esters, taurine derivatives (preferably alkyl taurates), phosphoric esters of polyethoxylated alcohols or phenols, fatty acid esters of polyols, and derivatives of the compounds containing sulphates, sulphonates and phosphates, for example alkylaryl polyglycol ethers, alkyl sulphonates, alkylsulphates, arylsulphonates, protein hydrolyzates, lignosulphite waste liquors and methylcellulose. The presence of a surfactant is advantageous when one of the active compounds and/or one of the inert carriers is insoluble in water and when application is carried out in water.

Further auxiliaries which may be present in the formulations and the use forms derived therefrom include dyes such as inorganic pigments, for example iron oxide, titanium oxide and Prussian Blue, and organic dyes such as alizarin dyes, azo dyes and metal phthalocyanine dyes, and nutrients and trace nutrients such as salts of iron, manganese, boron, copper, cobalt, molybdenum and zinc.

Additional components may be stabilizers, such as cold stabilizers, preservatives, antioxidants, light stabilizers, or other agents which improve chemical and/or physical stability. Foam generators or antifoams may also be present.

In addition, the formulations and the use forms derived therefrom may also comprise, as additional auxiliaries, stickers such as carboxymethyl cellulose and natural and synthetic polymers in the form of powders, granules or latices, such as gum arabic, polyvinyl alcohol and polyvinyl acetate, or else natural phospholipids such as cephalins and lecithins and synthetic phospholipids. Further possible auxiliaries are mineral and vegetable oils.

Optionally, further auxiliaries may be present in the formulations and the use forms derived therefrom. Examples of such additives include fragrances, protective colloids, binders, adhesives, thickeners, thixotropic agents, penetrants, retention promoters, stabilizers, sequestrants, complexing agents, humectants, spreaders. In general, the active compounds can be combined with any solid or liquid additive which is commonly used for formulation purposes.

Useful retention promoters include all those substances which reduce the dynamic surface tension, for example dioctyl sulphosuccinate, or increase the viscoelasticity, for example hydroxypropylguar polymers.

Penetrants contemplated in the present context include all those substances which are commonly used to promote the penetration of agrochemically active compounds into plants. Penetrants are defined in this context by their ability to penetrate from the (generally aqueous) application liquor and/or from the spray coating into the cuticle of the plant and thereby increase the mobility of the active compounds in the cuticle. The method described in the literature (Baur et al., 1997, Pesticide Science 51, 131-152) can be used for determining this property. Examples include alcohol alkoxylates such as coconut fatty ethoxylate (10) or isotridecyl ethoxylate (12), fatty acid esters, for example rapeseed oil methyl ester or soya oil methyl ester, fatty amine alkoxylates, for example tallowamine ethoxylate (15), or ammonium and/or phosphonium salts, for example ammonium sulphate or diammonium hydrogenphosphate.

The formulations preferably comprise between 0.00000001% and 98% by weight of active compound or, with particular preference, between 0.01% and 95% by weight of active compound, more preferably between 0.5% and 90% by weight of active compound, based on the weight of the formulation.

The active compound content of the use forms (crop protection compositions) prepared from the formulations can vary within wide limits. The active compound concentration of the use forms may typically be between 0.00000001% and 95% by weight of active compound, preferably between 0.00001% and 1% by weight, based on the weight of the use form. Application is accomplished in a customary manner appropriate for the use forms.

The treatment of the plants and plant parts with the active compounds according to the invention is carried out directly or by action on their surroundings, habitat or storage space using customary treatment methods, for example by dipping, spraying, atomizing, irrigating, evaporating, dusting, fogging, broadcasting, foaming, painting, spreading-on, injecting, watering (drenching), drip irrigating and, in the case of propagation material, in particular in the case of seed, furthermore by applying a powder for dry seed treatment, a solution for seed treatment, a water-soluble powder for slurry treatment, by incrusting, by coating with one or more coats, etc. It is furthermore possible to apply the active compounds by the ultra-low volume method or to inject the active compound preparation or the active compound itself into the soil.

A preferred direct treatment of the plants is foliar application, i.e. the active compounds according to the invention are applied to the foliage, it being possible to adjust the treatment frequency and the application rate according to the level of infestation with the pest in question.

In the case of systemically active compounds, the active compounds of the invention access the plants via the root system. In that case, the plants are treated by the action of the active compounds according to the invention on the habitat of the plant. This can be done, for example, by drenching, or by mixing into the soil or the nutrient solution, meaning that the locus of the plant (e.g. soil or hydroponic systems) is impregnated with a liquid form of the active compounds according to the invention, or by soil application, i.e. the active compounds according to the invention are introduced in solid form (e.g. in the form of granules) into the locus of the plants. In the case of paddy rice crops, this can also be done by metering the invention in a solid application form (for example as granules) into a flooded paddy field.

The active compounds according to the invention can be combined with microorganisms.

The microorganisms, given good plant tolerance, favourable homeotherm toxicity and good environmental compatibility, are suitable for protecting plants and plant organs, for increasing harvest yields, for improving the quality of the harvested material and for controlling animal pests, especially insects, arachnids, helminths, nematodes and molluscs, which are encountered in agriculture, in horticulture, in animal husbandry, in forests, in gardens and leisure facilities, in the protection of stored products and of materials, and in the hygiene sector. They can preferably be used as crop protection agents. They are effective against normally sensitive and resistant species and against all or some stages of development. The abovementioned microorganisms include:

microorganisms from the group of the bacteria, microorganisms from the group of the fungi, insecticidal microorganisms from the group of the protozoa, insecticidal microorganisms from the group of the viruses and microorganisms from the group of the entomopathogenic nematodes.

The active compounds according to the invention can be used as such or in formulations thereof, including in a mixture with one or more suitable fungicides, bactericides, acaricides, molluscicides, nematicides, insecticides, microbiologicals, useful organisms, fertilizers, bird repellants, phytotonics, sterilants, synergists, safeners, semiochemicals and/or plant growth regulators, in order thus, for example, to broaden the spectrum of action, to prolong the duration of action, to increase the rate of action, to prevent repulsion or prevent evolution of resistance. In addition, active compound combinations of this kind can improve plant growth and/or tolerance to abiotic factors, for example high or low temperatures, to drought or to elevated water content or soil salinity. It is also possible to improve flowering and fruiting performance, optimize germination capacity and root development, facilitate harvesting and improve yields, influence maturation, improve the quality and/or the nutritional value of the harvested products, prolong storage life and/or improve the processability of the harvested products. By combining the active compounds according to the invention with mixing partners, synergistic effects are obtained, i.e. the efficacy of the particular mixture is greater than expected on the basis of the efficacies of the individual components. It is generally possible to use the combinations in premixes, tankmixes or readymixes, and also in seed applications.

Examples of useful mixing components are the following compounds:

Insecticides/Acaricides/Nematicides:

The active compounds mentioned here under their "common names" are known and are described for example in The Pesticide Manual, 14th Ed., British Crop Protection Council 2006, or can be searched for on the Internet (e.g. http://www.alanwood.net/pesticides).

(1) Acetylcholinesterase (AChE) inhibitors, for example
carbamates, for example alanycarb (II-1-1), aldicarb (II-1-2), bendiocarb (II-1-3), benfuracarb (II-1-4), butocarboxim (II-1-5), butoxycarboxim (II-1-6), carbaryl (II-1-7), carbofuran (II-1-8), carbosulfan (II-1-9), ethiofencarb (II-1-10), fenobucarb (II-1-11), formetanate (II-1-12), furathiocarb (II-1-13), isoprocarb (II-1-14), methiocarb (II-1-15), methomyl (II-1-16), metolcarb (II-1-17), oxamyl (II-1-18), pirimicarb (II-1-19), propoxur (II-1-20), thiodicarb (II-1-21), thiofanox (II-1-22), triazamate (II-1-23), trimethacarb (II-1-24), XMC (II-1-25) and xylylcarb (II-1-26); or
organophosphates, for example acephate (II-1-27), azamethiphos (II-1-28), azinphos-ethyl (II-1-29), azinphos-methyl (II-1-30), cadusafos (II-1-31), chlorethoxyfos (II-1-32), chlorfenvinphos (II-1-33), chlormephos (II-1-34), chlorpyrifos (II-1-35), chlorpyrifos-methyl (II-1-36), coumaphos (II-1-37), cyanophos (II-1-38), demeton-S-methyl (II-1-39), diazinon (II-1-40), dichlorvos/DDVP (II-1-41), dicrotophos (II-1-42), dimethoate (II-1-43), dimethylvinphos (II-1-44), disulfoton (II-1-45), EPN (II-1-46), ethion (II-1-47), ethoprophos (II-1-48), famphur (II-1-49), fenamiphos (II-1-50), fenitrothion (II-1-51), fenthion (II-1-52), fosthiazate (II-1-53), heptenophos (II-1-54), imicyafos (II-1-55), isofenphos (II-1-56), isopropyl O-(methoxyaminothiophosphoryl) salicylate (II-1-57), isoxathion (II-1-58), malathion (II-1-59), mecarbam (II-1-60), methamidophos (II-1-61), methidathion (II-1-62), mevinphos (II-1-63), monocrotophos (II-1-64), naled (II-1-65), ometoate (II-1-66), oxydemeton-methyl (II-1-67), parathion (II-1-68), parathion-methyl (II-1-69), phenthoate (II-1-70), phorate (II-1-71), phosalone (II-1-72), phosmet (II-1-73), phosphamidon (II-1-74), phoxim (II-1-75), pirimiphos-methyl (II-1-76), profenofos (II-1-77), propetamphos (II-1-78), prothiofos (II-1-79), pyraclofos (II-1-80), pyridaphenthion (II-1-81), quinalphos (II-1-82), sulfotep (II-1-83), tebupirimfos (II-1-84), temephos (II-1-85), terbufos (II-1-86), tetrachlorvinphos (II-1-87), thiometon (II-1-88), triazophos (II-1-89), trichlorfon (II-1-90) and vamidothion (II-1-91).

(2) GABA-gated chloride channel antagonists, for example
cyclodiene organochlorines, for example chlordane (II-2-1) and endosulfan (II-2-2); or
phenylpyrazoles (fiproles), for example ethiprole (II-2-3) and fipronil (II-2-4).

(3) Sodium channel modulators/voltage-dependent sodium channel blockers, for example
pyrethroids, for example acrinathrin (II-3-1), allethrin (II-3-2), d-cis-trans allethrin (II-3-3), d-trans allethrin (II-3-4), bifenthrin (II-3-5), bioallethrin (II-3-6), bioallethrin S-cyclopentenyl isomer (II-3-7), bioresmethrin (II-3-8), cyclopro-thrin (II-3-9), cyfluthrin (II-3-10), beta-cyfluthrin (II-3-11), cyhalothrin (II-3-12), lambda-cyhalothrin (II-3-13), gamma-cyhalothrin (II-3-14), cypermethrin (II-3-15), alpha-cypermethrin (II-3-16), beta-cypermethrin (II-3-17), theta-cypermethrin (II-3-18), zeta-cypermethrin (II-3-19), cyphenothrin [(1R)-trans isomers] (II-3-20), deltamethrin (II-3-21), empenthrin [(EZ)-(1R) isomers] (II-3-22), esfenvalerate (II- 3-23), etofenprox (II-3-24), fenpropathrin (II-3-25), fenvalerate (II-3-26), flucythrinate (II-3-27), flumethrin (II-3-28), tau-fluvalinate (II-3-29), halfenprox (II-3-30), imiprothrin (II-3-31), kadethrin (II-3-32), permethrin (II-3-33), phenothrin [(1R)-trans isomer] (II-3-34), prallethrin (II-3-35), pyrethrine (pyrethrum) (II-3-36), resmethrin (II-3-37), silafluofen (II-3-38), tefluthrin (II-3-39), tetramethrin (II-3-40), tetramethrin [(1R) isomers)] (II-3-41), tralomethrin (II-3-42) and transfluthrin (II-3-43); or DDT (II-3-44); or methoxychlor (II-3-45).

(4) Nicotinergic acetylcholine receptor (nAChR) agonists, for example neonicotinoids, for example acetamiprid (II-4-1), clothianidin (II-4-2), dinotefuran (II-4-3), imidacloprid (II-4-4), nitenpyram (II-4-5), thiacloprid (II-4-6) and thiamethoxam (II-4-7); or nicotine (II-4-8); or sulfoxaflor (II-4-9).

(5) Nicotinergic acetylcholine receptor (nAChR) allosteric activators, for example spinosyns, for example spinetora (II-5-1) and spinosad (II-5-2).

(6) Chloride channel activators, for example avermectins/milbemycins, e.g. abamectin (II-6-1), emamectin benzoate (II-6-2), lepimectin (II-6-3) and milbemectin (II-6-4).

(7) Juvenile hormone imitators, for example juvenile hormone analogues, for example hydroprene (II-7-1), kinoprene (II-7-2) and methoprene (II-7-3); or fenoxycarb (II-7-4); or pyriproxyfen (II-7-5).

(8) Active compounds with unknown or nonspecific mechanisms of action, for example alkyl halides, e.g. methyl bromide (II-8-1) and other alkyl halides; or chloropicrin (II-8-2); or sulphuryl fluoride (II-8-3); or borax (II-8-4); or tartar emetic (II-8-5).

(9) Selective antifeedants, for example pymetrozine (II-9-1); or flonicamid (II-9-2).

(10) Mite growth inhibitors, for example clofentezine (II-10-1), hexythiazox (II-10-2) and diflovidazin (II-10-3); or etoxazole (II-10-4).

(11) Microbial disruptors of the insect gut membrane, e.g. *Bacillus thuringiensis* subspecies *israelensis* (II-11-1), *Bacillus thuringiensis* subspecies *aizawai* (II-11-2), *Bacillus thuringiensis* subspecies *kurstaki* (II-11-3), *Bacillus thuringiensis* subspecies *tenebrionis* (II-11-4) and B.t. plant proteins: Cry1Ab, Cry1Ac, Cry1Fa, Cry1A.105, Cry2Ab, Vip3A, mCry3A, Cry3Ab, Cry3Bb, Cry34 Ab1/35Ab1 (II-11-5); or

*Bacillus sphaericus* (II-11-6).

(12) Oxidative phosphorylation inhibitors, ATP disruptors such as, for example, diafenthiuron (II-12-1); or organotin compounds, e.g. azocyclotin (II-12-2), cyhexatin (II-12-3) and fenbutatin oxide (II-12-4); or propargite (II-12-5); or tetradifon (II-12-6).

(13) Oxidative phosphorylation decouplers acting by interrupting the H proton gradient such as, for example, chlorfenapyr (II-13-1), DNOC (II-13-2) and sulfluramid (II-13-3).

(14) Nicotinergic acetylcholine receptor antagonists such as, for example, bensultap (II-14-1), cartap hydrochloride (II-14-2), thiocyclam (II-14-3) and thiosultap-sodium (II-14-4).

(15) Chitin biosynthesis inhibitors, type 0, such as, for example, bistrifluron (II-15-1), chlorfluazuron (II-15-2), diflubenzuron (II-15-3), flucycloxuron (II-15-4), flufenoxuron (II-15-5), hexaflumuron (II-15-6), lufenuron (II-15-7), novaluron (II-15-8), noviflumuron (II-15-9), teflubenzuron (II-15-10) and triflumuron (II-15-11).

(16) Chitin biosynthesis inhibitors, type 1, such as, for example, buprofezin (II-16-1).

(17) Moulting disruptors, dipteran such as, for example, cyromazine (II-17-1).

(18) Ecdysone receptor agonists such as, for example, chromafenozide (II-18-1), halofenozide (II-18-2), methoxyfenozide (II-18-3) and tebufenozide (II-18-4).

(19) Octopaminergic agonists such as, for example, amitraz (II-19-1).

(20) Complex-III electron transport inhibitors such as, for example, hydramethylnone (II-20-1); or acequinocyl (II-20-2); or fluacrypyrim (II-20-3).

(21) Complex-I electron transport inhibitors, for example METI acaricides, for example fenazaquin (II-21-1), fenpyroximate (II-21-2), pyrimidifen (II-21-3), pyridaben (II-21-4), tebufenpyrad (II-21-5) and tolfenpyrad (II-21-6); or rotenone (Derris) (II-21-7).

(22) Voltage-dependent sodium channel blockers, for example indoxacarb (II-22-1); or metaflumizone (II-22-2).

(23) Inhibitors of acetyl-CoA carboxylase, for example tetronic and tetramic acid derivatives, for example spirodiclofen (II-23-1), spiromesifen (II-23-2) and spirotetramat (II-23-3).

(24) Complex-IV electron transport inhibitors, for example phosphines, for example aluminium phosphide (II-24-1), calcium phosphide (II-24-2), phosphine (II-24-3) and zinc phosphide (II-24-4); or cyanide (II-24-5).

(25) Complex-II electron transport inhibitors, for example cyenopyrafen (II-25-1) and cyflumetofen (II-25-2).

(28) Ryanodine receptor effectors, for example diamides, for example chlorantraniliprole (II-28-1), cyantraniliprole (II-28-2) and flubendiamide (II-28-3).

Further active compounds with unknown mechanism of action such as, for example, amidoflumet (II-29-1), azadirachtin (II-29-2), benclothiaz (II-29-3), benzoximate (II-29-4), bifenazate (II-29-5), bromopropylate (II-29-6), chinomethionat (II-29-7), cryolite (II-29-8), dicofol (II-29-9), diflovidazin (II-29-10), fluensulfone (II-29-11), flufenerim (II-29-12), flufiprole (II-29-13), fluopyram (II-29-14), fufenozide (II-29-15), imidaclothiz (II-29-16), iprodione meperfluthrin (II-29-18), pyridalyl (II-29-19), pyrifluquinazon tetramethylfluthrin (II-29-21) and iodomethane (II-29-22); furthermore preparations based on *Bacillus firmus* (in particular strain CNCM 1-1582, for example VOTiVO™, BioNem) (II-29-23) and also the following known active compounds:

3-bromo-N-{2-bromo-4-chloro-6-[(1-cyclopropylethyl)carbamoyl]phenyl}-1-(3-chloropyridin-2-yl)-1H-pyrazole-5-carboxamide (II-29-24) (known from WO 2005/077934), 4-{[(6-bromopyrid-3-yl)methyl](2-fluoroethyl)amino}furan-2(5H)-one (II-29-25) (known from WO 2007/115644), 4-{[(6-fluoropyrid-3-yl)methyl](2,2-difluoroethyl)amino}furan-2(5H)-one (II-29-26) (known from WO 2007/115644), 4-{[(2-chloro-1,3-thiazol-5-yl)methyl](2-fluoroethyl)amino}furan-2(5H)-one (II-29-27) (known from WO 2007/115644, 4-{[(6-chloropyrid-3-yl)methyl](2-fluoroethyl)amino}furan-2(5H)-one (II-29-28) (known from WO 2007/115644), flupyradifurone (II-29-29), 4-{[(6-chloro-5-fluoropyrid-3-yl)methyl](methyl)amino}furan-2(5H)-one (II-29-30) (known from WO 2007/115643), 4-{[(5,6-dichloropyrid-3-yl)methyl](2-fluoroethyl)amino}furan-2(5H)-one (II-29-31) (known from WO 2007/115646), 4-{[(6-chloro-5-fluoropyrid-3-yl)methyl](cyclopropyl)amino}furan-2(5H)-one (II-29-32) (known from WO 2007/115643), 4-{[(6-chloropyrid-3-yl)methyl](cyclopropyl)amino}furan-2(5H)-one (II-29-33) (known from EP A 0 539 588), 4-{[(6-chloropyrid- 3-yl)methyl](methyl)amino}furan-2(5H)-one (II-29-34) (known from EP A 0 539 588), {[1-(6-chloropyridin-3-yl) ethyl](methyl)oxido-λ⁴-sulphanylidene}cyanamide (II-29-35) (known from WO2007/149134) and its diastereomers {[(1R)-1-(6-chloropyridin-3-yl)ethyl](methyl)oxido-λ⁴-sulphanylidene}cyanamide (A) (II-29-36) and {[(1S)-1-(6-chloropyridin-3-yl)ethyl](methyl)oxido-λ⁴-sulphanylidene}cyanamide (B) (II-29-37) (likewise known from WO 2007/149134) and also diastereomers [(R)-methyl (oxido){(1R)-1-[6-(trifluoromethyl)pyridin-3-yl]ethyl}-λ⁴-sulphanylidene]cyanamide (A1) (II-29-38) and [(S)-methyl (oxido){(1S)-1-[6-(trifluoromethyl)pyridin-3-yl]ethyl}-λ⁴-sulphanylidene]cyanamide (A2) (II-29-39), identified as diastereomer group A (known from WO 2010/074747, WO 2010/074751), [(R)-methyl(oxido){(1S)-1-[6-(trifluoromethyl)pyridin-3-yl]ethyl}-λ⁴-sulphanylidene]cyanamide (B1) (II-29-40) and [(S)-methyl(oxido){(1R)-1-[6-(trifluoromethyl)pyridin-3-yl]ethyl}-λ⁴-sulphanylidene]cyanamide (B2) (II-29-41), identified as diastereomer group B (likewise known from WO 2010/074747, WO 2010/074751) and 11-(4-chloro-2,6-dimethylphenyl)-12-hydroxy-1,4-dioxa-9-azadispiro[4.2.4.2]tetradec-11-en-10-one (II-29-42) (known from WO 2006/089633), 3-(4'-fluoro-2,4-dimethylbiphenyl-3-yl)-4-hydroxy-8-oxa-1-azaspiro[4.5]dec-3-en-2-one (II-29-43) (known from WO 2008/067911), 1-{2-fluoro-4-methyl-5-[(2,2,2-trifluoroethyl)sulphinyl]phenyl}-3-(trifluoromethyl)-1H-1,2,4-triazol-5-amine (II-29-44) (known from WO 2006/043635), afidopyropen (II-29-45) (known from WO 2008/066153), 2-cyano-3-(difluoromethoxy)-N,N-dimethylbenzolsulphonamide (II-29-46) (known from WO 2006/056433), 2-cyano-3-(difluoromethoxy)-N-methylbenzolsulphonamide (II-29-47) (known from WO 2006/100288), 2-cyano-3-(difluoromethoxy)-N-ethylbenzenesulphonamide (II-29-48) (known from WO 2005/035486), 4-(difluoromethoxy)-N-ethyl-N-methyl-1,2-benzothiazol-3-amine-1,1-dioxide (II-29-49) (known from WO 2007/057407), N-[1-(2,3-dimethylphenyl)-2-(3,5-dimethylphenyflethyl]-4,5-dihydro-1,3-thiazol-2-amine (II-29-50) (known from WO 2008/104503), {1'-[(2E)-3-(4-chlorophenyl)prop-2-en-1-yl]-5-fluorospiro [indol-3,4'-piperidine]-1 (2H)-yl}(2-chloropyridin-4-yl) methanone (II-29-51) (known from WO 2003/106457), 3-(2,5-dimethylphenyl)-4-hydroxy-8-methoxy-1,8-diazaspiro [4.5]dec-3-en-2-one (II-29-52) (known from WO 2009/049851), 3-(2,5-dimethylphenyl)-8-methoxy-2-oxo-1,8-diazaspiro[4.5]dec-3-en-4-yl ethyl carbonate (II-29-53) (known from WO 2009/049851), 4-(but-2-yn-1-yloxy)-6-(3,5-dimethylpiperidin-1-yl)-5-fluoropyrimidine (II-29-54) (known from WO 2004/099160), (2,2,3,3,4,4,5,5-octafluoropentyl)(3,3,3-trifluoropropyl)malononitrile (II-29-55) (known from WO 2005/063694), (2,2,3,3,4,4,5,5-octafluoropentyl)(3,3,4,4,4-pentafluorobutyl)malononitrile (II-29-56) (known from WO 2005/063694), 8-[2-(cyclopropylmethoxy)-4-(trifluoromethyl)phenoxy]-3-[6-(trifluoromethyl)pyridazin-3-yl]-3-azabicyclo[3.2.1]octane (II-29-57) (known from WO 2007/040280), flometoquin (II-29-58), PF1364 (CAS Reg. No. 1204776-60-2) (II-29-59) (known from JP 2010/018586), 5-[5-(3,5-dichlorophenyl)-5-(trifluoromethyl)-4,5-dihydro-1,2-oxazol-3-yl]-2-(1H-1,2,4-triazol-1-yl)benzonitrile (II-29-60) (known from WO 2007/075459), 5-[5-(2-chloropyridin-4-yl)-5-(trifluoromethyl)-4,5-dihydro-1,2-oxazol-3-yl]-2-(1H-1,2,4-triazol-1-yl)benzonitrile (II-29-61) (known from WO 2007/075459), 4-[5-(3,5-dichlorophenyl)-5-(trifluoromethyl)-4,5-dihydro-1,2-oxazol-3-yl]-2-methyl-N-{2-oxo-2-[(2,2,2-trifluoroethyl)amino]ethyl}benzamide (II-29-62) (known from WO 2005/085216), 4-{[(6-chloropyridin-3-yl)methyl](cyclopropyl)amino}-1,3-oxazol-2(5H)-one (II-29-63), 4-{[(6-chloropyridin-3-yl)methyl](2,2-difluoroethyl)amino}-1,3-oxazol-2(5H)-one (II-29-64), 4-{[(6-chloropyridin-3-yl)methyl](ethyl)amino}-1,3-oxazol-2(5H)-one (II-29-65), 4-{[(6-chloropyridin-3-yl)methyl](methyl)amino}-1,3-oxazol-2 (5H)-one (II-29-66) (all known from WO 2010/005692), pyflubumide (II-29-67) (known from WO 2002/096882), methyl 2-[2-({[3-bromo-1-(3-chloropyridin-2-yl)-1H-pyrazol-5-yl]carbonyl}amino)-5-chloro-3-methylbenzoyl]-2-methylhydrazinecarboxylate (II-29-68) (known from WO 2005/085216), methyl 2-[2-({[3-bromo-1-(3-chloropyridin-2-yl)-1H-pyrazol-5-yl]carbonyl}amino)-5-cyano-3-methylbenzoyl]-2-ethylhydrazinecarboxylate (II-29-69) (known from WO 2005/085216), methyl 2-[2-({[3-bromo-1-(3-chloropyridin-2-yl)-1H-pyrazol-5-yl]carbonyl}amino)-5-cyano-3-methylbenzoyl]-2-methylhydrazinecarboxylate (II-29-70) (known from WO 2005/085216), methyl 2-[3,5-dibromo-2-({[3-bromo-1-(3-chloropyridin-2-yl)-1H-pyrazol-5-yl]carbonyl}amino)benzoyl]-1,2-diethylhydrazinecarboxylate (II-29-71) (known from WO 2005/085216), methyl 2-[3,5-dibromo-2-({[3-bromo-1-(3-chloropyridin-2-yl)-1H-pyrazol-5-yl]carbonyl}amino)benzoyl]-2-ethylhydrazinecarboxylate (II-29-72) (known from WO 2005/085216), (5RS,7RS;5RS,7SR)-1-(6-chloro-3-pyridylmethyl)-1,2,3,5,6,7-hexahydro-7-methyl-8-nitro-5-propoxyimidazo[1,2-a] pyridine (II-29-73) (known from WO 2007/101369), 2-{6-[2-(5-fluoropyridin-3-yl)-1,3-thiazol-5-yl]pyridin-2-yl}pyrimidine (II-29-74) (known from WO 2010/006713), 2-{6-[2-(pyridin-3-yl)-1,3-thiazol-5-yl]pyridin-2-yl}pyrimidine (II-29-75) (known from WO 2010/006713), 1-(3-chloropyridin-2-yl)-N-[4-cyano-2-methyl-6-(methylcarbamoyl)phenyl]-3-{[5-(trifluoromethyl)-1H-tetrazol-1-yl]methyl}-1H-pyrazole-5-carboxamide (II-29-76) (known from WO 2010/069502), 1-(3-chloropyridin-2-yl)-N-[4-cyano-2-methyl-6-(methylcarbamoyl)phenyl]-3-{[5-(trifluoromethyl)-2H-tetrazol-2-yl]methyl}-1H-pyrazole-5-carboxamide (II-29-77) (known from WO 2010/069502), N-[2-(tert-butylcarbamoyl)-4-cyano-6-methylphenyl]-1-(3-chloropyridin-2-yl)-3-{[5-(trifluoromethyl)-1H-tetrazol-1-yl]methyl}-1H-pyrazole-5-carboxamide (II-29-78) (known from WO 2010/069502), N-[2-(tert-butylcarbamoyl)-4-cyano-6-methylphenyl]-1-(3-chloropyridin-2-yl)-3-{[5-(trifluoromethyl)-2H-tetrazol-2-yl]methyl}-1H-pyrazole-5-carboxamide (II-29-79) (known from WO 2010/069502), (1E)-N-[(6-chloropyridin-3-yl)methyl]-N'-cyano-N-(2,2-difluoroethyl)ethanimideamide (II-29-80) (known from WO 2008/009360), N-[2-(5-amino-1,3,4-thiadiazol-2-yl)-4-chloro-6-methylphenyl]-3-bromo-1-(3-chloropyridin-2-yl)-1H-pyrazole-5-carboxamide (II-29-81) (known from CN 102057925) and methyl 2-[3,5-dibromo-2-({[3-bromo-1-(3-chloropyridin-2-yl)-1H-pyrazol-5-yl]carbonyl}amino)benzoyl]-2-ethyl-1-methylhydrazinecarboxylate (II-29-82) (known from WO 2011/049233), heptafluthrin (II-29-83), pyriminostrobin (II-29-84), flufenoxystrobin (II-29-85) and 3-chloro-N²-(2-cyanopropan-2-yl)-N¹-[4-(1,1,1,2,3,3,3-heptafluoropropan-2-yl)-2-methylphenyl]phthalamide (II-29-86) (known from WO2012/034472).

Fungicides (1) Ergosterol biosynthesis inhibitors, for example aldimorph, azaconazole, bitertanol, bromuconazole, cyproconazole, diclobutrazole, difenoconazole, diniconazole, diniconazole-M, dodemorph, dodemorph acetate, epoxiconazole, etaconazole, fenarimol, fenbuconazole, fenhexamid, fenpropidin, fenpropimorph, fluquinconazole, flurprimidol, flusilazole, flutriafol, furconazole, furconazole-cis, hexaconazole, imazalil, imazalil sulphate, imibenconazole, ipconazole, metconazole, myclobutanil, naftifin, nuarimol, oxpoconazole, paclobutrazole, pefurazoate, penconazole, piperalin, prochloraz, propiconazole, prothioconazole, pyributicarb, pyrifenox, quinconazole, simeconazole, spiroxamine, tebuconazole, terbinafine, tetraconazole, triadimefon, triadimenol, tridemorph, triflumizole, triforine, triticonazole, uniconazole, uniconazole-p, viniconazole, voriconazole, 1-(4-chlorophenyl)-2-(1H-1,2,4-triazol-1-yl)cycloheptanol, methyl 1-(2,2-dimethyl-2,3-dihydro-1H-inden-1-yl)-1H-imidazole-5-carboxylate, N'-{5-(difluoromethyl)-2-methyl-4-[3-(trimethylsilyl)propoxy]phenyl}-N-ethyl-N-methylimidoformamide, N-ethyl-N-methyl-N'-{2-methyl-5-(trifluoromethyl)-4-[3-(trimethylsilyl)propoxy]phenyl}imidoformamide and O-[1-(4-methoxyphenoxy)-3,3-dimethylbutan-2-yl]1H-imidazole-1-carbothioate.

(2) Respiration inhibitors (respiratory chain inhibitors), for example bixafen, boscalid, carboxin, diflumetorim, fenfuram, fluopyram, flutolanil, fluxapyroxad, furametpyr, furmecyclox, isopyrazam mixture of the syn-epimeric racemate 1RS,4SR,9RS and of the anti-epimeric racemate 1RS,4SR,9SR, isopyrazam (anti-epimeric racemate), isopyrazam (anti-epimeric enantiomer 1R,4S,9S), isopyrazam (anti-epimeric enantiomer 1S,4R,9R), isopyrazam (syn-epimeric racemate 1RS,4SR,9RS), isopyrazam (syn-epimeric enantiomer 1R,4S,9R), isopyrazam (syn-epimeric enantiomer 1S,4R,9S), mepronil, oxycarboxin, penflufen, penthiopyrad, sedaxane, thifluzamid, 1-methyl-N-[2-(1,1,2,2-tetrafluoroethoxyl)phenyl]-3-(trifluoromethyl)-1H-pyrazole-4-carboxamide, 3-(difluoromethyl)-1-methyl-N-[2-(1,1,2,2-tetrafluoroethoxyl)phenyl]-1H-pyrazole-4-carboxamide, 3-(difluoromethyl)-N-[4-fluoro-2-(1,1,2,3,3,3-hexafluoropropoxyl)phenyl]-1-methyl-1H-pyrazole-4-carboxamide, N-[1-(2,4-dichlorophenyl)-1-methoxypropan-2-yl]-3-(difluoromethyl)-1-methyl-1H-pyrazole-4-carboxamide, 5,8-difluoro-N-[2-(2-fluoro-4-{[4-(trifluoromethyl)pyridin-2-yl]oxy}phenyl)ethyl]quinazoline-4-amine, N-[9-(dichloromethylene)-1,2,3,4-tetrahydro-1,4-methanonaphthalen-5-yl]-3-(difluoromethyl)-1-methyl-1H-pyrazole-4-carboxamide, N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide and N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide.

(3) Respiration inhibitors (respiratory chain inhibitors) acting on complex III of the respiratory chain, for example ametoctradin, amisulbrom, azoxystrobin, cyazofamid, coumethoxystrobin, coumoxystrobin, dimoxystrobin, enestroburin, famoxadone, fenamidone, fenoxystrobin, fluoxastrobin, kresoxim-methyl, metominostrobin, orysastrobin, picoxystrobin, pyraclostrobin, pyrametostrobin, pyraoxystrobin, pyribencarb, triclopyricarb, trifloxystrobin, (2E)-2-(2-{[6-(3-chloro-2-methylphenoxy)-5-fluoropyrimidin-4-yl]oxy}phenyl)-2-(methoxyimino)-N-methylethanamide, (2E)-2-(methoxyimino)-N-methyl-2-(2-{[({(1E)-1-[3-(trifluoromethyl)phenyl]ethylidene}amino)oxy]methyl}phenyl)ethanamide, (2E)-2-(methoxyimino)-N-methyl-2-{2-[(E)-({1-[3-(trifluoromethyl)phenyl]ethoxy}imino)methyl]phenyl}ethanamide, (2E)-2-{2-[({[(1E)-1-(3-{[(E)-1-fluoro-2-phenylethenyl]oxy}phenyl)ethylidene]amino}oxy)methyl]phenyl}-2-(methoxyimino)-N-methylethanamide, (2E)-2-{2-[({[(2E,3E)-4-(2,6-dichlorophenyl)but-3-en-2-ylidene]amino}oxy)methyl]phenyl}-2-(methoxyimino)-N-methylethanamide, 2-chloro-N-(1,1,3-trimethyl-2,3-dihydro-1H-inden-4-yl)pyridine-3-carboxamide, 5-methoxy-2-methyl-4-(2-{[({1E)-1-[3-(trifluoromethyl)phenyl]ethylidene}amino)oxy]methyl}phenyl)-2,4-dihydro-3H-1,2,4-triazol-3-one, methyl (2E)-2-{2-[({cyclopropyl[(4-methoxyphenyl)imino]methyl}sulphanyl)methyl]phenyl}-3-methoxyprop-2-enoate, N-(3-ethyl-3,5,5-trimethylcyclohexyl)-3-(formylamino)-2-hydroxybenzamide, 2-{2-[(2,5-dimethylphenoxy)methyl]phenyl}-2-methoxy-N-methylacetamide and (2R)-2-{2-[(2,5-dimethylphenoxy)methyl]phenyl}-2-methoxy-N-methylacetamide.

(4) Mitosis and cell division inhibitors, for example benomyl, carbendazim, chlorfenazole, diethofencarb, ethaboxam, fluopicolide, fuberidazole, pencycuron, thiabendazole, thiophanate-methyl, thiophanate, zoxamide, 5-chloro-7-(4-methylpiperidin-1-yl)-6-(2,4,6-trifluorophenyl)[1,2,4]triazolo[1,5-a]pyrimidine and 3-chloro-5-(6-chloropyridin-3-yl)-6-methyl-4-(2,4,6-trifluorophenyl)pyridazine.

(5) Compounds with multisite activity, for example Bordeaux mixture, captafol, captan, chlorothalonil, copper preparations such as copper hydroxide, copper naphthenate, copper oxide, copper oxychloride, copper sulphate, dichlofluanid, dithianon, dodine, dodine free base, ferbam, fluorofolpet, folpet, guazatine, guazatine acetate, iminoctadine, iminoctadine albesilate, iminoctadine triacetate, mancopper, mancozeb, maneb, metiram, metiram zinc, oxine-copper, propamidine, propineb, sulphur and sulphur preparations, for example calcium polysulphide, thiram, tolylfluanid, zineb and ziram.

(6) Resistance inductors, for example acibenzolar-S-methyl, isotianil, probenazole and tiadinil.

(7) Amino acid and protein biosynthesis inhibitors, for example andoprim, blasticidin-S, cyprodinil, kasugamycin, kasugamycin hydrochloride hydrate, mepanipyrim, pyrimethanil and 3-(5-fluoro-3,3,4,4-tetramethyl-3,4-dihydroisoquinolin-1-yl)quinoline.

(8) ATP production inhibitors, for example fentin acetate, fentin chloride, fentin hydroxide and silthiofam.

(9) Cell wall synthesis inhibitors, for example benthiavalicarb, dimethomorph, flumorph, iprovalicarb, mandipropamid, polyoxins, polyoxorim, validamycin A and valifenalate.

(10) Lipid and membrane synthesis inhibitors, for example biphenyl, chloroneb, dicloran, edifenphos, etridiazole, iodocarb, iprobenfos, isoprothiolane, propamocarb, propamocarb hydrochloride, prothiocarb, pyrazophos, quintozene, tecnazene and tolclofos-methyl.

(11) Melanin biosynthesis inhibitors, for example carpropamid, diclocymet, fenoxanil, fthalide, pyroquilon, tricyclazole and 2,2,2-trifluoroethyl {3-methyl-1-[4-methylbenzoyl)amino]butan-2-yl}carbamate.

(12) Nucleic acid synthesis inhibitors, for example benalaxyl, benalaxyl-M (kiralaxyl), bupirimate, clozylacon, dimethirimol, ethirimol, furalaxyl, hymexazol, metalaxyl, metalaxyl-M (mefenoxam), ofurace, oxadixyl and oxolinic acid.

(13) Signal transduction inhibitors, for example chlozolinate, fenpiclonil, fludioxonil, iprodione, procymidone, quinoxyfen and vinclozolin.

(14) Decouplers, for example binapacryl, dinocap, ferimzone, fluazinam and meptyldinocap.

(15) Further compounds, for example benthiazole, bethoxazin, capsimycin, carvone, chinomethionat, pyriofenone (chlazafenone), cufraneb, cyflufenamid, cymoxanil, cyprosulphamide, dazomet, debacarb, dichlorophen, diclomezine, difenzoquat, difenzoquat methylsulphate, diphenylamine, ecomat, fenpyrazamine, flumetover, fluoromide, flusulphamide, flutianil, fosetyl-aluminium, fosetyl-calcium, fosetyl-sodium, hexachlorobenzene, irumamycin, methasulphocarb, methyl isothiocyanate, metrafenon, mildiomycin, natamycin, nickel dimethyldithiocarbamate, nitrothal-isopropyl, octhilinone, oxamocarb, oxyfenthiin, pentachlorophenol and salts thereof, phenothrin, phosphoric acid and salts thereof, propamocarb-fosetylate, propanosine-sodium, proquinazid, pyrimorph, (2E)-3-(4-tert-butylphenyl)-3-(2-chloropyridin-4-yl)-1-(morpholin-4-yl)prop-2-en-1-one, (2Z)-3-(4-tert-butylphenyl)-3-(2-chloropyridin-4-yl)-1-(morpholin-4-yl)prop-2-en-1-one, pyrrolnitrin, tebufloquin, tecloftalam, tolnifanid, triazoxide, trichlamide, zarilamide, (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate, 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-{4-[5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-methoxyphenoxy)-3,3-dimethylbutan-2-yl 1H-imidazole-1-carboxylate, 2,3,5,6-tetrachloro-4-(methylsulphonyl)pyridine, 2,3-dibutyl-6-chlorothieno[2,3-d]pyrimidin-4(3H)-one, 2,6-dimethyl-1H,5H-[1,4]dithiino[2,3-c:5,6-c']dipyrrole-1,3,5,7 (2H,6H)-tetrone, 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone, 2-[5-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1-yl)ethanone, 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone, 2-butoxy-6-iodo-3-propyl-4H-chromen-4-one, 2-chloro-5-[2-chloro-1-(2,6-difluoro-4-methoxyphenyl)-4-methyl-1H-imidazol-5-yl]pyridine, 2-phenylphenol and salts thereof, 3-(4,4,5-trifluoro-3,3-dimethyl-3,4-dihydroisoquinolin-1-yl)quinoline, 3,4,5-trichloropyridine-2,6-dicarbonitrile, 3-[5-(4-chlorophenyl)-2,3-dimethyl-1,2-oxazolidin-3-yl]pyridine, 3-chloro-5-(4-chlorophenyl)-4-(2,6-difluorophenyl)-6-methylpyridazine, 4-(4-chlorophenyl)-5-(2,6-difluorophenyl)-3,6-dimethylpyridazine, 5-amino-1,3,4-thiadiazole-2-thiol, 5-chloro-N'-phenyl-N'-(prop-2-yn-1-yl)thiophene-2-sulphonohydrazide, 5-fluoro-2-[(4-fluorobenzyl)oxy]pyrimidine-4-amine, 5-fluoro-2-[(4-methylbenzyl)oxy]pyrimidine-4-amine, 5-methyl-6-octyl[1,2,4]triazolo[1,5-a]pyrimidine-7-amine, ethyl (2Z)-3-amino-2-cyano-3-phenylprop-2-enoate, N'-(4-{[3-(4-chlorobenzyl)-1,2,4-thiadiazol-5-yl]oxy}-2,5-dimethylphenyl)-N-ethyl-N-methylimidoformamide, N-(4-chlorobenzyl)-3-[3-methoxy-4-(prop-2-yn-1-yloxy)phenyl]propanamide, N-[(4-chlorophenyl)(cyano)methyl]-3-[3-methoxy-4-(prop-2-yn-1-yloxy)phenyl]propanamide, N-[(5-bromo-3-chloropyridin-2-yl)methyl]-2,4-dichloropyridine-3-carboxamide, N-[1-(5-bromo-3-chloropyridin-2-yl)ethyl]-2,4-dichloropyridine-3-carboxamide, N-[1-(5-bromo-3-chloropyridin-2-yl)ethyl]-2-fluoro-4-iodopyridine-3-carboxamide, N-{(E)-[(cyclopropylmethoxy)imino][6-(difluoromethoxy)-2,3-difluorophenyl]methyl}-2-phenylacetamide, N-{(Z)-[(cyclopropylmethoxy)imino][6-(difluoromethoxy)-2,3-difluorophenyl]methyl}-2-phenylacetamide, N'-{4-[(3-tert-butyl-4-cyano-1,2-thiazol-5-yl)oxy]-2-chloro-5-methylphenyl}-N-ethyl-N-methylimidoformamide, N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide, N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide, N-methyl-2-(1-{[5-methyl-3-(trifluoromethyl)-1H-pyrazol-1-yl]acetyl}piperidin-4-yl)-N-[(1S)-1,2,3,4-tetrahydronaphthalen-1-yl]-1,3-thiazole-4-carboxamide, pentyl {6-[({[(1-methyl-1H-tetrazol-5-yl)(phenyl)methylidene]amino}oxy)methyl]pyridin-2-yl}carbamate, phenazine-1-carboxylic acid, quinolin-8-ol, quinolin-8-ol sulphate (2:1) and tert-butyl {6-[({[(1-methyl-1H-tetrazol-5-yl)(phenyl)methylene]amino}oxy)methyl]pyridin-2-yl}carbamate.

(16) Further compounds, for example 1-methyl-3-(trifluoromethyl)-N-[2'-(trifluoromethyl)biphenyl-2-yl]-1H-pyrazole-4-carboxamide, N-(4'-chlorobiphenyl-2-yl)-3-(difluoromethyl)-1-methyl-1H-pyrazole-4-carboxamide, N-(2',4'-dichlorobiphenyl-2-yl)-3-(difluoromethyl)-1-methyl-1H-pyrazole-4-carboxamide, 3-(difluoromethyl)-1-methyl-N-[4'-(trifluoromethyl)biphenyl-2-yl]-1H-pyrazole-4-carboxamide, N-(2',5'-difluorobiphenyl-2-yl)-1-methyl-3-(trifluoromethyl)-1H-pyrazole-4-carboxamide, 3-(difluoromethyl)-1-methyl-N-[4'-(prop-1-yn-1-yl)biphenyl-2-yl]-1H-pyrazole-4-carboxamide, 5-fluoro-1,3-dimethyl-N-[4'-(prop-1-yn-1-yl)biphenyl-2-yl]-1H-pyrazole-4-carboxamide, 2-chloro-N-[4'-(prop-1-yn-1-yl)biphenyl-2-yl]pyridine-3-carboxamide, 3-(difluoromethyl)-N-[4'-(3,3-dimethylbut-1-yn-1-yl)biphenyl-2-yl]-1-methyl-1H-pyrazole-4-carboxamide, N-[4'-(3,3-dimethylbut-1-yn-1-yl)biphenyl-2-yl]-5-fluoro-1,3-dimethyl-1H-pyrazole-4-carboxamide, 3-(difluoromethyl)-N-(4'-ethynylbiphenyl-2-yl)-1-methyl-1H-pyrazole-4-carboxamide, N-(4'-ethynylbiphenyl-2-yl)-5-fluoro-1,3-dimethyl-1H-pyrazole-4-carboxamide, 2-chloro-N-(4'-ethynylbiphenyl-2-yl)pyridine-3-carboxamide, 2-chloro-N-[4'-(3,3-dimethylbut-1-yn-1-yl)biphenyl-2-yl]pyridine-3-carboxamide, 4-(difluoromethyl)-2-methyl-N-[4'-(trifluoromethyl)biphenyl-2-yl]-1,3-thiazole-5-carboxamide, 5-fluoro-N-[4'-(3-hydroxy-3-methylbut-1-yn-1-yl)biphenyl-2-yl]-1,3-dimethyl-1H-pyrazole-4-carboxamide, 2-chloro-N-[4'-(3-hydroxy-3-methylbut-1-yn-1-yl)biphenyl-2-yl]pyridine-3-carboxamide, 3-(difluoromethyl)-N-[4'-(3-methoxy-3-methylbut-1-yn-1-yl)biphenyl-2-yl]-1-methyl-1H-pyrazole-4-carboxamide, 5-fluoro-N-[4'-(3-methoxy-3-methylbut-1-yn-1-yl)biphenyl-2-yl]-1,3-dimethyl-1H-pyrazole-4-carboxamide, 2-chloro-N-[4'-(3-methoxy-3-methylbut-1-yn-1-yl)biphenyl-2-yl]pyridine-3-carboxamide, (5-bromo-2-methoxy-4-methylpyridin-3-yl)(2,3,4-trimethoxy-6-methylphenyl)methanone, N-[2-(4-{[3-(4-chlorophenyl)prop-2-yn-1-yl]oxy}-3-methoxyphenyl)ethyl]-N2-(methylsulphonyl)valinamide, 4-oxo-4-[(2-phenylethyl)amino]butanoic acid and but-3-yn-1-yl {6-[({[(Z)-(1-methyl-1H-tetrazol-5-yl)(phenyl)methylene]amino}oxy)methyl]pyridin-2-yl}carbamate.

All the mixing partners mentioned in classes (1) to (16), as the case may be, may form salts with suitable bases or acids if they are capable of doing so on the basis of their functional groups.

All plants and parts of plants can be treated in accordance with the invention. Plants in this context are understood to include all plants and plant populations, such as desired and unwanted wild plants or crop plants (including naturally occurring crop plants). Crop plants may be plants which can be obtained by conventional breeding and optimization methods or by biotechnological and genetic engineering methods or combinations of these methods, including the transgenic plants and including the plant cultivars which are protectable and non-protectable by plant breeders' rights. Parts of plants shall be understood to mean all parts and organs of the plants above and below ground, such as shoot, leaf, flower and root, examples given being leaves, needles, stalks, stems, flowers, fruit bodies, fruits and seeds, and also tubers, roots and rhizomes. Parts of plants also include harvested material and vegetative and generative propagation material, for example cuttings, tubers, rhizomes, slips and seeds.

As already mentioned above, it is possible to treat all plants and their parts according to the invention. In a preferred embodiment, wild plant species and plant cultivars, or those obtained by conventional biological breeding, such as crossing or protoplast fusion, and parts thereof, are treated. In a further preferred embodiment, transgenic plants and plant cultivars obtained by genetic engineering methods, if appropriate in combination with conventional methods (genetically modified organisms), and parts thereof are treated. The term "parts" or "parts of plants" or "plant parts" has been explained above. Particular preference is given in accordance with the invention to treating plants of the respective commercially customary cultivars or those that are in use. Plant cultivars are understood to mean plants having new properties ("traits") and which have been obtained by conventional breeding, by mutagenesis or by recombinant DNA techniques. They may be cultivars, varieties, biotypes or genotypes.

The treatment according to the invention of the plants and plant parts with the active compounds is carried out directly or by allowing them to act on the surroundings, habitat or storage space thereof by the customary treatment methods, for example by dipping, spraying, evaporating, fogging, scattering, painting on, injecting, pouring on, and, in the case of propagation material, in particular in the case of seeds, also by applying one or more coats.

Preferred plants are those from the group of the useful plants, ornamental plants, turfgrass types, commonly used trees which are employed as ornamentals in public and domestic areas, and forestry trees. Forestry trees include trees for the production of timber, cellulose, paper and products made from parts of the trees.

The term useful plants as used here refers to crop plants which are used as plants for obtaining foods, animal feeds, fuels or for industrial purposes.

The useful plants which can be treated with the active compounds according to the invention include, for example, the following plant species: turf, vines, cereals, for example wheat, barley, rye, oats, rice, maize and millet/sorghum; beet, for example sugar beet and fodder beet; fruits, for example pome fruit, stone fruit and soft fruit, for example apples, pears, plums, peaches, almonds, cherries and berries, for example strawberries, raspberries, blackberries; legumes, for example beans, lentils, peas and soya beans; oil crops, for example oilseed rape, mustard, poppies, olives, sunflowers, coconuts, castor oil plants, cacao beans and peanuts; cucurbits, for example pumpkin/squash, cucumbers and melons; fibre plants, for example cotton, flax, hemp and jute; citrus fruit, for example, oranges, lemons, grapefruit and tangerines; vegetables, for example spinach, lettuce, asparagus, cabbage species, carrots, onions, tomatoes, potatoes and bell peppers; Lauraceae, for example avocado, *Cinnamomum*, camphor, or also plants such as tobacco, nuts, coffee, aubergine, sugarcane, tea, pepper, grapevines, hops, bananas, latex plants and ornamentals, for example flowers, shrubs, deciduous trees and coniferous trees. This enumeration does not represent any limitation.

Particularly suitable target crops for the treatment with the active compounds according to the invention are considered to be the following plants: cotton, aubergine, turf, pome fruit, stone fruit, soft fruit, maize, wheat, barley, cucumber, tobacco, vines, rice, cereals, pear, beans, soya beans, oilseed rape, tomato, bell pepper, melons, cabbage, potatoes and apples.

Examples of trees which can be improved in accordance with the method according to the invention include: *Abies* sp., *Eucalyptus* sp., *Picea* sp., *Pinus* sp., *Aesculus* sp., *Platanus* sp., *Tilia* sp., *Acer* sp., *Tsuga* sp., *Fraxinus* sp., *Sorbus* sp., *Betula* sp., *Crataegus* sp., *Ulmus* sp., *Quercus* sp., *Fagus* sp., *Salix* sp., *Populus* sp.

Preferred trees which can be improved by the method according to the invention include: from the tree species *Aesculus*: *A. hippocastanum*, *A. pariflora*, *A. carnea*; from the tree species *Platanus*: *P. aceriflora*, *P. occidentalis*, *P. racemosa*; from the tree species *Picea*: *P. abies*; from the tree species *Pinus*: *P. radiate*, *P. ponderosa*, *P. contorta*, *P. sylvestre*, *P. elliottii*, *P. montecola*, *P. albicaulis*, *P. resinosa*, *P. palustris*, *P. taeda*, *P. flexilis*, *P. jeffregi*, *P. baksiana*, *P. strobes*; from the tree species *Eucalyptus*: *E. grandis*, *E. globulus*, *E. camadentis*, *E. nitens*, *E. obliqua*, *E. regnans*, *E. pilularus*.

Particularly preferred trees which can be improved in accordance with the method according to the invention are: from the tree species *Pinus*: *P. radiate*, *P. ponderosa*, *P. contorta*, *P. sylvestre*, *P. strobes*; from the tree species *Eucalyptus*: *E. grandis*, *E. globulus*, *E. camadentis*.

Very particularly preferred trees which can be improved by the method according to the invention are: horse chestnut, Platanaceae, linden tree, maple tree.

The present invention can also be applied to any turfgrass types, including cool-season turfgrasses and warm-season turfgrasses.

Depending on the plant species or plant cultivars, and the location and growth conditions (soils, climate, vegetation period, diet) thereof, the treatment according to the invention may also result in superadditive ("synergistic") effects. For example, the following effects extending beyond the effects that are actually to be expected are possible: reduced application rates and/or broadening of the activity spectrum and/or an increase in the activity of the compounds and compositions usable in accordance with the invention, better plant growth, increased tolerance to high or low temperatures, increased tolerance to drought or to levels of water or soil salinity, enhanced flowering performance, easier harvesting, accelerated ripening, higher yields, higher quality and/or higher nutritional value of the harvested products, increased storage life and/or processability of the harvested products.

The preferred transgenic plants or plant cultivars (those obtained by genetic engineering) which are to be treated in accordance with the invention include all plants which, through the genetic modification, received genetic material which imparts particular advantageous useful traits to these plants. Examples of such properties are better plant growth, increased tolerance to high or low temperatures, increased tolerance to drought or to levels of water or soil salinity, enhanced flowering performance, easier harvesting, accelerated ripening, higher yields, higher quality and/or higher nutritional value of the harvested products, better storage life and/or processability of the harvested products. Further and particularly emphasized examples of such properties are an improved defence of the plants against animal and microbial pests, such as against insects, mites, phytopathogenic fungi, bacteria and/or viruses, and also increased tolerance of the plants to certain herbicidally active compounds. Examples of transgenic plants include the important crop plants, such as cereals (wheat, rice), maize, soya, potatoes, sugarbeet, tomatoes, peas and other vegetable types, cotton, tobacco, oilseed rape, and also fruit plants (with the following fruits: apples, pears, citrus fruits and grapes), particular emphasis being given to maize, soya, potatoes, cotton, tobacco and oilseed rape. Traits that are particularly emphasized are improved defence of the plants against insects, arachnids, nematodes, slugs and snails by toxins formed in the plants, especially those formed in the plants by the genetic material from *Bacillus thuringiensis* (for example by the genes CryIA(a), CryIA (b), CryIA(c), CryIIA, CryIIIA, CryIIIB2, Cry9c, Cry2Ab, Cry3Bb and CryIF, and also combinations thereof) (referred to hereinafter as "Bt plants"). Traits that are also particularly emphasized are the improved defence of plants against fungi, bacteria and viruses by systemic acquired resistance (SAR), systemin, phytoalexins, elicitors, and also resistance genes and correspondingly expressed proteins and toxins. Traits that are furthermore particularly emphasized are the increased tolerance of the plants to certain herbicidally active compounds, for example imidazolinones, sulphonylureas, glyphosate or phosphinothricin (for example the "PAT" gene). The genes which impart the desired traits in question may also be present in combinations with one another in the transgenic plants. Examples of "Bt plants" include maize varieties, cotton varieties, soya varieties and potato varieties which are sold under the trade names YIELD GARD® (for example corn, cotton, soya), KnockOut® (for example corn), StarLink® (for example corn), Bollgard® (cotton), Nucotn® (cotton) and NewLeaf® (potato). Examples of herbicide-tolerant plants include maize varieties, cotton varieties and soya varieties which are sold under the trade names Roundup Ready® (tolerance to glyphosate, for example maize, cotton, soya), Liberty Link® (tolerance to phosphinothricin, for example oilseed rape), IMI® (tolerance to imidazolinones) and STS (tolerance to sulphonylureas, for example maize). Herbicide-resistant plants (plants bred in a conventional manner for herbicide tolerance) which may be mentioned include the varieties sold under the name Clearfield® (for example corn). Of course, these statements also apply to plant cultivars which have these genetic traits or genetic traits which are yet to be developed and will be developed and/or marketed in the future.

The plants listed can be treated in accordance with the invention in a particularly advantageous manner with the compounds of the general formula (I) and/or the active compound mixtures according to the invention. The areas of preference stated above for the active compounds or mixtures also apply to the treatment of these plants. Particular emphasis is given to the treatment of plants with the compounds or mixtures specifically mentioned in the present text.

In the animal health field, i.e. in the field of veterinary medicine, the active compounds according to the invention are active against animal parasites, especially ectoparasites or endoparasites. The term "endoparasites" includes especially helminths and protozoa, such as coccidia. Ectoparasites are typically and preferably arthropods, especially insects and acarids.

In the field of veterinary medicine, the compounds according to the invention having favourable homeotherm toxicity are suitable for the control of parasites encountered in animal breeding and animal husbandry in livestock, breeding, zoo, laboratory, experimental and domestic animals. They are active against all or specific stages of development of the parasites.

Agricultural livestock include, for example, mammals, such as sheep, goats, horses, donkeys, camels, buffalo, rabbits, reindeer, fallow deer and especially cattle and pigs; or poultry such as turkeys, ducks, geese and especially chickens; or fish or crustaceans, for example in aquaculture; or, as the case may be, insects such as bees.

Domestic animals include, for example, mammals, such as hamsters, guinea pigs, rats, mice, chinchillas, ferrets or especially dogs, cats; cage birds; reptiles; amphibians or aquarium fish.

In a preferred embodiment, the compounds according to the invention are administered to mammals In another preferred embodiment, the compounds according to the invention are administered to birds, namely cage birds or especially poultry.

The use of the active compounds according to the invention for the control of animal parasites is intended to reduce or prevent illness, cases of deaths and performance losses (in the case of meat, milk, wool, hides, eggs, honey and the like), so that more economical and simpler animal keeping is enabled and better animal well-being is achievable.

In relation to the field of animal health, the term "control" or "controlling" means that the active compounds can effectively reduce the incidence of the respective parasite in an animal infected with such parasites to a harmless degree. More specifically, "controlling" as used herein means that the active compound can kill the respective parasite, inhibit its growth, or inhibit its proliferation.

Examples of arthropods include, but without any limitation:

from the order of the Anoplurida, for example *Haematopinus* spp., *Linognathus* spp., *Pediculus* spp., *Phtirus* spp., *Solenopotes* spp.; from the order of the Mallophagida and the suborders Amblycerina and Ischnocerina, for example *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.; from the order of the Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Odagmia* spp., *Wilhelmia* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp., *Rhinoestrus* spp., *Tipula* spp.; *from the order of the Siphonapterida, for example Pulex* spp., *Ctenocephalides* spp., *Tunga* spp., *Xenopsylla* spp., *Ceratophyllus* spp.; from the order of the Heteropterida, for example *Cimex* spp., *Triatoma* spp., *Rhodnius* spp., *Panstrongylus* spp.; as well as nuisance and hygiene pests from the order of the Blattarida.

In addition, among the arthropods, examples of Acari include the following, but without any limitation:

from the subclass of the Acari (Acarina) and the order of the Metastigmata, for example from the family of argasidae like *Argas* spp., *Ornithodorus* spp., *Otobius* spp., from the family of Ixodidae like *Ixodes* spp., *Amblyomma* spp., *Rhipicephalus (Boophilus)* spp., *Dermacentor* spp., *Haemophysalis* spp., *Hyalomma* spp., *Rhipicephalus* spp. (the original genus of multi-host ticks); from the order of Mesostigmata like *Dermanyssus* spp., *Ornithonyssus* spp., *Pneumonyssus* spp., *Raillietia* spp., *Pneumonyssus* spp., *Sternostoma* spp., *Varroa* spp., *Acarapis* spp.; from the order of the Actinedida (Prostigmata), for example *Acarapis* spp., *Cheyletiella* spp., *Ornithocheyletia* spp., *Myobia* spp., *Psorergates* spp., *Demodex* spp., *Trombicula* spp., *Neotrombiculla* spp., *Listrophorus* spp.; and from the order of the Acaridida (Astigmata), for example *Acarus* spp., *Tyrophagus* spp., *Caloglyphus* spp., *Hypodectes* spp., *Pterolichus* spp., *Psoroptes* spp., *Chori-*

*optes* spp., *Otodectes* spp., *Sarcoptes* spp., *Notoedres* spp., *Knemidocoptes* spp., *Cytodites* spp., *Laminosioptes* spp.

Examples of parasitic protozoa include, but without any limitation:

Mastigophora (*Flagellata*), for example Trypanosomatidae, for example, *Trypanosoma b. brucei*, *T.b. gambiense*, *T.b. rhodesiense*, *T. congolense*, *T. cruzi*, *T. evansi*, *T. equinum*, *T. lewisi*, *T. percae*, *T. simiae*, *T. vivax*, *Leishmania brasiliensis*, *L. donovani*, *L. tropica*, for example Trichomonadidae, for example, *Giardia lamblia*, *G. canis*.

Sarcomastigophora (Rhizopoda) such as Entamoebidae, for example, *Entamoeba histolytica*, Hartmanellidae, for example, *Acanthamoeba* sp., *Harmanella* sp. Apicomplexa (Sporozoa) such as Eimeridae, for example, *Eimeria acervulina*, *E. adenoides*, *E. alabamensis*, *E. anatis*, *E. anserina*, *E. arloingi*, *E. ashata*, *E. auburnensis*, *E. bovis*, *E. brunetti*, *E. canis*, *E. chinchillae*, *E. clupearum*, *E. columbae*, *E. contorta*, *E. crandalis*, *E. debliecki*, *E. dispersa*, *E. ellipsoidales*, *E. falciformis*, *E. faurei*, *E. flavescens*, *E. gallopavonis*, *E. hagani*, *E. intestinalis*, *E. iroquoina*, *E. irresidua*, *E. labbeana*, *E. leucarti*, *E. magna*, *E. maxima*, *E. media*, *E. meleagridis*, *E. meleagrimitis*, *E. mitis*, *E. necatrix*, *E. ninakohlyakimovae*, *E. ovis*, *E. parva*, *E. pavonis*, *E. perforans*, *E. phasani*, *E. piriformis*, *E. praecox*, *E. residua*, *E. scabra*, *E. spec.*, *E. stiedai*, *E. suis*, *E. tenella*, *E. truncata*, *E. truttae*, *E. zuernii*, *Globidium spec.*, *Isospora belli*, *I. canis*, *I. felis*, *I. ohioensis*, *I. rivolta*, *I. spec.*, *I. suis*, *Cystisospora spec.*, *Cryptosporidium spec.*, in particular *C. parvum*; such as Toxoplasmadidae, for example, *Toxoplasma gondii*, *Hammondia heydornii*, *Neospora caninum*, *Besnoitia besnoitii*; such as Sarcocystidae, for example, *Sarcocystis bovicanis*, *S. bovihominis*, *S. ovicanis*, *S. ovifelis*, *S. neurona*, *S. spec.*, *S. suihominis*, such as Leucozoidae, for example, *Leucozytozoon simondi*, such as Plasmodiidae, for example, *Plasmodium berghei*, *P. falciparum*, *P. malariae*, *P. ovale*, *P. vivax*, *P. spec.*, such as Piroplasmea, for example, *Babesia argentina*, *B. bovis*, *B. canis*, *B. spec.*, *Theileria parva*, *Theileria spec.*, such as Adeleina, for example, *Hepatozoon canis*, *H. spec.*

Examples of pathogenic endoparasites, which are helminths, include platyhelmintha (e.g. monogenea, cestodes and trematodes), nematodes, acanthocephala, and pentastoma. Further helminths include, but without any limitation:

Monogenea: for example: *Gyrodactylus* spp., *Dactylogyrus* spp., *Polystoma* spp.

Cestodes: from the order of the Pseudophyllidea for example: *Diphyllobothrium* spp., *Spirometra* spp., *Schistocephalus* spp., *Ligula* spp., *Bothridium* spp., *Diplogonoporus* spp.

From the order of the Cyclophyllida, for example: *Mesocestoides* spp., *Anoplocephala* spp., *Paranoplocephala* spp., *Moniezia* spp., *Thysanosoma* spp., *Thysaniezia* spp., *Avitellina* spp., *Stilesia* spp., *Cittotaenia* spp., *Andyra* spp., *Bertiella* spp., *Taenia* spp., *Echinococcus* spp., *Hydatigera* spp., *Davainea* spp., *Raillietina* spp., *Hymenolepis* spp., *Echinolepis* spp., *Echinocotyle* spp., *Diorchis* spp., *Dipylidium* spp., *Joyeuxiella* spp., *Diplopylidium* spp.

Trematodes: from the class of the Digenea, for example: *Diplostomum* spp., *Posthodiplostomum* spp., *Schistosoma* spp., *Trichobilharzia* spp., *Ornithobilharzia* spp., *Austrobilharzia* spp., *Gigantobilharzia* spp., *Leucochloridium* spp., *Brachylaima* spp., *Echinostoma* spp., *Echinoparyphium* spp., *Echinochasmus* spp., *Hypoderaeum* spp., *Fasciola* spp., *Fasciolides* spp., *Fasciolopsis* spp., *Cyclocoelum* spp., *Typhlocoelum* spp., *Paramphistomum* spp., *Calicophoron* spp., *Cotylophoron* spp., *Gigantocotyle* spp., *Fischoederius* spp., *Gastrothylacus* spp., *Notocotylus* spp., *Catatropis* spp., *Plagiorchis* spp., *Prosthogonimus* spp., *Dicrocoelium* spp., *Eurytrema* spp., *Troglotrema* spp., *Paragonimus* spp., *Collyriclum* spp., *Nanophyetus* spp., *Opisthorchis* spp., *Clonorchis* spp., *Metorchis* spp., *Heterophyes* spp., *Metagonimus* spp.

Nematodes: Trichinellida, for example: *Trichuris* spp., *Capillaria* spp., *Trichomosoides* spp., *Trichinella* spp.

From the order of the Tylenchida, for example: *Micronema* spp., *Strongyloides* spp.

From the order of the Rhabditina, for example: *Strongylus* spp., *Triodontophorus* spp., *Oesophagodontus* spp., *Trichonema* spp., *Gyalocephalus* spp., *Cylindropharynx* spp., *Poteriostomum* spp., *Cyclococercus* spp., *Cylicostephanus* spp., *Oesophagostomum* spp., *Chabertia* spp., *Stephanurus* spp., *Ancylostoma* spp., *Uncinaria* spp., *Bunostomum* spp., *Globocephalus* spp., *Syngamus* spp., *Cyathostoma* spp., *Metastrongylus* spp., *Dictyocaulus* spp., *Muellerius* spp., *Protostrongylus* spp.,

*Neostrongylus* spp., *Cystocaulus* spp., *Pneumostrongylus* spp., *Spicocaulus* spp., *Elaphostrongylus* spp. *Parelaphostrongylus* spp., *Crenosoma* spp., *Paracrenosoma* spp., *Angiostrongylus* spp., *Aelurostrongylus* spp., *Filaroides* spp., *Parafilaroides* spp., *Trichostrongylus* spp., *Haemonchus* spp., *Ostertagia* spp., *Marshallagia* spp., *Cooperia* spp., *Nematodirus* spp., *Hyostrongylus* spp., *Obeliscoides* spp., *Amidostomum* spp., *Ollulanus* spp.

From the order of the Spirurida, for example: *Oxyuris* spp., *Enterobius* spp., *Passalurus* spp., *Syphacia* spp., *Aspiculuris* spp., *Heterakis* spp.; *Ascaris* spp., *Toxascaris* spp., *Toxocara* spp., *Baylisascaris* spp., *Parascaris* spp., *Anisakis* spp., *Ascaridia* spp.; *Gnathostoma* spp., *Physaloptera* spp., *Thelazia* spp., *Gongylonema* spp., *Habronema* spp., *Parabronema* spp., *Draschia* spp., *Dracunculus* spp.; *Stephanofilaria* spp., *Parafilaria* spp., *Setaria* spp., *Loa* spp., *Dirofilaria* spp., *Litomosoides* spp., *Brugia* spp., *Wuchereria* spp., *Onchocerca* spp.

Acanthocephala: from the order of the Oligacanthorhynchida, for example: *Macracanthorhynchus* spp., *Prosthenorchis* spp.; from the order of the Polymorphida, for example: *Filicollis* spp.; from the order of the Moniliformida, for example: *Moniliformis* spp.

From the order of the Echinorhynchida, for example, *Acanthocephalus* spp., *Echinorhynchus* spp., *Leptorhynchoides* spp.

Pentastoma: from the order of the Porocephalida, for example, *Linguatula* spp.

In the veterinary field and in animal keeping, the active compounds according to the invention are administered by methods commonly known in the art, such as enterally, parenterally, dermally or nasally, in the form of suitable preparations. Administration may be prophylactic or therapeutic.

Thus, one embodiment of the present invention refers to compounds according to the invention for use as a medicament.

A further aspect relates to compounds according to the invention for use as an antiendoparasitic agent, in particular a helminthicidal agent or antiprotozoic agent. For example, the compounds according to the invention are suitable for use as an antiendoparasitic agent, in particular a helminthicidal agent or antiprotozoic agent, for example in animal husbandry, in animal breeding, in animal housing and in the hygiene sector.

Yet a further aspect relates to compounds according to the invention for use as an antiectoparasitic agent, in particular an arthropodicidal agent, such as an insecticide or acaricide. For example, compounds according to the invention are suitable for use as an antiectoparasitic agent, especially an arthropodicidal agent such as an insecticide or acaricide, for example in animal husbandry, in animal breeding, in animal housing and in the hygiene sector.

The compounds according to the invention are suitable for controlling animal pests in the hygiene sector. More particularly, the invention can be used in the domestic sector, in the hygiene sector and in the protection of stored products, particularly for control of insects, arachnids and mites encountered in enclosed spaces, for example dwellings, factory halls, offices, vehicle cabins. For control of animal pests, the active compounds or compositions are used alone or in combination with other active compounds and/or auxiliaries. They are preferably used in domestic insecticide products. The active compounds according to the invention are effective against sensitive and resistant species, and against all developmental stages.

These pests include, for example, pests from the class Arachnida, from the orders Scorpiones, Araneae and Opiliones, from the classes Chilopoda and Diplopoda, from the class Insecta the order Blattodea, from the orders Coleoptera, Dermaptera, Diptera, Heteroptera, Hymenoptera, Isoptera, Lepidoptera, Phthiraptera, Psocoptera, Saltatoria or Orthoptera, Siphonaptera and Zygentoma and from the class Malacostraca the order Isopoda.

Application is effected, for example, in aerosols, unpressurized spray products, for example pump and atomizer sprays, automatic fogging systems, foggers, foams, gels, evaporator products with evaporator tablets made of cellulose or plastic, liquid evaporators, gel and membrane evaporators, propeller-driven evaporators, energy-free, or passive, evaporation systems, moth papers, moth bags and moth gels, as granules or dusts, in baits for spreading or in bait stations.

The active compounds according to the invention are suitable for protecting industrial materials against attack or destruction by insects, for example from the orders Coleoptera, Hymenoptera, Isoptera, Lepidoptera, Psocoptera and Zygentoma.

Industrial materials in the present context are understood to mean inanimate materials, such as preferably plastics, adhesives, sizes, papers and cards, leather, wood, processed wood products and coating compositions. The use of the invention for protection of wood is particularly preferred.

In one embodiment of the invention, the compositions or agents according to the invention also comprise at least one further insecticide and/or at least one fungicide.

In a further embodiment, this composition according to the invention is a ready-to-use composition, meaning that it can be applied to the material in question without further modifications. Useful further insecticides or fungicides include those mentioned above.

It has also been found that, surprisingly, the active compounds according to the invention and compositions can be used to protect objects which come into contact with saltwater or brackish water, especially hulls, screens, nets, buildings, moorings and signalling systems, against fouling. The active compounds according to the invention and compositions can again be used alone or in combinations with other active ingredients as antifouling compositions.

Description of the Processes and Intermediates

The compounds of the formula (I) can be prepared by the processes described below. The processes for the preparation of the compounds of the formulae (Ia) and (Ib) in which A represents —C(=O)NR$^{13}$— (Process (A)) or —C(R$^{11}$)(R$^{12}$)NR$^{13}$C(=O)— (Process (B, C)) are given by way of example. The compounds of the formula (I) in which A represents —C(=S)NR$^{13}$—, —C(R$^{11}$)(U)NR$^{13}$C(=O)—, —C(R$^{11}$)(R$^{12}$)N(U)C(=O)— or —N(R$^{11}$)NR$^{13}$C(=O)— can be prepared in an analogous manner. The Preparation Processes (A), (B) and (C), illustrated below, for the compounds of the formulae (Ia) and (Ib) can be applied analogously to the analogous compounds in which W represents S (and not O).

(A) The compounds of the general formula (Ia)

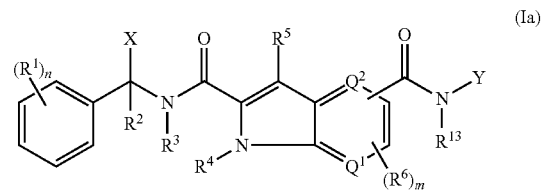

can be obtained by initially reacting carboxylic acid derivatives of the general formula (IIa)

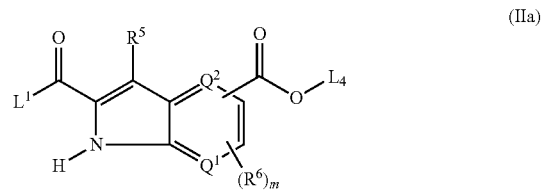

where

L$^1$ is hydroxyl or halogen and

L$^4$ is C$_1$-C$_4$-alkyl, with amines of the formula (III)

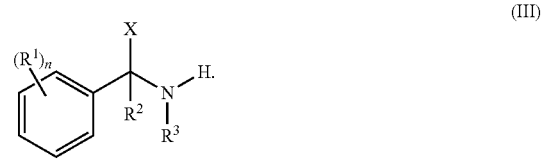

For (IIa), it is firstly possible to use an acid halide (e.g. L$^1$=chlorine) in the presence of a base, for example triethylamine or sodium hydroxide. However, secondly, it is also possible to employ the carboxylic acid (L$^1$=OH) using coupling reagents, for example dicyclohexylcarbodiimide, and additives such as 1-hydroxybenzotriazole [Chem. Ber. 1970, 788]. It is also possible to use coupling reagents such as 1-ethyl-3-(3-dimethylaminopropyl)carbodiimide, 1,1'-carbonyl-1H-imidazole, N-[(1H-benzotriazol-1-yloxy)(dimethylamino)methylene]-N-methylmethanaminium hexafluorophosphate, and similar compounds. The coupling reagents used to perform the preparation process are all which are suitable for forming an ester or amide bond (cf. for example, Bodansky et al., Peptide Synthesis, 2nd ed., Wiley & Sons, New York, 1976; Gross, Meienhofer, The Peptide: Analysis, Synthesis, Biology, Academic Press, New York, 1979). In addition, it is also possible to use mixed anhydrides for preparing (Ia). [J. Am. Chem. Soc 1967, 5012]. In this process, it is possible to use various chloroformic esters, for example isobutyl chloroformate, isopropyl chloroformate. It is likewise possible to use diethylacetyl chloride, trimethylacetyl chloride and the like for this purpose.

The resulting carboxylic esters of the formula (IVa)

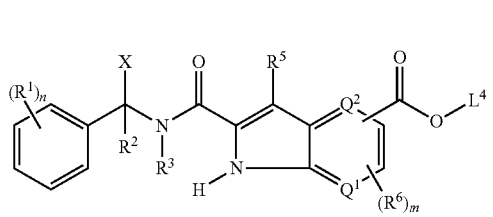
(IVa)

are subsequently reacted with alkylating agents of the formula (V) where $L^2$ represents a leaving group such as, for example, chlorine, bromine or iodine, $$R^4\text{-}L^2 \quad (V)$$

in the presence of bases, for example sodium hydride, giving compounds of the formula (VIa)

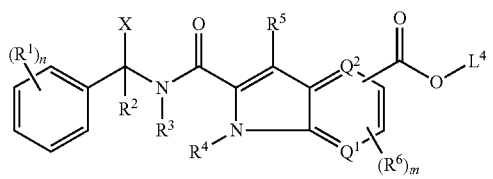
(VIa)

and subsequently reacted with amines of the general formula (VII)

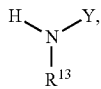
(VII)

where the reaction is preferably
a) carried out directly with esters of the formula (VIa) in the presence of an activating reagent, for example trimethylaluminium,
or, likewise preferably,
b) the esters of the formula (VIa) are initially hydrolysed under acidic or alkaline conditions to carboxylic acids of the formula (VIIa)

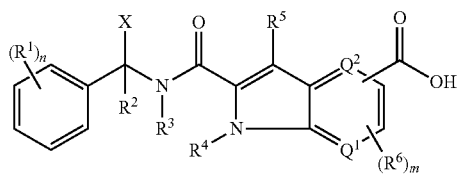
(VIIa)

and these are then reacted with amines of the formula (VII) in the presence of a condensing agent such as, for example, 1-ethyl-3-(3-dimethylaminopropyl)carbodiimide (EDC) or 2-(1H-benzotriazol-1-yl)-1,1,3,3-tetramethyluronoium hexafluorophosphate (HBTU).

(B) Compounds of the general formula (Ib)

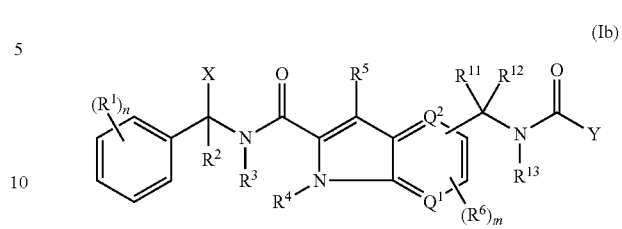
(Ib)

where $R^{11}$, $R^{12}$ and IC represent hydrogen can be obtained, for example, by initially reacting carboxylic acid derivatives of the general formula (IIb)

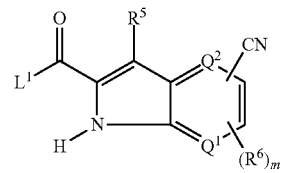
(IIb)

where $L^1$ represents halogen or represents a hydroxyl group, analogously to the process described in (A) with amines of the general formula (III)

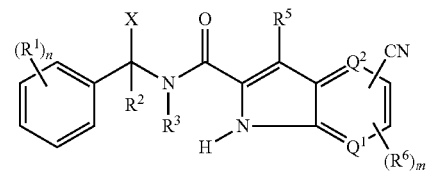
(III)

subsequently reacting the resulting compounds of the formula (IVb)

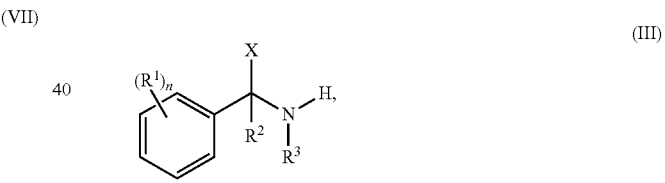
(IVb)

with alkylating agents of the formula (V), where $L^2$ represents a leaving group such as, for example, chlorine, bromine or iodine, $$R^4\text{-}L^2 \quad (V)$$

in the presence of a base, for example sodium hydride, giving compounds of the formula (VIb)

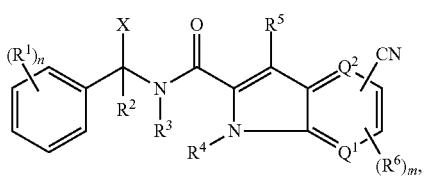
(VIb)

and finally reacting the cyano group with a suitable reducing agent, for example sodium borohydride, giving amines of the formula (VIIb)

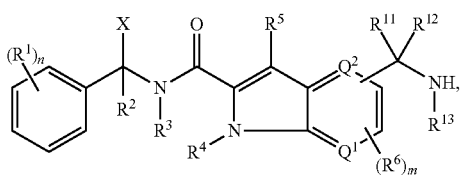
(VIIb)

and finally acylating this with a compound of the formula (VIII)

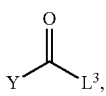
(VIII)

where
$L^3$ represents hydroxy, halogen or YC(O)O—.

For (VIII), it is firstly possible to use an acid halide (e.g. $L^3$=chlorine) in the presence of a base, for example triethylamine or sodium hydroxide. However, it is furthermore also possible to employ the carboxylic acid ($L^3$=OH) using coupling reagents, for example dicyclohexylcarbodiimide, and additives such as 1-hydroxybenzotriazole [Chem. Ber. 1970, 788]. It is also possible to use coupling reagents such as 1-ethyl-3-(3-dimethylaminopropyl)carbodiimide, 1,1'-carbonyl-1H-imidazole, N-[(1H-benzotriazol-1-yloxy)(dimethylamino)methylene]-N-methylmethanaminium hexafluorophosphate, and similar compounds. For (VIII), it is finally also possible to use a carboxylic anhydride ($L^3$=OC(O)Y) in the presence of a base, for example triethylamine.

(C) Compounds of the general formula (Ib)

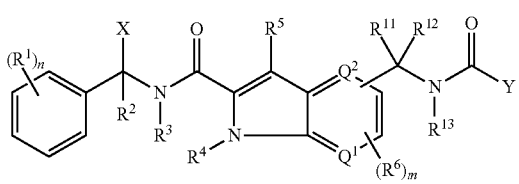
(Ib)

where $R^{11}$, $R^{12}$ and $R^{13}$ represent hydrogen can also be obtained, for example, by initially reacting carboxylic acid derivatives of the general formula (IIc)

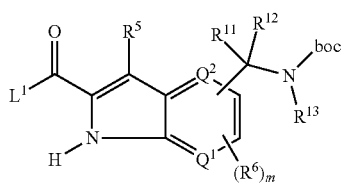
(IIc)

where
$L^1$ represents halogen or represents a hydroxyl group,
boc represents t-BuO—C(O)—
analogously to the process described in (A) with amines of the general formula (III)

(III)

subsequently reacting the resulting compounds of the formula (IVc)

(IVc)

with alkylating agents of the formula (V), where $L^2$ represents a leaving group such as, for example, chlorine, bromine or iodine, $R^4$-$L^2$ (V)

in the presence of a base, for example sodium hydride, giving compounds of the formula (VIc)

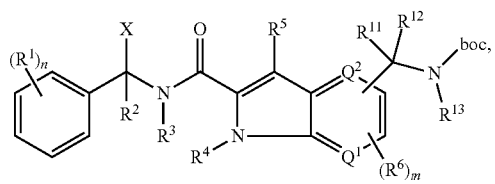
(VIc)

and subsequently removing the Boc protective group with an acid such as, for example trifluoroacetic acid. The resulting amines of the formula (VIIb)

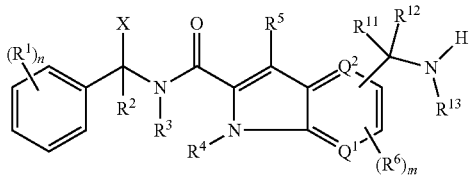

are finally acylated analogously to Process B with a compound of the formula (VIII)

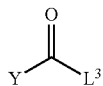

where $L^3$ represents hydroxy, halogen or YC(O)O—.

Azaindolecarboxylic acids of the formulae (IIa), (IIb) and (IIc) ($L_1$=OH) are novel and also form part of the subject-matter of the invention. They can be obtained analogously to known processes by the methods described in Schemes 1 and 2.

Indolecarboxylic acids of the formula (II-1a) can be obtained, for example, according to Scheme 1.

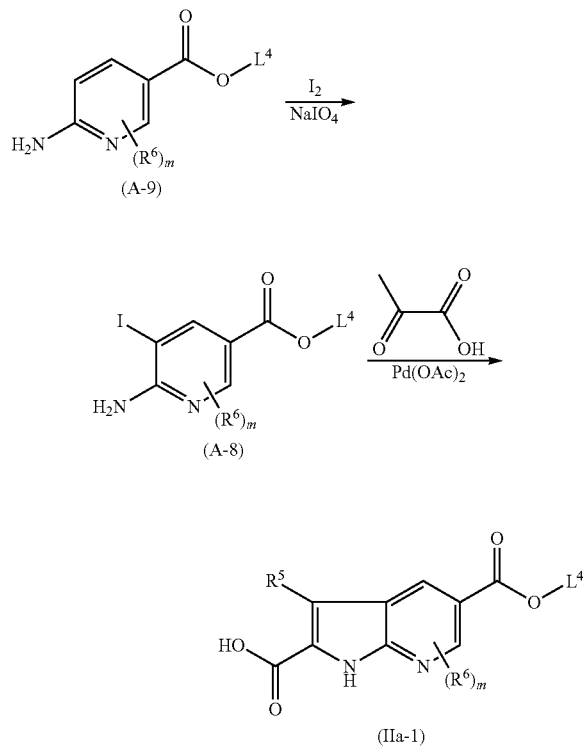

Compounds of the formula (IIa-1) are obtained here analogously to known processes from compounds of the formula (A-8) by reaction with pyruvic acid in the presence of a palladium catalyst, for example palladium acetate (cf., for example, Bioorganic & Medicinal Chemistry Letters, 20(9), 2010, 2722-2725), to obtain compounds (IIa-1, $R^5$=H) which can optionally be converted by reaction with a halogenating reagent, for example chloro- or bromosuccinimide, into compounds (IIa-1) where $R^5$=Hal (cf., for example, WO-A-2009/023179). Compounds of the formula (A-8) can be obtained by iodination from anilines of the formula (A-9) by known processes (cf., for example, Bioorganic & Medicinal Chemistry Letters, 20(9), 2010, 2722-2725). Anilines of the formula (A-9) are commercially available or can be obtained by known processes (cf., for example, US 20080019915).

Indolecarboxylic acids of the formula (IIa-2) can be obtained, for example, according to Scheme 2.

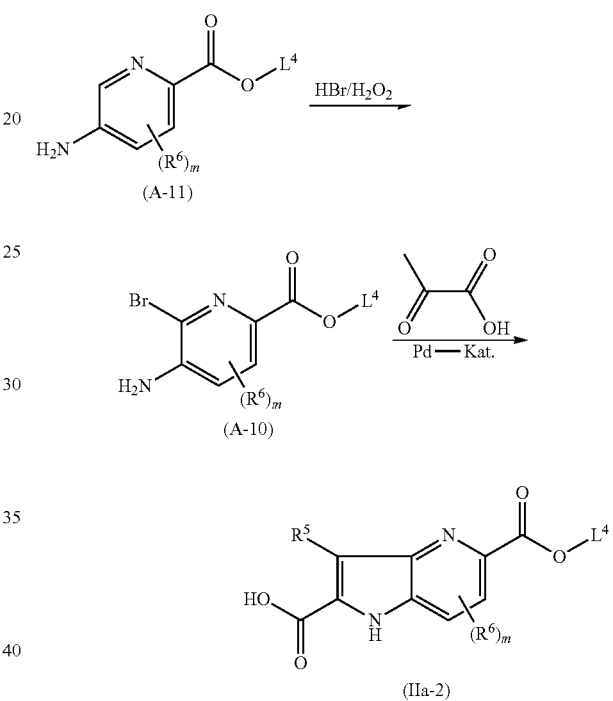

Here, aminopyridinecarboxylic esters of the formula (A-11) are initially alpha-brominated using $HBr/H_2O_2$, and the resulting compounds of the formula (A-10) are then converted by reaction with pyruvic acid in the presence of a palladium catalyst into the 1H-pyrrolo[3,2-b]pyridine-2-carboxylic acids. These two reactions are carried out analogously to known processes (cf., for example, EP 1479680 pages 48 and 49, and also Bioorganic and Medicinal Chemistry Letters, 20(9), 2010, 2722-2725). The resulting compounds (IIa-2, $R^5$=H) can optionally be converted by reaction with a halogenating agent such as, for example, chloro- or bromosuccinimide into compounds (IIa-2) where $R^5$=Hal (cf., for example, WO-A-2009/023179).

Carbonyl halides, more preferably carbonyl chlorides, as likewise represented by the general structures (II) ($L^1$=halogen), can be prepared by the reaction of a carboxylic acid (L=OH) with halogenating reagents such as thionyl chloride, thionyl bromide, phosphoryl chloride, oxalyl chloride, phosphorus trichloride, etc. [Houben-Weyl, 1952, vol. VIII, p. 463 ff.].

Indolecarboxylic acids of the formulae (IIc-1) and (IIb-1) can be obtained, for example, according to Scheme 3.

Scheme 3

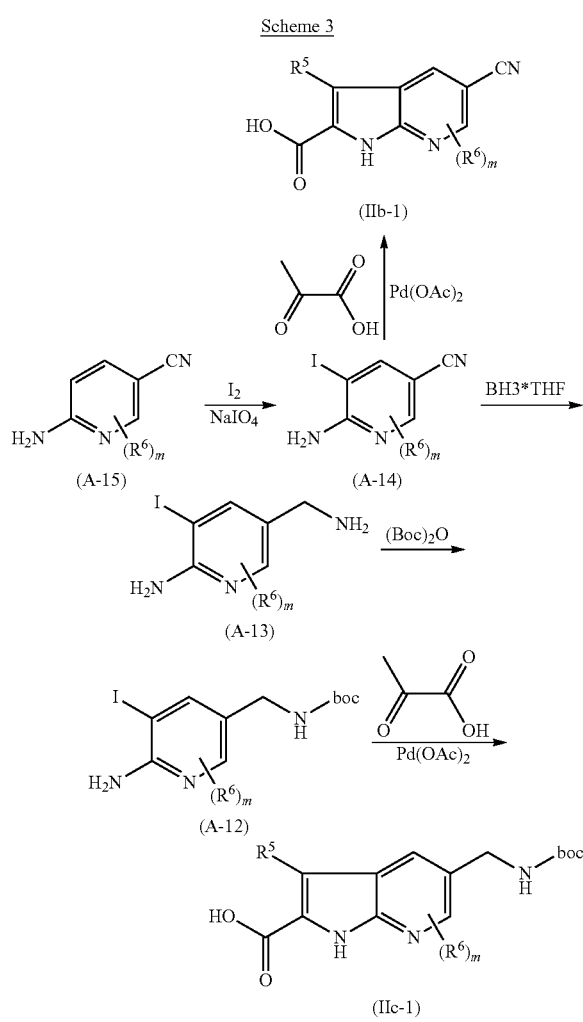

Compounds of the formula (IIc-1) are obtained here analogously to known processes from compounds of the formula (A-12) by reaction with pyruvic acid in the presence of a palladium catalyst, for example palladium acetate (cf., for example, Bioorganic & Medicinal Chemistry Letters, 20(9), 2010, 2722-2725), to obtain compounds (IIc-1, $R^5$=H) which can optionally be converted by reaction with a halogenating reagent, for example chloro- or bromosuccinimide, into compounds (IIc-1) where $R^5$=Hal (cf., for example, WO-A-2009/023179). Compounds of the formula (A-12) can be obtained by reacting amino compounds of the general formula (A-13) with di-tert-butyl dicarbonate according to generally known processes (cf., for example, Protective Groups in Organic Synthesis, Chapter 7, T. W. Greene, P.G.M. Wuts, ed., Wiley, 2006). Amino compounds of the general formula (A-13) can be obtained by generally known processes by reacting nitriles of the general formula (A-14) with a suitable reducing agent such as, for example, borane (cf., for example, March's Advanced Organic Chemistry, chapter 19, Wiley, 2007). Iodo compounds of the general formula (A-14) can be obtained by iodination from anilines of the formula (A-15) by known processes (cf., for example, Bioorganic & Medicinal Chemistry Letters, 20(9), 2010, 2722-2725) Anilines of the formula (A-15) are commercially available or can be obtained by known processes (cf., for example, US 20040077605).

Compounds of the formula (IIb-1, $R^5$=H) can be obtained analogously to the process described above from compounds of the formula (A-14) by reaction with pyruvic acid in the presence of a palladium catalyst such as, for example, palladium acetate.

Haloalkyl-substituted amines of the general formula (III) are commercially available or known from the literature, or can be synthesized by processes known from the literature. For example, aryl halides can be reacted in the presence of magnesium in a Grignard reaction with haloalkyl carboxylates. The ketones thus formed can then be converted by a reductive amination to the corresponding amines (cf. DE-A-2723464).

Novel haloalkyl-substituted amines of the general formula (III; $R_2$=H, $R_3$=H, $C_1$-$C_4$-alkyl) can be obtained, for example, according to Scheme 4, Scheme 4

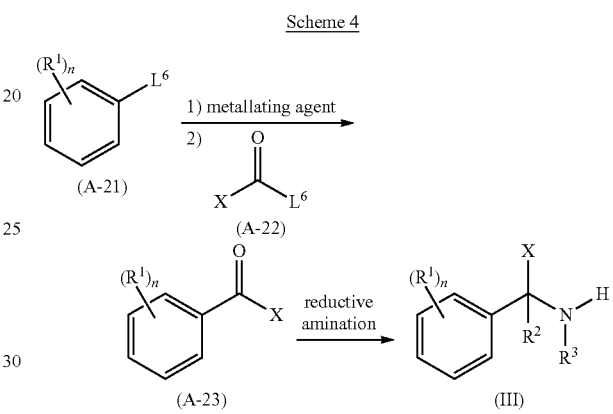

where
$L^6$ is —$C_1$-$C_4$-alkoxy or —N($CH_3$)—O—$C_1$-$C_4$-alkyl, by reacting compounds of the formula (A-21) which are commercially available or known from the literature first with a metallating reagent, for example n-butyllithium, to give an organometallic intermediate, which is then reacted with a compound of the formula (A-22) to obtain ketones of the formula (A-23). These can then be converted in analogy to commonly known procedures by reductive amination to amines of the formula (III) (cf., for example, WO2011054436 or Tetrahedron, 65(47), 9807-9813; 2009).

Compounds of the formulae (A-21), (A-22), (V), (VII), (VIII) are substances known from the literature or are commercially available.

The processes according to the invention for preparation of the novel compounds of the formula (I) are preferably performed using a diluent. Useful diluents for performance of the processes according to the invention are, as well as water, all inert solvents. Examples which may be mentioned are: halohydrocarbons (e.g. chlorohydrocarbons such as tetrachloroethylene, tetrachloroethane, dichloropropane, methylene chloride, dichlorobutane, chloroform, carbon tetrachloride, trichloroethane, trichloroethylene, pentachloroethane, difluorobenzene, 1,2-dichloroethane, chlorobenzene, bromobenzene, dichlorobenzene, chlorotoluene, trichlorobenzene), alcohols (e.g. methanol, ethanol, isopropanol, butanol), ethers (e.g. ethyl propyl ether, methyl tert-butyl ether, anisole, phenetole, cyclohexyl methyl ether, dimethyl ether, diethyl ether, dipropyl ether, diisopropyl ether, di-n-butyl ether, diisobutyl ether, diisoamyl ether, ethylene glycol dimethyl ether, tetrahydrofuran, 1,4-dioxane, dichlorodiethyl ether and polyethers of ethylene oxide and/or propylene oxide), amines (e.g. trimethyl-, triethyl-, tripropyl-, tributylamine, N-methylmorpholine, pyridine and tetramethylenediamine), nitrohydrocarbons (e.g. nitromethane, nitroethane, nitropropane, nitrobenzene, chloronitrobenzene, o-nitrotoluene); nitriles (for example acetonitrile, propionitrile, butyronitrile, isobutyronitrile, benzonitrile, m-chlorobenzonitrile), tetrahydrothiophene dioxide, dimethyl sulphoxide, tetramethylene sulphoxide, dipropyl sulphoxide, benzyl methyl sulphoxide, diisobutyl sulphoxide, dibutyl sulphoxide, diisoamyl sulphoxide, sulphones (e.g. dimethyl, diethyl, dipropyl, dibutyl, diphenyl, dihexyl, methyl ethyl, ethyl propyl, ethyl isobutyl and pentamethylene sulphone), aliphatic, cycloaliphatic or aromatic hydrocarbons (e.g. pentane, hexane, heptane, octane, nonane and technical hydrocarbons), and also what are called "white spirits" with components having boiling points in the range from, for example, 40° C. to 250° C., cymene, petroleum fractions within a boiling range from 70° C. to 190° C., cyclohexane, methylcyclohexane, petroleum ether, ligroin, octane, benzene, toluene, chlorobenzene, bromobenzene, nitrobenzene, xylene, esters (e.g. methyl, ethyl, butyl and isobutyl acetate, dimethyl, dibutyl and ethylene carbonate); amides (e.g. hexamethylenephosphoramide, formamide, N-methylformamide, N,N-dimethylformamide, N,N-dipropylformamide, N,N-dibutylformamide, N-methylpyrrolidine, N-methylcaprolactam, 1,3-dimethyl-3,4,5,6-tetrahydro-2(1H)-pyrimidine, octylpyrrolidone, octylcaprolactam, 1,3-dimethyl-2-imidazolinedione, N-formylpiperidine, N,N'-diformylpiperazine) and ketones (e.g. acetone, acetophenone, methyl ethyl ketone, methyl butyl ketone).

It is of course also possible to perform the process according to the invention in mixtures of the solvents and diluents mentioned.

When performing the process according to the invention, the reaction temperatures can be varied within a relatively wide range. In general, the process is carried out at temperatures between −30° C. and +150° C., preferably between −10° C. and +100° C.

The process according to the invention is generally performed under atmospheric pressure. However, it is also possible to perform the process according to the invention under elevated or reduced pressure generally at absolute pressures between 0.1 bar and 15 bar.

To perform the process according to the invention, the starting materials are generally used in approximately equimolar amounts. However, it is also possible to use one of the components in a relatively large excess. The reaction is generally performed in a suitable diluent in the presence of a reaction auxiliary, optionally also under a protective gas atmosphere (for example under nitrogen, argon or helium) and the reaction mixture is generally stirred at the temperature required for several hours. The workup is performed by customary methods (cf. the Preparation Examples).

The basic reaction auxiliaries used to perform the processes according to the invention may be all suitable acid binders. Examples include: alkaline earth metal or alkali metal compounds (e.g. hydroxides, hydrides, oxides and carbonates of lithium, sodium, potassium, magnesium, calcium and barium), amidine bases or guanidine bases (e.g. 7-methyl-1,5,7-triazabicyclo[4.4.0]dec-5-ene (MTBD); diazabicyclo[4.3.0]nonene (DBN), diazabicyclo[2.2.2]octane (DABCO), 1,8-diazabicyclo[5.4.0]undecene (DBU), cyclohexyltetrabutylguanidine (CyTBG), cyclohexyltetramethylguanidine (CyTMG), N,N,N,N-tetramethyl-1,8-naphthalenediamine, pentamethylpiperidine) and amines, especially tertiary amines (e.g. triethylamine, trimethylamine, tribenzylamine, triisopropylamine, tributylamine, tricyclohexylamine, triamylamine, trihexylamine, N,N-dimethylaniline, N,N-dimethyltoluidine, N,N-dimethyl-p-aminopyridine, N-methylpyrrolidine, N-methylpiperidine, N-methylimidazole, N-methylpyrazole, N-methylmorpholine, N-methylhexamethylenimine, pyridine, 4-pyrrolidinopyridine, 4-dimethylaminopyridine, quinoline, α-picoline, β-picoline, isoquinoline, pyrimidine, acridine, N,N,N',N'-tetramethylenediamine, N,N,N',N'-tetraethylenediamine, quinoxaline, N-propyldiisopropylamine, N-ethyldiisopropylamine, N,N'-dimethylcyclohexylamine, 2,6-lutidine, 2,4-lutidine or triethylenediamine).

The acidic reaction auxiliaries used to perform the process according to the invention include all mineral acids (e.g. hydrohalic acids such as hydrofluoric acid, hydrochloric acid, hydrobromic acid or hydriodic acid, and also sulphuric acid, phosphoric acid, phosphorous acid, nitric acid), Lewis acids (e.g. aluminium(III) chloride, boron trifluoride or its etherate, titanium(IV) chloride, tin(IV) chloride) and organic acids (e.g. formic acid, acetic acid, propionic acid, malonic acid, lactic acid, oxalic acid, fumaric acid, adipic acid, stearic acid, tartaric acid, oleic acid, methanesulphonic acid, benzoic acid, benzenesulphonic acid or para-toluenesulphonic acid).

The preparation and use examples which follow illustrate the invention without limiting it.

PREPARATION EXAMPLES

In the examples which follow, RT means room temperature, i.e. 20° C., and the expression "1 eq" means 1 equivalent.

Synthesis Example No. 1

$N^5$-Cyclopropyl-1-ethyl-6-methyl-$N^2$-{2,2,2-trifluoro-1-[3-(trifluoromethyl)phenyl]ethyl}-1H-pyrrolo[2,3-b]pyridine-2,5-dicarboxamide Step 1: Methyl 6-amino-5-iodo-2-methylnicotinate

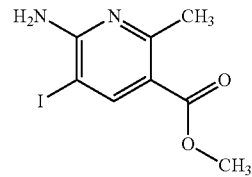

Sodium periodate (4.05 g, 18.9 mmol) and iodine (9.62 g, 37.9 mmol) were added to a solution of methyl 6-amino-2-methylnicotinate (8.40 g, 50.5 mmol) in DMF (45 ml), and the mixture was then stirred at 50° C. for 1.5 hours. The reaction mixture was added to a cold solution of 250 ml of saturated sodium thiosulphate solution in 150 ml of water. The solid formed was filtered off with suction, washed with water and dried. This gave 13.4 mg (88.9% of theory) of methyl 6-amino-5-iodo-2-methylnicotinate. HPLC-MS: log P=1.55; mass (m/z): 293.0 (M+H)$^+$; $^1$H-NMR (D$_6$¬DMSO) 2.50 (s, 3H), 3.74 (s, 3H), 6.81 (br. s, 1H), 8.25 (s, 1H).

The following were obtained analogously:

Methyl 6-amino-2-chloro-5-iodonicotinate:

HPLC-MS: log P=1.94; mass (m/z): 312.9 (M+H)$^+$; $^1$H-NMR (CD$_3$CN) 3.75 (s, 3H), 7.2-7.4 (br. s, 1H), 8.30 (s, 1H).

Ethyl 6-amino-5-iodo-2-trifluoromethylnicotinate:

From ethyl 6-amino-2-trifluoromethylnicotinate (CAS-Reg. No. 1227579-30-7; obtainable from ethyl 6-chloro-2-trifluoromethylnicotinate by reaction with ammonia)

HPLC-MS: log P=2.84; mass (m/z): 360.9 (M+H)+; 1H-NMR (D6-DMSO) 1.28 (t, 3H), 4.24 (q, 2H), 7.2-7.4 (br. s, 1H), 8.33 (s, 1H).

Step 2: 5-(Methoxycarbonyl)-6-methyl-1H-pyrrolo[2,3-b]pyridine-2-carboxylic acid

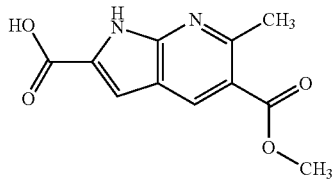 [SMILES: COC(=O)c1cc2cc(C(=O)O)[nH]c2nc1C]

Under argon, pyruvic acid (6.90 ml, 100.1 mmol) and 1,4-diazabicyclo[2.2.2]octane (11.2 g, 100.1 mmol) were added to a solution of methyl 6-amino-5-iodo-2-methylnicotinate (9.00 g, 30.8 mmol) in N,N-dimethylformamide (88 ml), and the flask was evacuated and flushed with argon. Argon was subsequently passed through the solution for 5 min, palladium(II) acetate (0.345 g, 1.54 mmol) was then added and the mixture was heated at 100° C. for 2 h. The cooled solution was filtered through Celite and the dimethylformamide was distilled off. The residue was then taken up in water and acidified with hydrochloric acid, giving a solid (6.3 g, 86% of theory). HPLC-MS: log P=1.26; mass (m/z): 235.0 (M+H)+; 1H-NMR (DMSO) 2.79 (s, 3H), 3.85 (s, 3H), 7.19 (s, 1H), 8.62 (s, 1H), 12.50 (s, 1H).

The following were obtained analogously:
6-Chloro-5-(methoxycarbonyl)-1H-pyrrolo[2,3-b]pyridine-2-carboxylic acid:
HPLC-MS: log P=1.37; mass (m/z): 255.0 (M+H)+; 1H-NMR (DMSO) 3.86 (s, 3H), 6.92 (s, 1H), 8.56 (s, 1H), 12.50 (s, 1H).
5-(Ethoxycarbonyl)-6-trifluoromethyl-1H-pyrrolo[2,3-b]pyridine-2-carboxylic acid:
HPLC-MS: log P=2.06; mass (m/z): 303.0 (M+H)+; 1H-NMR (DMSO) 1.32 (s, 3H), 4.30 (q, 2H), 7.33 (s, 1H), 8.69 (s, 1H), 13.20 (s, 1H).

Step 3: Methyl 6-methyl-2-({2,2,2-trifluoro-1-[3-(trifluoromethyl)phenyl]ethyl}carbamoyl)-1H-pyrrolo[2,3-b]pyridine-5-carboxylate

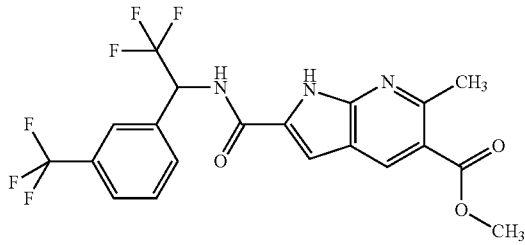 [SMILES: COC(=O)c1cc2cc(C(=O)NC(c3cccc(C(F)(F)F)c3)C(F)(F)F)[nH]c2nc1C]

2,2,2-Trifluoro-1-[3-fluoro-3-(trifluoromethyl)phenyl]ethanamine (2.07 g, 8.54 mmol) was dissolved in N,N-dimethylformamide (6 ml), and 5-(methoxycarbonyl)-6-methyl-1H-pyrrolo[2,3-b]pyridine-2-carboxylic acid (1.60 g, 6.83 mmol), N-[(1H-benzotriazol-1-yloxy)(dimethylamino)methylene]-N-methylmethanaminium hexafluorophosphate (2.56 g, 6.83 mmol) and 4-methylmorpholine (2.53 ml, 20.50 mmol) were added. The reaction mixture was stirred at room temperature for 16 h and then water was added. The aqueous phase was extracted three times with ethyl acetate and the extract was dried over sodium sulphate, adsorbed on silica gel and chromatographed with ethyl acetate. This gave 1.74 g (55% of theory) of methyl 6-methyl-2-({2,2,2-trifluoro-1-[3-(trifluoromethyl)phenyl]ethyl}carbamoyl)-1H-pyrrolo[2,3-b]pyridine-5-carboxylate. HPLC-MS: log P=3.37; mass (m/z): 460.1 (M+H)+; 1H-NMR (D6-DMSO): δ 2.79 (s, 3H), 3.87 (s, 2H), 6.29-6.32 (m, 1H), 7.50 (s, 1H), 7.70-7.74 (m, 1H), 7.82-7.84 (m, 1H), 8.05 (d, 1H), 8.18 (s, 1H), 8.66 (m, 1H), 9.72-9.74 (m, 1H).

The following, for example, were obtained analogously:
Methyl 6-chloro-2-({2,2,2-trifluoro-1-[3-(trifluoromethyl)phenyl]ethyl}carbamoyl)-1H-pyrrolo[2,3-b]pyridine-5-carboxylate
HPLC-MS: log P=3.48; mass (m/z): 480.0 (M+H)+; 1HNMR (D6-DMSO): 3.89 (s, 2H), 6.29-6.32 (m, 1H), 7.60 (s, 1H), 7.70-7.74 (m, 1H), 7.81-7.84 (m, 1H), 8.05 (d, 1H), 8.19 (s, 1H), 8.74 (s, 1H), 9.78 (m, 1H).
Ethyl 2-{[1-(3,5-dichloro-4-fluorophenyl)-2,2,2-trifluoroethyl]carbamoyl}-6-(trifluoromethyl)-1H-pyrrolo[2,3-b]pyridine-5-carboxylate
HPLC-MS: log P=4.50; mass (m/z): 545.9 (M+H)+; 1HNMR (D6-DMSO): 1.35 (t, 3H), 4.38 (q, 2H), 6.29-6.32 (m, 1H), 7.65 (s, 1H), 8.10 (d, 2H), 8.76 (s, 1H), 9.75 (m, 1H).

Step 4: Methyl 1-ethyl-6-methyl-2-({2,2,2-trifluoro-1-[3-(trifluoromethyl)phenyl]ethyl}carbamoyl)-1H-pyrrolo[2,3-b]pyridine-5-carboxylate

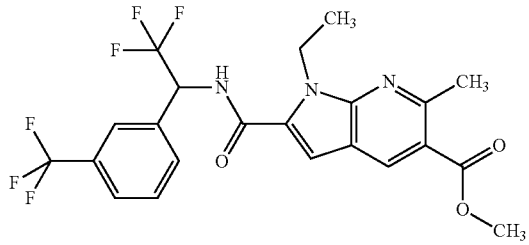 [SMILES: CCn1c(C(=O)NC(c2cccc(C(F)(F)F)c2)C(F)(F)F)cc2cc(C(=O)OC)c(C)nc21]

Methyl 6-methyl-2-({2,2,2-trifluoro-1-[3-(trifluoromethyl)phenyl]ethyl}carbamoyl)-1H-pyrrolo[2,3-b]pyridine-5-carboxylate (1.58 g, 3.44 mmol) was dissolved under argon at 0° C. in N,N-dimethylformamide (35 ml). Sodium hydride (60%; 0.165 g, 4.12 mmol) was added and the mixture was stirred with ice cooling for 2 h. Iodoethane (0.643 g, 4.12 mmol) was added and the reaction mixture was thawed with stirring over 18 h. Water and ethyl acetate were added and the phases were separated. The organic phase was washed with saturated sodium chloride solution and dried over magnesium sulphate, and the solvent was removed under reduced pressure. The residue was chromatographed with cyclohexane/ethyl acetate (3/1) and gave 1.15 g (66% of theory) of methyl 1-ethyl-6-methyl-2-({2,2,2-trifluoro-1-[3-(trifluoromethyl)phenyl]ethyl}carbamoyl)-1H-pyrrolo[2,3-b]pyridine-5-carboxylate. HPLC-MS: log P=6.27; mass (m/z): 488.1 (M+H)+; 1HNMR (D6-DMSO): δ 1.20 (t, 3H), 2.83 (s, 3H), 3.87 (s, 3H), 4.59 (q, 2H), 6.30-6.34 (m, 1H), 7.42 (s, 1H), 7.70-7.84 (m, 2H), 8.06 (d, 1H), 7.93-7.97 (m, 1H), 8.21 (s, 1H), 8.67 (s, 1H).

The following, for example, were obtained analogously:
Methyl 1-ethyl-6-chloro-2-({2,2,2-trifluoro-1-[3-(trifluoromethyl)phenyl]ethyl}carbamoyl)-1H-pyrrolo[2,3-b]pyridine-5-carboxylate HPLC-MS: log P=4.61; mass (m/z): 508.1 (M+H)+; 1HNMR (D6-DMSO): δ 1.25 (t, 3H), 3.90 (s, 3H), 4.50 (q, 2H), 6.31-6.34 (m, 1H), 7.49 (s, 1H), 7.70-7.84 (m, 2H), 8.06 (d, 1H), 8.30 (s, 1H), 8.20 (s, 1H), 8.76 (s, 1H).

Ethyl 2-{[1-(3,5-dichloro-4-fluorophenyl)-2,2,2-trifluoroethyl]carbamoyl}-1-(prop-2-yn-1-yl)-6-(trifluoromethyl)-1H-pyrrolo[2,3-b]pyridine-5-carboxylate HPLC-MS: log P=5.19; mass (m/z): 584.0 (M+H)+

Methyl 2-{[1-(3-chloro-4-fluorophenyl)-2,2,2-trifluoroethyl]carbamoyl}-1-ethyl-6-methyl-1H-pyrrolo[2,3-b]pyridine-5-carboxylate HPLC-MS: log P=4.67; mass (m/z): 472.1 (M+H)+

Ethyl 6-chloro-2-{[1-(3,5-dichloro-2,4-difluorophenyl)-2,2,2-trifluoroethyl]carbamoyl}-1-ethyl-1H-pyrrolo[2,3-b]pyridine-5-carboxylate HPLC-MS: log P=5.64; mass (m/z): 559.3 (M+H)+

Ethyl 6-chloro-2-{[1-(3-chloro-4-fluorophenyl)-2,2,2-trifluoroethyl]carbamoyl}-1-ethyl-1H-pyrrolo[2,3-b]pyridine-5-carboxylate HPLC-MS: log P=4.86; mass (m/z): 507.1 (M+H)+

Ethyl 6-chloro-2-{[1-(3,5-dichloro-4-fluorophenyl)-2,2,2-trifluoroethyl]carbamoyl}-1-ethyl-1H-pyrrolo[2,3-b]pyridine-5-carboxylate HPLC-MS: log P=5.57; mass (m/z): 541.2 (M+H)+

Ethyl 6-chloro-1-(prop-2-yn-1-yl)-2-([2,2,2-trifluoro-1-[3-(trifluoromethyl)phenyl]ethyl]carbamoyl)-1H-pyrrolo[2,3-b]pyridine-5-carboxylate HPLC-MS: log P=4.48; mass (m/z): 532.3 (M+H)+

Ethyl 6-chloro-1-ethyl-2-({2,2,2-trifluoro-1-[4-fluoro-3-(trifluoromethyl)phenyl]ethyl}carbamoyl)-1H-pyrrolo[2,3-b]pyridine-5-carboxylate HPLC-MS: log P=5.01; mass (m/z): 540.3 (M+H)+

Ethyl 6-chloro-2-{[1-(3,4-dichlorophenyl)-2,2,2-trifluoroethyl]carbamoyl}-1-ethyl-1H-pyrrolo[2,3-b]pyridine-5-carboxylate HPLC-MS: log P=5.35; mass (m/z): 523.1 (M+H)+

Ethyl 6-chloro-2-{[1-(3,5-dichloro-2,4-difluorophenyl)-2,2,2-trifluoroethyl]carbamoyl}-1-(prop-2-yn-1-yl)-1H-pyrrolo[2,3-b]pyridine-5-carboxylate HPLC-MS: log P=5.16; mass (m/z): 569.1 (M+H)+

Ethyl 6-chloro-1-(prop-2-yn-1-yl)-2-({2,2,2-trifluoro-1-[4-fluoro-3-(trifluoromethyl)phenyl]ethyl}carbamoyl)-1H-pyrrolo[2,3-b]pyridine-5-carboxylate HPLC-MS: log P=4.59; mass (m/z): 550.1 (M+H)+

Methyl 2-{[1-(3,5-dichloro-4-fluorophenyl)-2,2,2-trifluoroethyl]carbamoyl}-1-ethyl-6-methyl-1H-pyrrolo[2,3-b]pyridine-5-carboxylate HPLC-MS: log P=5.35; mass (m/z): 507.1 (M+H)+

Methyl 2-{[1-(3,5-dichloro-2,4-difluorophenyl)-2,2,2-trifluoroethyl]carbamoyl}-1-ethyl-6-methyl-1H-pyrrolo[2,3-b]pyridine-5-carboxylate HPLC-MS: log P=5.60; mass (m/z): 525.1 (M+H)+

Methyl 6-methyl-1-(prop-2-yn-1-yl)-2-({2,2,2-trifluoro-1-[3-(trifluoromethyl)phenyl]ethyl}carbamoyl)-1H-pyrrolo[2,3-b]pyridine-5-carboxylate HPLC-MS: log P=4.31; mass (m/z): 498.2 (M+H)+

Ethyl 6-chloro-2-{[1-(3,5-dichloro-4-fluorophenyl)-2,2,2-trifluoroethyl]carbamoyl}-1-(prop-2-yn-1-yl)-1H-pyrrolo[2,3-b]pyridine-5-carboxylate HPLC-MS: log P=4.98; mass (m/z): 551.2 (M+H)+

Methyl 2-{[1-(3,5-dichlorophenyl)-2,2,2-trifluoroethyl]carbamoyl}-1-ethyl-6-methyl-1H-pyrrolo[2,3-b]pyridine-5-carboxylate HPLC-MS: log P=5.33; mass (m/z): 489.1 (M+H)±

Methyl 1-ethyl-6-methyl-2-({2,2,2-trifluoro-1-[4-fluoro-3-(trifluoromethyl)phenyl]ethyl}carbamoyl)-1H-pyrrolo[2,3-b]pyridine-5-carboxylate HPLC-MS: log P=4.81; mass (m/z): 506.1 (M+H)+

Ethyl 2-{[1-(3,5-dichloro-2,4-difluorophenyl)-2,2,2-trifluoroethyl]carbamoyl}-1-ethyl-6-(trifluoromethyl)-1H-pyrrolo[2,3-b]pyridine-5-carboxylate HPLC-MS: log P=6.01; mass (m/z): 593.1 (M+H)+

Ethyl 6-chloro-2-{1-[4-chloro-3-(trifluoromethyl)phenyl]-2,2,2-trifluoroethyl}carbamoyl)-1-ethyl-1H-pyrrolo[2,3-b]pyridine-5-carboxylate HPLC-MS: log P=5.35; mass (m/z): 557.2 (M+H)+

Methyl 2-({1-[4-chloro-3-(trifluoromethyl)phenyl]-2,2,2-trifluoroethyl}carbamoyl)-1-ethyl-6-methyl-1H-pyrrolo[2,3-b]pyridine-5-carboxylate HPLC-MS: log P=5.18; mass (m/z): 523.1 (M+H)+

Ethyl 2-{[1-(3,5-dichloro-4-fluorophenyl)-2,2,2-trifluoroethyl]carbamoyl}-1-(prop-2-yn-1-yl)-6-(trifluoromethyl)-1H-pyrrolo[2,3-b]pyridine-5-carboxylate HPLC-MS: log P=5.19; mass (m/z): 585.2 (M+H)+

Step 5: 1-Ethyl-6-methyl-24 {2,2,2-trifluoro-1-[3-(trifluoromethyl)phenyl]ethyl}carbamoyl)-1H-pyrrolo[2,3-b]pyridine-5-carboxylic acid

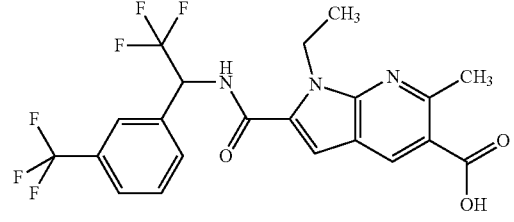 [SMILES: CCn1c(C(=O)NC(c2cccc(C(F)(F)F)c2)C(F)(F)F)cc2cc(C(=O)O)c(C)nc21]

Methyl 1-ethyl-6-methyl-24 {2,2,2-trifluoro-1-[3-(trifluoromethyl)phenyl]ethyl}carbamoyl)-1H-pyrrolo[2,3-b]pyridine-5-carboxylate (1.10 g, 2.25 mmol) was dissolved in dichloromethane (25 ml), and a solution of boron tribromide (11.28 ml, 11.28 mmol) in dichloromethane (10 ml) was added dropwise at −10° C. The reaction mixture was stirred at −10° C. for 1 h and then at room temperature for 2 h. Water was added and the precipitated solid was filtered off with suction and dried. This gave 0.950 mg (59% of theory) of 1-ethyl-6-methyl-24 {2,2,2-trifluoro-1-[3-(trifluoromethyl)phenyl]ethyl}carbamoyl)-1H-pyrrolo[2,3-b]pyridine-5-carboxylic acid, which was reacted further without purification. HPLC-MS: log P=3.61; mass (m/z): 474.1 (M+H)+; 1HNMR (D6-DMSO): δ 1.22 (t, 3H), 2.83 (s, 3H), 4.60 (q, 2H), 6.29-6.35 (m, 1H), 7.41 (s, 1H), 7.70-7.84 (m, 2H), 8.04 (d, 1H), 8.21 (s, 1H), 8.66 (s, 1H), 9.90 (d, 1H).

The following, for example, were obtained analogously:
6-Chloro-1-ethyl-2-({2,2,2-trifluoro-1-[3-(trifluoromethyl)phenyl]ethyl}carbamoyl)-1H-pyrrolo[2,3-b.]pyridine-5-carboxylic acid HPLC-MS: log P=3.63; mass (m/z): 494.0 (M+H)+; 1HNMR (D6-DMSO): δ 1.27 (t, 3H), 4.54 (q, 2H), 6.29-6.35 (m, 1H), 7.48 (s, 1H), 7.70-7.84 (m, 2H), 8.06 (d, 1H), 8.21 (s, 1H), 8.73 (s, 1H), 9.90 (d, 1H).

Step 6: $N^5$-Cyclopropyl-1-ethyl-6-methyl-$N^2$-{2,2,2-trifluoro-1-[3-(trifluoromethyl)phenyl]ethyl}-1H-pyrrolo[2,3-b]pyridine-2,5-dicarboxamide

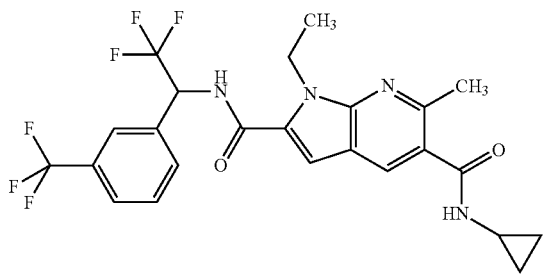 [SMILES: CCn1c(C(=O)NC(c2cccc(C(F)(F)F)c2)C(F)(F)F)cc2cc(C(=O)NC3CC3)c(C)nc21]

Cyclopropylamine (0.0217 g, 0.380 mmol) was dissolved in N,N-dimethylformamide (2.3 ml) and 1-ethyl-6-methyl-2-({2,2,2-trifluoro-1-[3-(trifluoromethyl)phenyl]ethyl}carbamoyl)-1H-pyrrolo[2,3-b]pyridine-5-carboxylic acid (0.150 g, 0.317 mmol), N-[(1H-benzotriazol-1-yloxy)(dimethylamino)methylene]-N-methylmethanaminium hexafluorophosphate (0.120 g, 0.317 mmol) and 4-methylmorpholine (0.105 ml, 0.951 mmol) were added. The reaction mixture was stirred at room temperature for 16 h and then water was added. The aqueous phase was extracted three times with ethyl acetate, dried over sodium sulphate, adsorbed on silica gel and chromatographed with cyclohexane/ethyl acetate (1:1). This gave 0.033 mg (18% of theory) of $N^5$-cyclopropyl-1-ethyl-6-methyl-$N^2$-{2,2,2-trifluoro-1-[3-(trifluoromethyl)phenyl]ethyl}-1H-pyrrolo[2,3-b]pyridine-2,5-dicarboxamide. HPLC-MS: log P=3.52; mass (m/z): 513.1 (M+H)+; $^1$HNMR (D$_6$-DMSO): δ 0.57 (m, 2H), 0.71 (m, 2H), 1.20 (t, 3H), 2.89 (s, 3H), 3.32 (s, 3H), 4.02 (q, 1H), 4.59 (q, 2H), 6.29-6.33 (m, 1H), 7.35 (s, 1H), 7.70-7.83 (m, 2H), 7.95 (s, 1H), 8.06 (m, 1H), 8.21 (s, 1H), 8.41 (d, 1H), 9.78 (d, 1H).

Synthesis Example No. 2

$N^5$-Cyclopropyl-1-ethyl-$N^2$-{2,2,2-trifluoro-1-[4-fluoro-3-(trifluoromethyl)phenyl]ethyl}-1H-pyrrolo[3,2-b]pyridine-2,5-dicarboxamide Step 1: Methyl 5-amino-6-bromopyridine-2-carboxylate

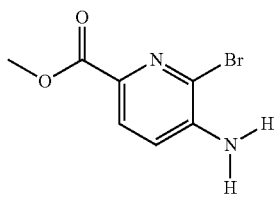

2.0 ml of hydrogen peroxide solution (32% strength) were added to methyl 5-aminopyridine-2-carboxylate (2.0 g, 13.15 mmol) and 30 ml of 48% strength hydrobromic acid, and the reaction was stirred at room temperature for two hours. Another 0.32 ml of hydrogen peroxide solution were then added, and the mixture was stirred for a further hour. The mixture was adjusted to pH 8 by addition of concentrated ammonia solution with ice cooling and extracted three times with in each case 60 ml of ethyl acetate. The organic phase was dried over sodium sulphate, concentrated on a rotary evaporator and chromatographed on silica gel (mobile phase: cyclohexane/ethyl acetate). This gave 1.32 g of the desired product (42.3% of theory).

HPLC-MS: log P=0.96; mass (m/z): 231.0; $^1$HNMR (D6-DMSO): δ 3.79 (s, 3H), 6.40 (broad, 2H), 7.1 (d, 1H), 7.8 (d, 1H).

The following were obtained analogously:
Ethyl 5-amino-6-bromo-3-chloropyridine-2-carboxylate
HPLC-MS: log P=1.91; mass (m/z): 279.0; 1HNMR (D6-DMSO): δ 1.27-1.30 (t, 3H), 4.24-4.28 (q, 2H), 6.55 (broad, 2H), 7.13 (s, 1H).

Step 2: 5-(Methoxycarbonyl)-1H-pyrrolo[3,2-b]pyridine-2-carboxylic acid

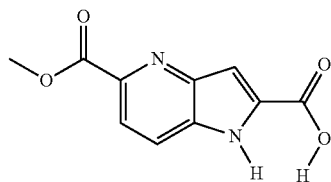 [SMILES: COC(=O)c1ccc2[nH]c(C(=O)O)cc2n1]

Methyl 5-aminopyridine-2-carboxylate (1.2 g, 5.2 mmol) and triphenylphosphine (1.5 g, 5.7 mmol) were initially charged in 10 ml of DMF, and pyruvic acid (1.83 g, 20.8 mmol), palladium(II) acetate (279 mg, 1.2 mmol) and triethylamine (2.6 g, 26 mmol) were added. The reaction mixture was stirred at a temperature of 100° C. for four hours, then cooled, concentrated on a rotary evaporator and taken up in ethyl acetate, water was added and the mixture was shaken. The aqueous phase was concentrated on a rotary evaporator and then triturated with a little cyclohexane. This gave 0.5 g (38% of theory) of 5-(methoxycarbonyl)-1H-pyrrolo[3,2-b]pyridine-2-carboxylic acid. HPLC-MS: log P=0.44; mass (m/z): 221.0 (M+H)+; $^1$HNMR (D6-DMSO): δ 3.89 (s, 3H), 7.20 (s, 1H), 7.90-7.98 (m, 2H), 10 (broad, 1H), 12.24 (s, 1H).

The following were obtained analogously:
6-Chloro-5-(ethoxycarbonyl)-1H-pyrrolo[3,2-b]pyridine-2-carboxylic acid
HPLC-MS: log P=1.43; mass (m/z): 269.0 (M+H)+; $^1$HNMR (D6-DMSO): δ 1.32-1.36 (t, 3H), 4.33-4.42 (q, 2H), 7.25 (s, 1H), 7.96 (s, 1H), 12.45 (s, 1H), 13.68 (s, 1H).

Step 3: Methyl 2-({2,2,2-trifluoro-1-[4-fluoro-3-(trifluoromethyl)phenyl]ethyl}carbamoyl)-1H-pyrrolo[3,2-b]pyridine-5-carboxylate

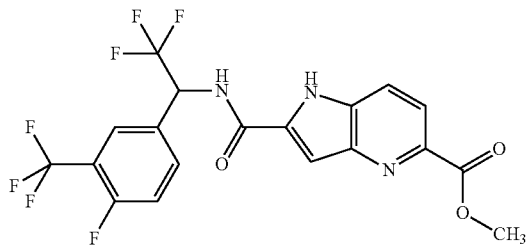 [SMILES: COC(=O)c1ccc2[nH]c(C(=O)NC(c3ccc(F)c(C(F)(F)F)c3)C(F)(F)F)cc2n1]

5-(Methoxycarbonyl)-1H-pyrrolo[3,2-b]pyridine-2-carboxylic acid (0.5 g, 2.27 mmol) was dissolved in eight ml of DMF, and 1-(4-fluoro-3-trifluoromethyl)-2,2,2-trifluoromethylamine (0.59 g, 2.27 mmol), HBTU (0.86 g, 2.27 mmol) and 4-methylmorpholine (0.69 g, 6.81 mmol) were added. The mixture was stirred under protective gas at room temperature for 18 hours, the volatile components were removed and the residue was taken up in ethyl acetate and washed with saturated sodium bicarbonate solution. The organic phase was dried over sodium sulphate and the solvent was removed under reduced pressure. The target product was then isolated by silica gel chromatography cyclohexane/ethyl acetate (0% ethyl acetate to 60%) (0.1 g, 8% of theory). HPLC-MS: log P=2.89; mass (m/z): 464.1 (M+H)$^+$; $^1$HNMR (D6-DMSO): δ 3.90 (s, 3H), 6.38-6.48 (m, 1H), 7.64-7.73 (m, 2H), 7.93-8.02 (m, 2H), 8.15-8.21 (m, 1H), 8.26-8.31 (m, 1H), 9.8 (s, 1H), 12.34 (s, 1H).

The following were obtained analogously:

Ethyl 6-chloro-2-({2,2,2-trifluoro-1-[4-fluoro-3-(trifluoromethyl)phenyl]ethyl}carbamoyl)-1H-pyrrolo[3,2-b]pyridine-5-carboxylate HPLC-MS: log P=3.62; mass (m/z): 512.1 (M+H)$^+$; $^1$HNMR (D6-DMSO): δ 1.31-1.39 (t, 3H), 4.36-4.43 (q, 2H), 6.36-6.49 (m, 1H), 7.62-7.71 (m, 2H), 7.98 (s, 1H), 8.12-8.20 (m, 1H), 8.25-8.30 (m, 1H), 9.80 (s, 1H), 12.38 (s, 1H).

Step 4: Methyl 1-ethyl-2-({2,2,2-trifluoro-1-[4-fluoro-3-(trifluoromethyl)phenyl]ethyl}carbamoyl)-1H-pyrrolo[3,2-b]pyridine-5-carboxylate

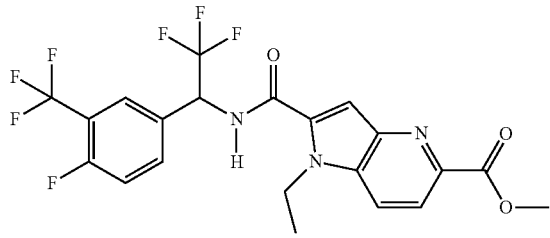 [SMILES: CCn1c(C(=O)NC(c2ccc(F)c(C(F)(F)F)c2)C(F)(F)F)cc2nc(C(=O)OC)ccc21]

Under argon protection, methyl 1-ethyl-2-({2,2,2-trifluoro-1-[4-fluoro-3-(trifluoromethyl)phenyl]ethyl}carbamoyl)-1H-pyrrolo[3,2-b]pyridine-5-carboxylate (150 mg, 0.32 mmol) was initially charged in DMF, and sodium hydride (11.39 mg, 0.29 mmol) was added at 0° C. The mixture was stirred at 0° C. for two hours, iodoethane (40.40 mg, 0.259 mmol) was then added dropwise and the mixture was stirred while the ice bath thawed to room temperature. After the reaction had ended (monitored by TLC), water was added, the mixture was extracted exhaustively with ethyl acetate, the organic phase was washed with sodium chloride solution, the volatile components were removed under reduced pressure and the residue was chromatographed on silica gel cyclohexane/ethyl acetate (0% ethyl acetate to 60%). This gave 9 mg (6% of theory) of the desired product. HPLC-MS: log P=3.66; mass (m/z): 492.1 (M+H)$^+$; $^1$HNMR (D6-DMSO): δ 1.20-1.30 (t, 3H), 3.91 (s, 3H), 4.61-4.68 (q, 2H), 6.33-6.44 (m, 1H), 7.47 (s, 1H), 7.64-7.71 (t, 1H), 8.00-8.03 (d, 1H), 8.12-8.21 (m, 1H), 8.22-8.24 (d, 1H), 8.27-8.30 (m, 1H), 9.95 (s, 1H).

Step 5: N$^5$-Cyclopropyl-1-ethyl-N$^2$-{2,2,2-trifluoro-1-[4-fluoro-3-(trifluoromethyl)phenyl]ethyl}-1H-pyrrolo[3,2-b]pyridine-2,5-dicarboxamide

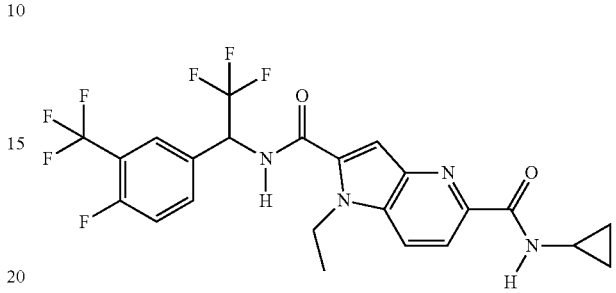

Under an atmosphere of argon protective gas, cyclopropylamine (58.1 mg, 1.02 mmol) was added to one ml of dichloromethane, and trimethylaluminium (73.4 mg, 1.02 mmol) was added dropwise using a syringe. The mixture was stirred for another 30 minutes, and methyl 1-ethyl-2-({2,2,2-trifluoro-1-[4-fluoro-3-(trifluoromethyl)phenyl]ethyl}carbamoyl)-1H-pyrrolo[3,2-b]pyridine-5-carboxylate, dissolved in one ml of dichloromethane, was then added dropwise. The reaction mixture was then heated under reflux for six hours and subsequently cooled and hydrolysed, and the residue was, after removal of the volatile components under reduced pressure, chromatographed on silica gel cyclohexane/ethyl acetate (ethyl acetate 0% to 60%). This gave 20 mg (35% of theory) of the target product. HPLC-MS: log P=3.78; mass (m/z): 517.1 (M+H)$^+$; $^1$HNMR (D6-DMSO): δ 0.54-0.76 (m, 4H), 1.22-1.30 (t, 3H), 2.88-2.94 (m, 1H), 4.48-4.59 (q, 2H), 6.32-6.42 (m, 1H), 7.42 (s, 1H), 7.65-7.71 (t, 1H), 7.98-8.02 (d, 1H), 8.14-8.20 (m, 1H), 8.20-8.24 (d, 1H), 8.26-8.32 (m, 1H), 8.56-8.62 (d, 1H), 9.91 (s, 1H).

Synthesis Example No. 3

5-(Acetamidomethyl)-1-ethyl-6-methyl-N-{2,2,2-trifluoro-1-[3-(trifluoromethyl)phenyl]ethyl}-1H-pyrrolo[2,3-b]pyridine-2-carboxamide Step 1: 6-Amino-5-iodo-2-methylnicotinonitrile

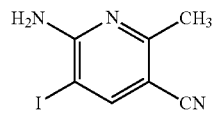

6-Amino-5-iodo-2-methylnicotinonitrile (3.30 g, 24.7 mmol) and silver sulphate (7.72 g, 24.7 mmol) were added to a solution of iodine (6.29 g, 24.7 mmol) in ethanol (120 ml), and the mixture was then stirred at 60° C. for 5 hours. The reaction mixture was filtered through kieselguhr, the filter cake was washed with ethanol and the filtrate was concentrated by 90% under reduced pressure. 20% strength sodium thiosulphate solution was added and the precipitate formed was filtered off with suction and water. Drying gave 2.70 mg (40.0% of theory) of 6-amino-5-iodo-2-methylnicotinonitrile. HPLC-MS: log P=1.55; mass (m/z): 259.9 (M+H)+; $^1$H-NMR (D$_6$¬DMSO) 2.38 (s, 3H), 7.0-7.1 (br. s, 1H), 8.18 (s, 1H).

Step 2:
5-(Aminomethyl)-3-iodo-6-methylpyridine-2-amine

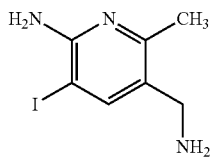

6-Amino-5-iodo-2-methylnicotinonitrile (3.70 g, 14.2 mmol) were initially charged in THF (45 ml), and 42.8 ml (42.8 mmol) of a 1 molar borane-THF complex solution in THF were added dropwise. The mixture was heated at reflux temperature for 3 hours and cooled, and 5 ml of a 2N HCl solution were cautiously added dropwise. The reaction mixture was heated under reflux for another hour and then allowed to cool for 15 hours while standing. The solvent was removed under reduced pressure and the residue was taken up in saturated sodium bicarbonate solution, which was subsequently extracted repeatedly with ethyl acetate. After drying over magnesium sulphate, the solvent was removed under reduced pressure, giving 2.50 g (60.0% of theory) of 5-(aminomethyl)-3-iodo-6-methylpyridine-2-amine, which was directly reacted further. HPLC-MS: log P=0.73; mass (m/z): 264.0

Step 3: tert-Butyl [(6-amino-5-iodo-2-methylpyridin-3-yl)methyl]carbamate

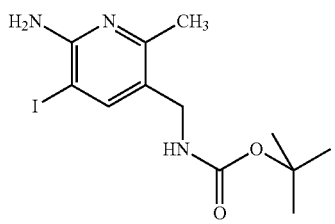 [SMILES: Cc1nc(N)c(I)cc1CNC(=O)OC(C)(C)C]

Triethylamine (1.49 g, 14.7 mmol) and 4-N,N-dimethylaminopyridine (180 mg, 1.47 mmol) were added to a solution of 5-(aminomethyl)-3-iodo-6-methylpyridine-2-amine (2.20 g, 7.35 mmol) in tetrahydrofuran (10 ml), and di-tert-butyl dicarbonate (2.40 g, 11.0 mmol) dissolved in tetrahydrofuran (33 ml) was then added dropwise. The mixture was stirred at room temperature for 2 hours, the solvent was then removed under reduced pressure amd the residue was chromatographed (Chromabond Flash RS 40 SiOH; mobile phase: cyclohexane/ethyl acetate 1/1). This gave 865 mg (32% of theory). HPLC-MS: log P=1.19; mass (m/z): 364.0 (M+H)+; $^1$H-NMR (DMSO) 1.38 (s, 9H), 2.22 (s, 3H), 3.92 (m, 2H), 5.84 (s, 1H), 7.22 (s, 1H), 7.61 (s, 1H).

Step 4: 5-{[(tert-Butoxycarbonyl)amino]methyl}-6-methyl-1H-pyrrolo[2,3-b]pyridine-2-carboxylic acid

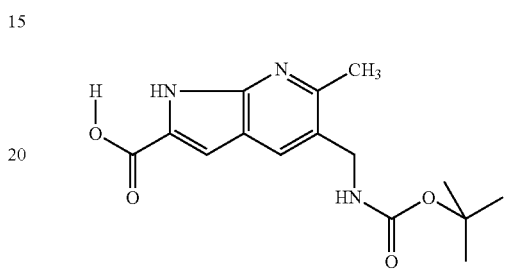

Under argon, pyruvic acid (6.90 ml, 100.1 mmol) and 1,4-diazabicyclo[2.2.2]octane (843 g, 7.51 mmol) were added to a solution of tert-butyl [(6-amino-5-iodo-2-methylpyridin-3-yl)methyl]carbamate (840 mg, 2.31 mmol) in N,N-dimethylformamide (0.5 ml), and the flask was evacuated and flushed with argon. Then argon was passed through the solution for 5 min and then palladium(II) acetate (25.9 mg, 0.11 mmol) was added and the mixture was heated to 100° C. for 2 h. The cooled solution was filtered through Celite and the dimethylformamide was distilled off. The residue was then taken up in water and acidified with hydrochloric acid, giving a 5-{[(tert-butoxycarbonyl)amino]methyl}-6-methyl-1H-pyrrolo[2,3-b]pyridine-2-carboxylic acid (650 g, 88% of theory). HPLC-MS: log P=0.58; mass (m/z): 306.1 (M+H)+; $^1$H-NMR (DMSO) 1.37 (s, 9H), 2.33 (s, 3H), 4.17 (d, 2H), 6.57 (s, 1H), 7.68 (s, 1H).

Step 5: tert-Butyl {[6-methyl-2-({2,2,2-trifluoro-1-[3-(trifluoromethyl)phenyl]ethyl}carbamoyl)-1H-pyrrolo[2,3-b]pyridin-5-yl]methyl}carbamate

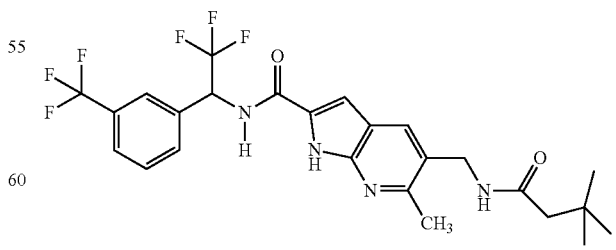

2,2,2-Trifluoro-1-[3-fluoro-3-(trifluoromethyl)phenyl]ethanamine (726 mg, 2.98 mmol) was dissolved in N,N-dimethylformamide (10 ml), and 5-{[(tert-butoxycarbonyl)

amino]methyl}-6-methyl-1H-pyrrolo[2,3-b]pyridine-2-carboxylic acid (730 g, 2.39 mmol), N-[(1H-benzotriazol-1-yloxy)(dimethylamino)methylene]-N-methylmethanaminium hexafluorophosphate (907 mg, 2.39 mmol) and 4-methylmorpholine (725 mg, 7.17 mmol) were added. The reaction mixture was stirred at room temperature for 16 h and then water was added. The aqueous phase was extracted three times with ethyl acetate and the extract was dried over sodium sulphate, adsorbed on silica gel and chromatographed with ethyl acetate. 420 mg (33% of theory) of tert-butyl {[6-methyl-2-({2,2,2-trifluoro-1-[3-(trifluoromethyl)phenyl]ethyl}carbamoyl)-1H-pyrrolo[2,3-b]pyridin-5-yl]methyl}carbamate were obtained. HPLC-MS: log P=3.49; mass (m/z): 531.2 (M+H)+; 1HNMR (D6-DMSO): δ 1.40 (s, 9H), 3.30 (s, 3H), 4.20 (m, 2H), 6.29-6.32 (m, 1H), 7.35 (s, 1H), 7.71 (m, 1H), 7.82-7.84 (m, 1H), 8.03 (d, 1H), 8.17 (s, 1H), 9.43 (m, 1H).

Step 6: tert-Butyl {[1-ethyl-6-methyl-2-({2,2,2-trifluoro-1-[3-(trifluoromethyl)phenyl]ethyl}carbamoyl)-1H-pyrrolo[2,3-b]pyridin-5-yl]methyl}carbamate

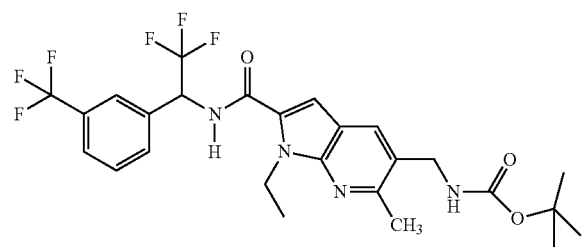 [SMILES: CCn1c(C(=O)NC(c2cccc(C(F)(F)F)c2)C(F)(F)F)cc2cc(CNC(=O)OC(C)(C)C)c(C)nc21]

tert-Butyl {[6-methyl-2-({2,2,2-trifluoro-1-[3-(trifluoromethyl)phenyl]ethyl}carbamoyl)-1H-pyrrolo[2,3-b]pyridin-5-yl]methyl}carbamate (410 g, 0.77 mmol) was dissolved under argon at 0° C. in N,N-dimethylformamide (7.9 ml). Sodium hydride (60%; 37 mg, 0.92 mmol) was added and the mixture was stirred with ice cooling for 2 h. Iodoethane (145 g, 0.92 mmol) was added and the reaction mixture was thawed with stirring over 18 h. Water and ethyl acetate were added and the phases were separated. The organic phase was washed with saturated sodium chloride solution and dried over magnesium sulphate, and the solvent was removed under reduced pressure. The residue was chromatographed with cyclohexane/ethyl acetate (3/1) and gave 300 g (68% of theory) of tert-butyl a {[1-ethyl-6-methyl-2-({2,2,2-trifluoro-1-[3-(trifluoromethyl)phenyl]ethyl}carbamoyl)-1H-pyrrolo[2,3-b]pyridin-5-yl]methyl}carbamate. HPLC-MS: log P=4.67; mass (m/z): 559.2 (M+H)+; 1HNMR (D6-DMSO): δ 1.21 (t, 2H), 1.40 (s, 9H), 3.32 (s, 3H), 4.21 (m, 2H), 4.57 (q, 2H), 6.28-6.32 (m, 1H), 7.29 (s, 1H), 7.37 (m, 1H), 7.70-7.87 (m, 2H), 8.06 (d, 1H), 8.20 (s, 1H), 9.67 (m, 1H).

Step 7: 5-(Aminomethyl)-1-ethyl-6-methyl-N-{2,2,2-trifluoro-1-[3-(trifluoromethyl)phenyl]ethyl}-1H-pyrrolo[2,3-b]pyridine-2-carboxamide

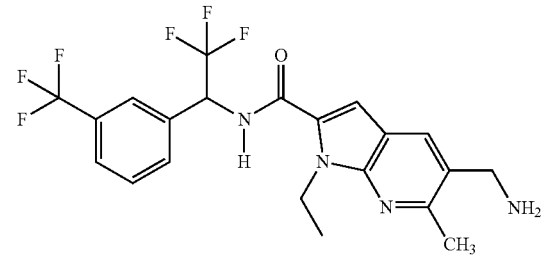 [SMILES: CCn1c(C(=O)NC(c2cccc(C(F)(F)F)c2)C(F)(F)F)cc2cc(CN)c(C)nc21]

tert-Butyl {[6-methyl-2-({2,2,2-trifluoro-1-[3-(trifluoromethyl)phenyl]ethyl}carbamoyl)-1H-pyrrolo[2,3-b]pyridin-5-yl]methyl}carbamate (274 mg, 0.46 mmol) was initially charged in dichloromethane (5.0 ml), trifluoroacetic acid (526 mg, 4.61 mmol) was added and the mixture was stirred at room temperature for 2 hours. The solvent was removed completely under reduced pressure, giving 210 mg (86% of theory) of 5-(aminomethyl)-1-ethyl-6-methyl-N-{2,2,2-trifluoro-1-[3-(trifluoromethyl)phenyl]ethyl}-1H-pyrrolo[2,3-b]pyridine-2-carboxamide, which were directly reacted further. HPLC-MS: log P=1.94; mass (m/z): 460.1.

Step 8: 5-(Acetamidomethyl)-1-ethyl-6-methyl-N-{2,2,2-trifluoro-1-[3-(trifluoromethyl)phenyl]ethyl}-1H-pyrrolo[2,3-b]pyridine-2-carboxamide

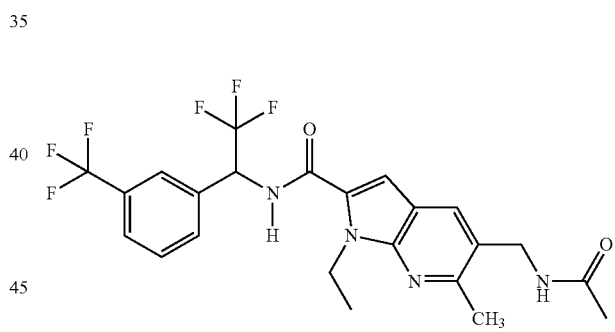

5-(Aminomethyl)-1-ethyl-6-methyl-N-{2,2,2-trifluoro-1-[3-(trifluoromethyl)phenyl]ethyl}-1H-pyrrolo[2,3-b]pyridine-2-carboxamide (70.0 mg, 0.15 mmol) was initially charged in pyridine (1.7 ml), acetyl chloride (14.4 mg, 0.18 mmol) was added and the mixture was stirred at room temperature for 2 hours. Ice-water was added, the reaction mixture was acidified with 2N HCl and the precipitated product was filtered off. After drying, the product was chromatographed using cyclohexane/ethyl acetate (1/1), which gave 5.00 mg (6.5% of theory) of 5-(acetamidomethyl)-1-ethyl-6-methyl-N-{2,2,2-trifluoro-1-[3-(trifluoromethyl)phenyl]ethyl}-1H-pyrrolo[2,3-b]pyridine-2-carboxamide. HPLC-MS: log P=3.16; mass (m/z): 501.1 (M+H)+; 1HNMR (D6-DMSO): δ 1.23 (t, 2H), 2.57 (s, 3H), 3.32 (s, 3H), 4.34 (m, 2H), 4.58 (q, 2H), 6.28-6.30 (m, 1H), 7.30 (s, 1H), 7.70-7.87 (m, 2H), 8.05 (d, 1H), 8.20 (s, 1H), 8.25 (m, 1H), 9.68 (m, 1H).

The compounds of the formula (I-5) according to the invention described in Table 1 below and the compounds according to the invention described in Table 2 are likewise preferred compounds according to the invention which are obtained according to or analogously to the Synthesis Examples described above.

TABLE 1

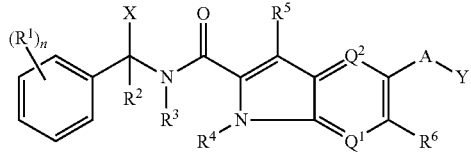

(I-5)

where X represents $CF_3$ and $R^2$, $R^3$ and $R^5$ represent H.

| No. | $(R^1)_n$ | $Q^1$ | $Q^2$ | $R^4$ | $R^6$ | A | Y | $(M+H)^{+a)}$ | log p$^{a)}$ |
|---|---|---|---|---|---|---|---|---|---|
| 1 (Synthesis Example 1) | 3-$CF_3$ | N | CH | Et | Me | CONH | cyclopropyl | 513.1 | 3.52 |
| 2 (Synthesis Example 2) | 3-$CF_3$; 4-F | CH | N | Et | H | CONH | cyclopropyl | 517.1 | 3.78 |
| 3 | 3-$CF_3$ | N | CH | Et | H | CONH | cyclopropyl | 499.1 | 3.19 |
| 4 | 3-$CF_3$ | N | CH | Et | Me | CONH | propan-2-yl | 515.1 | 3.74 |
| 5 | 3-$CF_3$ | N | CH | Et | Me | CONH | cyclobutyl | 527.0 | 3.89 |
| 6 | 3-$CF_3$ | N | CH | Et | Me | CONH | 1-cyanocyclopropyl | 538.1 | 3.53 |
| 7 | 3-$CF_3$ | N | CH | Et | Me | CONH | pyrid-2-ylmethyl | 564.1 | 2.99 |
| 8 | 3-$CF_3$ | N | CH | Et | Me | CONH | 1,3-difluoropropan-2-yl | 551.1 | 3.67 |
| 9 | 3-Cl; 4-F | N | CH | Et | Me | CONH | cyclopropyl | 497.1 | 3.39 |
| 10 | 3-Cl; 4-F | N | CH | Et | Me | CONH | 1-cyanocyclopropyl | 522.1 | 3.51 |
| 11 | 3-$CF_3$ | N | CH | Et | Cl | CONH | 1-cyanocyclopropyl | 558.1 | 3.68 |
| 12 | 3-$CF_3$ | N | CH | Et | Cl | CONH | cyclopropyl | 533.1 | 3.70 |
| 13 | 3-$CF_3$ | N | CH | Et | Cl | CONH | 2,2-difluoroethyl | 557.1 | 3.79 |
| 14 | 3-$CF_3$ | N | CH | Et | Cl | CONH | propan-2-yl | 535.1 | 3.97 |
| 15 | 3-$CF_3$ | N | CH | Et | Cl | CONH | cyclobutyl | 547.1 | 4.12 |
| 16 | 3-Cl; 4-F | N | CH | Et | Cl | CONH | cyclopropyl | 517.1 | 3.61 |
| 17 | 3-Cl; 4-F | N | CH | Et | Cl | CONH | propan-2-yl | 519.3 | 3.88 |
| 18 | 3,5-$Cl_2$; 2,4-$F_2$ | N | CH | Et | Cl | CONH | cyclopropyl | 569.1 | 4.43 |
| 19 | 3,5-$Cl_2$; 2,4-$F_2$ | N | CH | Et | Cl | CONH | propan-2-yl | 571.1 | 4.62 |
| 20 | 3,5-$Cl_2$; 4-F | N | CH | Et | Cl | CONH | cyclopropyl | 551.0 | 4.23 |
| 21 | 3,5-$Cl_2$; 4-F | N | CH | Et | Cl | CONH | propan-2-yl | 553.1 | 4.44 |
| 22 | 3-$CF_3$ | N | CH | Me | Cl | CONH | cyclopropyl | 518.0 | 3.40 |
| 23 | 3-$CF_3$ | N | CH | propyn-3-yl | Cl | CONH | cyclopropyl | 542.1 | 3.45 |
| 24 | 3-$CF_3$ | N | CH | propyn-3-yl | Cl | CONH | propan-2-yl | 545.1 | 3.68 |
| 25 | 3-$CF_3$ | N | CH | propyn-3-yl | Cl | CONH | cyclobutyl | 557.1 | 3.79 |
| 26 | 3-Cl; 4-F | N | CH | Et | Cl | CONH | 1-cyanocyclopropyl | 542.0 | 3.62 |
| 27 | 3,5-$Cl_2$; 4-F | N | CH | Et | Cl | CONH | 1-cyanocyclopropyl | 577.1 | 4.11 |
| 28 | 3,5-$Cl_2$ | N | CH | Et | Cl | CONH | cyclopropyl | 534.1 | |
| 29 | 3-$CF_3$; 4-F | N | CH | Et | Cl | CONH | cyclopropyl | 551.0 | |
| 30 | 3-$CF_3$ | N | CH | Et | Cl | CONH | 1-cyanocyclopropyl | 568.0 | 3.43 |
| 31 | 3,5-$Cl_2$; 2,4-$F_2$ | N | CH | Et | Cl | CONH | 1-cyanocyclopropyl | 595.2 | 4.32 |
| 32 | 3,4-$Cl_2$ | N | CH | Et | Cl | CONH | 1-cyanocyclopropyl | 559.1 | 3.94 |
| 33 | 3-$CF_3$ | N | CH | Et | Cl | CONH | 1-(cyclopropyl)eth-1-yl | 561.1 | 4.32 |
| 34 | 3-$CF_3$ | N | CH | Et | Cl | CONH | propan-1-yl | 535.1 | 3.99 |
| 35 | 3-$CF_3$ | N | CH | Et | Cl | CONH | 1,3-difluoropropan-2-yl | 571.1 | 3.83 |
| 36 | 3-$CF_3$ | N | CH | Et | Cl | CONH | 1-fluoropropan-2-yl | 553.1 | 3.83 |
| 37 | 3-$CF_3$ | N | CH | Et | Cl | CONH | pyridin-2-yl-methyl | 584.1 | 3.18 |
| 38 | 3-$CF_3$ | N | CH | Et | Cl | CONH | 1-cyanocyclopropyl | 544.1 | 3.39 |
| 39 | 3-$CF_3$ | N | CH | Et | Cl | CONH | 3-oxetan-1-yl | 549.1 | 3.28 |
| 40 | 3-$CF_3$ | N | CH | Et | Cl | CONH | 5-chloropyridin-2-yl | 604.1 | 4.88 |
| 41 | 3-$CF_3$ | N | CH | Et | Cl | CONH | 2,2,2-trifluoroethyl | 575.1 | 4.08 |
| 42 | 3-$CF_3$ | N | CH | Et | Cl | CONH | cyanomethyl | 532.1 | 3.50 |

TABLE 1-continued (I-5)

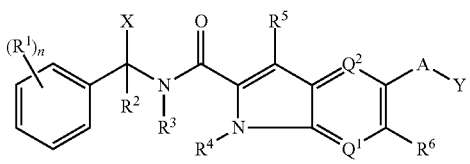

where X represents CF$_3$ and R$^2$, R$^3$ and R$^5$ represent H.

| No. | (R$^1$)$_n$ | Q$^1$ | Q$^2$ | R$^4$ | R$^6$ | A | Y | (M + H)$^{+a)}$ | log p$^{a)}$ |
|---|---|---|---|---|---|---|---|---|---|
| 43 | 3-CF$_3$ | N | CH | Et | Cl | CONH | (2-R)-1-(methylthio)propan-2-yl | 604.1 | 4.88 |
| 44 | 3-CF$_3$ | N | CH | Et | Cl | CONH | methoxycarbonylmethyl | 565.1 | 3.58 |
| 45 | 3-CF$_3$ | N | CH | Et | Cl | CONH | propyn-3-yl | 531.1 | 3.69 |
| 46 | 3-CF$_3$; 4-F | N | CH | Et | Cl | CONH | cyclobutyl | 565.1 | 4.20 |
| 47 | 3-CF$_3$ | N | CH | Et | Cl | CONH | 1,3-pyrimidin-2-ylmethyl | 585.1 | 3.39 |
| 48 | 3,5-Cl$_2$; 4-F | N | CH | Et | Cl | CONH | cyclobutyl | 566.1 | 4.62 |
| 49 | 3-Cl; 4-F | N | CH | Et | Cl | CONH | cyclobutyl | 531.2 | 4.11 |
| 50 | 3-CF$_3$; 4-F | N | CH | Et | Cl | CONH | propan-2-yl | 553.1 | 4.08 |
| 51 | 3-CF$_3$ | N | CH | Et | Cl | CONH | methyl | 507.1 | 3.40 |
| 52 | 3-CF$_3$ | N | CH | Et | Cl | CONH | ethyl | 521.1 | 3.70 |
| 53 | 3-CF$_3$; 4-F | N | CH | Et | Cl | CONH | 1-cyanocyclopropyl | 576.1 | 3.77 |
| 54 | 3,4-Cl$_2$ | N | CH | Et | Cl | CONH | cyclobutyl | 548.1 | 4.47 |
| 55 | 3-CF$_3$; 4-F | N | CH | Et | Cl | CONH | pyridin-2-yl-methyl | 602.1 | 3.32 |
| 56 | 3,4-Cl$_2$ | N | CH | Et | Cl | CONH | propan-2-yl | 536.1 | 4.29 |
| 57 | 3-CF$_3$ | N | CH | Et | Cl | CONH | cyclopropylmethyl | 547.1 | 4.06 |
| 58 | 3-Cl; 4-F | N | CH | Et | Cl | CONH | pyridin-2-yl-methyl | 568.3 | 3.17 |
| 59 | 3,5-Cl$_2$; 2,4-F$_2$ | N | CH | Et | Cl | CONH | pyridin-2-yl-methyl | 621.1 | 3.93 |
| 60 | 3,5-Cl$_2$; 4-F | N | CH | Et | Cl | CONH | pyridin-2-yl-methyl | 603.1 | 3.67 |
| 61 | 3-CF$_3$ | N | CH | propyn-3-yl | Cl | CONH | 5-chloropyridin-2-yl | 614.0 | 4.49 |
| 62 | 3,5-Cl$_2$; 2,4-F$_2$ | N | CH | Et | Cl | CONH | 5-chloropyridin-2-yl | 641.0 | 5.58 |
| 63 | 3,5-Cl$_2$; 2,4-F$_2$ | N | CH | Et | Cl | CONH | 1-(aminothiocarbonyl)cyclopropyl | 629.1 | 4.20 |
| 64 | 3,5-Cl$_2$; 4-F | N | CH | Et | Cl | CONH | 1-(aminothiocarbonyl)cyclopropyl | 611.1 | 3.97 |
| 65 | 3-Cl; 4-F | N | CH | Et | Cl | CONH | 1-(aminothiocarbonyl)cyclopropyl | 576.0 | 3.51 |
| 66 | 3-CF$_3$; 4-F | N | CH | Et | Cl | CONH | 1-(aminothiocarbonyl)cyclopropyl | 610.1 | 3.64 |
| 67 | 3-CF$_3$ | N | CH | Et | Me | CONH | cyclopropyl | 522.1 | 3.33 |
| 68 | 3,5-Cl2, 4-F | N | CH | propyn-3-yl | Cl | CONH | cyclopropyl | 562.1 | 3.85 |
| 69 | 3,5-Cl$_2$; 2,4-F$_2$ | N | CH | propyn-3-yl | Cl | CONH | cyclopropyl | 580.0 | 4.01 |
| 70 | 3-CF$_3$; 4-F | N | CH | propyn-3-yl | Cl | CONH | cyclopropyl | 561.1 | 3.55 |
| 71 | 3,5-Cl$_2$; 2,4-F$_2$ | N | CH | Et | Me | CONH | cyclopropyl | 549.1 | 4.21 |
| 72 | 3,5-Cl2, 4-F | N | CH | Et | Me | CONH | cyclopropyl | 531.1 | 4.00 |
| 73 | 3-CF$_3$ | N | CH | Et | CF$_3$ | CONH | cyclopropyl | 567.2 | 4.00 |
| 74 | 3-CF$_3$ | N | CH | Et | CF$_3$ | CONH | 1-cyanocyclopropyl | 592.2 | 3.93 |
| 75 | 3-CF$_3$; 4-F | N | CH | Et | Me | CONH | 1-cyanocyclopropyl | 556.1 | 3.64 |
| 76 | 3-CF$_3$; 4-F | N | CH | Et | Me | CONH | cyclopropyl | 531.1 | 3.67 |
| 77 | 3,5-Cl$_2$; 4-F | N | CH | Et | CF$_3$ | CONH | 1-cyanocyclopropyl | 610.1 | 4.36 |
| 78 | 3,5-Cl$_2$; 4-F | N | CH | Et | CF$_3$ | CONH | 1-(aminothiocarbonyl)cyclopropyl | 645.2 | 4.25 |
| 79 | 3,5-Cl$_2$; 4-F | N | CH | propyn-3-yl | CF$_3$ | CONH | cyclopropyl | 595.1 | 4.04 |

TABLE 1-continued

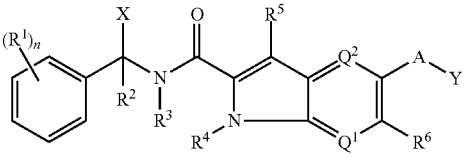

(I-5)

where X represents $CF_3$ and $R^2$, $R^3$ and $R^5$ represent H.

| No. | $(R^1)_n$ | $Q^1$ | $Q^2$ | $R^4$ | $R^6$ | A | Y | $(M+H)^{+a)}$ | log $p^{a)}$ |
|---|---|---|---|---|---|---|---|---|---|
| 80 | 3,5-Cl$_2$; 2,4-F$_2$ | N | CH | propyn-3-yl | Cl | CONH | 1-cyanocyclopropyl | 605.1 | 3.99 |
| 81 | 3-CF$_3$ | N | CH | propyn-3-yl | Me | CONH | 1-cyanocyclopropyl | 548.2 | 3.34 |
| 82 | 3,5-Cl$_2$; 2,4-F$_2$ | N | CH | Et | CF$_3$ | CONH | 1-(aminothiocarbon-yl)cyclopropyl | 663.1 | 4.45 |
| 83 | 4-Cl; 3-CF$_3$ | N | CH | Et | Cl | CONH | 1-cyanocyclopropyl | 593.1 | 4.02 |
| 84 | 4-Cl; 3-CF$_3$ | N | CH | Et | Cl | CONH | 1-(aminothiocarbon-yl)cyclopropyl | 627.1 | 3.90 |
| 85 | 3,5-Cl$_2$; 2,4-F$_2$ | N | CH | Et | CF$_3$ | CONH | cyclopropyl | 630.0 | 4.55 |
| 86 | 3,5-Cl$_2$; 4-F | N | CH | Et | CF$_3$ | CONH | cyclopropyl | 586.1 | 4.42 |
| 87 | 3,5-Cl$_2$; 2,4-F$_2$ | N | CH | Et | CF$_3$ | CONH | cyclopropyl | 604.1 | 4.66 |
| 88 | 4-Cl; 3-CF$_3$ | N | CH | Et | Cl | CONH | cyclopropyl | 568.1 | 4.06 |
| 89 | 4-Cl; 3-CF$_3$ | N | CH | Et | Me | CONH | 1-(aminothiocarbon-yl)cyclopropyl | 606.3 | 3.72 |
| 90 | 4-Cl; 3-CF$_3$ | N | CH | Et | Me | CONH | 1-cyanocyclopropyl | 572.1 | 3.91 |
| 91 | 4-Cl; 3-CF$_3$ | N | CH | Et | Me | CONH | cyclopropyl | 547.3 | 3.90 |
| 92 | 3-CF$_3$ | N | CH | Et | Me | CH$_2$—NH—C(O) | cyclopropyl | 527.1 | 3.59 |
| 93 | 3-CF$_3$ | N | CH | Et | Me | CH$_2$ NH C(O) | ethyl | 515.1 | 3.45 |
| 94 (Synthesis Example 3) | 3-CF$_3$ | N | CH | Et | Me | CH$_2$ NH C(O) | methyl | 501.1 | 3.16 |
| 95 | 3-CF$_3$; 4-F | CH | N | Et | Cl | CONH | cyclopropyl | 551.1 | |

Abbreviations:
Et = ethyl, Me = methyl;

TABLE 2

| No. | Structure | $(M+H)^{+a)}$ | log $p^{a)}$ |
|---|---|---|---|
| 96 | 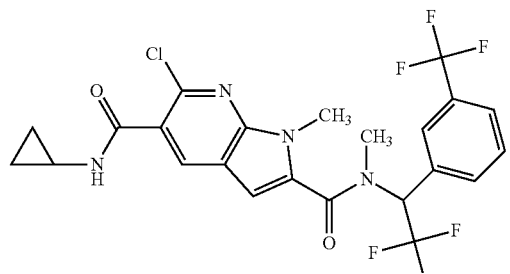 | 533.1 | 3.63 |

TABLE 2-continued

| No. | Structure | (M + H)[+a)] | log p[a)] |
|---|---|---|---|
| 97 | 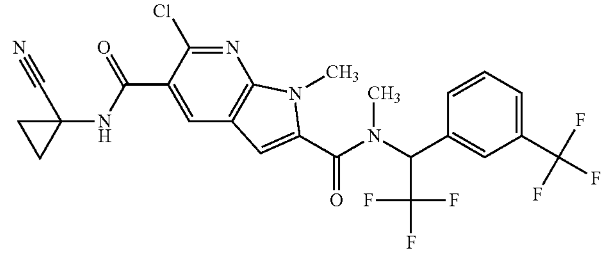 [SMILES: CN(C(=O)c1cc2cc(C(=O)NC3(C#N)CC3)c(Cl)nc2n1C)C(c1cccc(C(F)(F)F)c1)C(F)(F)F] | 558.1 | 3.59 |
| 98 | 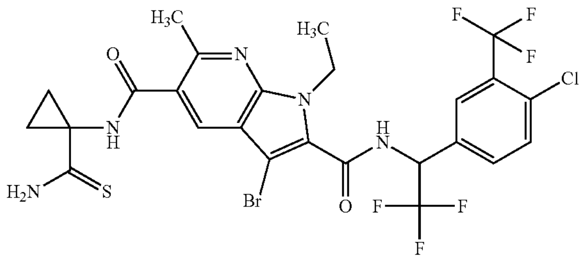 [SMILES: CCn1c(C(=O)NC(c2ccc(Cl)c(C(F)(F)F)c2)C(F)(F)F)c(Br)c2cc(C(=O)NC3(C(N)=S)CC3)c(C)nc21] | 685.2 | 3.97 |

1H NMR data[b)]

Compound No. 1 [DMSO]

See Synthesis Example 1

Compound No. 2 [DMSO]

See Synthesis Example 2

Compound No. 3 [CD3CN]

8.7867 (5.82); 8.7832 (5.92); 8.433 (6.51); 8.4295 (6.35); 8.1508 (1.46); 8.1352 (1.49); 7.985 (3.74); 7.9059 (2.01); 7.8929 (2.25); 7.7889 (1.89); 7.7758 (2.43); 7.6937 (2); 7.6807 (3.26); 7.6676 (1.38); 7.2226 (10.75); 7.1161 (1.35); 6.1852 (0.38); 6.1711 (1.37); 6.1567 (1.92); 6.142 (1.4); 6.1278 (0.41); 4.6717 (0.38); 4.6609 (1.26); 4.6564 (1.07); 4.6492 (3.44); 4.6445 (3.36); 4.6374 (3.34); 4.6328 (3.51); 4.6256 (1.08); 4.6211 (1.31); 4.6103 (0.39); 2.8998 (0.9); 2.8937 (1.38); 2.8877 (2.1); 2.8815 (2.05); 2.8756 (1.41); 2.8695 (0.94); 2.8631 (0.33); 2.1392 (3.46); 1.9645 (3.7); 1.9564 (0.8); 1.9521 (1.12); 1.9484 (13.97); 1.9443 (26.49); 1.9402 (38.65); 1.9361 (26.24); 1.932 (13.35); 1.3866 (1.32); 1.372 (0.49); 1.3031 (7.27); 1.2913 (16); 1.2848 (0.98); 1.2795 (7.48); 1.268 (1.72); 0.8807 (0.32); 0.7885 (1.11); 0.7799 (3.38); 0.7768 (4.34); 0.7683 (4.48); 0.765 (3.43); 0.7569 (1.49); 0.6418 (1.44); 0.6342 (3.9); 0.6304 (3.9); 0.6273 (3.58); 0.6241 (3.7); 0.6158 (1.16); 0.0052 (1.24); −0.0002 (41.76); −0.0058 (1.33)

Compound No. 4 [DMSO]

9.8055 (1.35); 9.7813 (1.37); 8.2418 (1.38); 8.2219 (1.65); 8.213 (1.93); 8.0768 (1.02); 8.0612 (6.41); 7.9532 (1.83); 7.8355 (0.9); 7.8157 (1.28); 7.742 (1.05); 7.7225 (1.56); 7.7029 (0.7); 7.3546 (5.63); 6.3387 (0.52); 6.3167 (0.79); 6.2939 (0.57); 4.6228 (0.66); 4.6056 (1.96); 4.5878 (1.94); 4.5701 (0.63); 4.0964 (0.61); 4.0798 (0.92); 4.0611 (0.92); 4.0445 (0.61); 3.3243 (49.28); 2.9011 (9.04); 2.8911 (16); 2.7315 (12.51); 2.6712 (0.41); 2.6127 (14.16); 2.5247 (1.23); 2.5199 (1.91); 2.5114 (22.44); 2.5069 (45.06); 2.5023 (59.34); 2.4977 (42.39); 2.4931 (20.03); 2.3291 (0.39); 2.0864 (4.21); 1.2389 (3.06); 1.2215 (6.52); 1.2039 (2.97); 1.1934 (4.15); 1.1812 (15.67); 1.1648 (15.14); 0.0079 (1.85); −0.0002 (51.65); −0.0086 (1.6)

Compound No. 5 [DMSO]

9.7895 (1.51); 9.7735 (1.54); 8.5877 (1.43); 8.575 (1.46); 8.2025 (2.04); 8.0898 (5.54); 8.0662 (1.1); 8.0532 (1.19); 7.8291 (1.04); 7.8159 (1.33); 7.7349 (1.06); 7.7218 (1.75); 7.7087 (0.77); 7.3534 (5.21); 6.3207 (0.49); 6.3058 (0.76); 6.2913 (0.55); 4.6115 (0.7); 4.5999 (1.89); 4.5875 (1.88); 4.5759 (0.68); 4.4213 (0.49); 4.4076 (0.95); 4.3941 (0.96); 4.3811 (0.51); 4.0933 (0.68); 4.0845 (2.06); 4.0758 (2.1); 4.0671 (0.73); 4.0358 (0.87); 4.024 (0.87); 3.3177 (870.48); 3.1741 (10.42); 3.1654 (10.28); 2.8905 (0.6); 2.7312 (0.49); 2.6157 (1.26); 2.6126 (2.23); 2.608 (16); 2.522 (2.71); 2.5189 (3.38); 2.5158 (3.4); 2.507 (77.26); 2.504 (168.09); 2.501 (233.71); 2.4979 (172.73); 2.4949 (81.55); 2.3882 (1.01); 2.3851 (1.43); 2.3821 (1.03); 2.379 (0.48); 2.2773 (0.35); 2.2723 (0.48); 2.2651 (0.7); 2.2595 (1.11); 2.255 (0.96); 2.2521 (0.99); 2.2468 (1.11); 2.2395 (0.87); 2.2328 (0.5); 2.2276 (0.42); 2.0403 (0.97); 2.0363 (0.82); 2.0242 (1.35); 2.0204 (1.28); 2.0088 (0.92); 2.0048 (1.02); 1.9872 (3.94); 1.7113 (0.61); 1.7011 (0.86); 1.6953 (1.19); 1.6886 (1.25); 1.684 (1.54); 1.6721 (0.84); 1.6671 (0.78); 1.6544 (0.32); 1.2326 (3.39); 1.221 (7.13); 1.2092 (3.29); 1.1868 (1.03); 1.175 (2.08); 1.1631 (0.98); 0.0052 (1.09); −0.0002 (36.05); −0.0058 (1.12)

Compound No. 6 [DMSO]

9.8341 (1.69); 9.8101 (1.72); 9.28 (3.64); 8.3157 (0.75); 8.2055 (2.41); 8.1736 (6.21); 8.0725 (1.28); 8.0531 (1.42); 7.8359 (1.19); 7.8161 (1.69); 7.7419 (1.3); 7.7224 (2); 7.7027 (0.84); 7.3641 (6.34); 6.3414 (0.66); 6.3186 (1.02); 6.2957 (0.72); 4.619 (0.81); 4.6016 (2.41); 4.5838 (2.37); 4.566 (0.77); 3.3212 (218.88); 2.6894 (0.53); 2.6796 (0.85); 2.6752 (1.65); 2.6706 (2.25); 2.666 (1.65); 2.6616 (0.81); 2.6261 (16); 2.5405 (1.18); 2.5238 (7.93); 2.5105 (126.23); 2.5061 (249.98); 2.5015 (326.42); 2.497 (235.26); 2.4925 (113.22); 2.3373 (0.77); 2.3328 (1.58); 2.3283 (2.14); 2.3237 (1.56); 1.9886 (0.45); 1.6003 (1.3); 1.5861 (3.18); 1.5793 (3.43); 1.5663 (1.48); 1.3187 (1.7); 1.3054 (3.43); 1.2986 (3.62); 1.2842 (1.35); 1.2413 (3.47); 1.2239 (7.5); 1.2063 (3.29); 0.146 (1.15); 0.0079 (10.63); −0.0002 (281.91); −0.0085 (10.13); −0.1497 (1.17)

Compound No. 7 [DMSO]

9.8173 (1.73); 9.7931 (1.74); 8.9985 (0.92); 8.9836 (1.92); 8.9687 (0.89); 8.5415 (1.67); 8.5295 (1.56); 8.3155 (0.61); 8.229 (6.5); 8.2138 (2.42); 8.0791 (1.33); 8.0602 (1.52); 7.837 (1.31); 7.8283 (1.2); 7.8233 (1.51); 7.8173 (1.88); 7.8092 (2.16); 7.8046 (1.92); 7.7899 (1.16); 7.7854 (1.1); 7.7531 (0.36); 7.7428 (1.41); 7.7233 (1.98); 7.7038 (0.87); 7.4368 (2.26); 7.417 (2.05); 7.3793 (6.25); 7.3068 (1.27); 7.2944 (1.31); 7.2892 (1.36); 7.2773 (1.16); 6.3428 (0.66); 6.3208 (1.02); 6.2982 (0.72); 4.6307 (0.94); 4.6127 (2.55); 4.5943 (3.16); 4.5878 (4.86); 4.5728 (4.41); 4.0377 (0.42); 4.0199 (0.43); 3.3206 (152.55); 2.8906 (2.12); 2.731 (1.84); 2.7104 (0.74); 2.6894 (1.68); 2.6749 (1.52); 2.6703 (2.19); 2.6583 (16); 2.5234 (6.63); 2.5102 (102.82); 2.506 (196.2); 2.5015 (251.79); 2.497 (180.78); 2.4927 (86.96); 2.3327 (1.26); 2.3283 (1.68); 2.3238 (1.23); 1.9885 (1.85); 1.3644 (0.34); 1.252 (3.44); 1.2346 (7.76); 1.2169 (3.32); 1.1926 (0.52); 1.1748 (0.99); 1.157 (0.5); 0.1458 (0.88); 0.0075 (8.25); −0.0002 (187.24); −0.0085 (6.4); −0.1498 (0.89)

Compound No. 8 [DMSO]

9.8253 (1.64); 9.8012 (1.67); 8.7409 (1.69); 8.7215 (1.73); 8.2112 (2.33); 8.1285 (6.47); 8.0767 (1.24); 8.0577 (1.39); 7.8365 (1.13); 7.8166 (1.59); 7.7428 (1.3); 7.7232 (1.95); 7.7036 (0.81); 7.3693 (6.46); 6.3422 (0.65); 6.3199 (0.98); 6.2972 (0.71); 4.6713 (3.12); 4.6592 (3.99); 4.6264 (0.83); 4.6092 (2.39); 4.5913 (2.46); 4.5737 (1); 4.5656 (0.68); 4.5541 (2.93); 4.5432 (4.17); 4.526 (0.5); 4.5199 (0.39); 4.5134 (0.4); 4.5076 (0.47); 4.4942 (0.41); 3.3219 (65.36); 2.6889 (0.33); 2.6801 (0.32); 2.6754 (0.6); 2.671 (0.82); 2.6664 (0.6); 2.6617 (0.33); 2.6341 (16); 2.5409 (0.38); 2.5241 (2.48); 2.5108 (44.07); 2.5064 (87.31); 2.5019 (113.95); 2.4973 (81.23); 2.4928 (38.44); 2.3331 (0.53); 2.3286 (0.73); 2.324 (0.53); 1.9888 (1.1); 1.2449 (3.42); 1.2276 (7.45); 1.2099 (3.25); 1.1928 (0.38); 1.175 (0.62); 0.1458 (0.4); 0.0079 (3.36); −0.0002 (94.46); −0.0086 (3.15); −0.1498 (0.43)

Compound No. 9 [DMSO]

9.6759 (1.71); 9.6516 (1.76); 8.4171 (1.79); 8.4063 (1.8); 8.0952 (1.28); 8.0901 (1.38); 8.0772 (1.54); 8.0706 (7.66); 7.8163 (0.63); 7.8111 (0.67); 7.8052 (0.72); 7.799 (0.76); 7.7954 (0.84); 7.7895 (0.82); 7.7836 (0.79); 7.7785 (0.7); 7.5636 (1.83); 7.541 (2.73); 7.5188 (1.57); 7.364 (0.56); 7.3433 (6.61); 6.2424 (0.67); 6.2205 (1); 6.1977 (0.72); 4.6208 (0.74); 4.6045 (1.85); 4.5838 (1.86); 4.5676 (0.7); 3.3256 (27.66); 2.8761 (0.54); 2.8665 (0.74); 2.8579 (1.18); 2.8478 (1.21); 2.8395 (0.73); 2.8297 (0.58); 2.6056 (16); 2.5254 (0.95); 2.5205 (1.48); 2.5121 (18.34); 2.5076 (37.24); 2.5031 (49); 2.4985 (35.1); 2.494 (16.78); 2.3299 (0.33); 1.9897 (0.4); 1.4017 (1.17); 1.2432 (3.32); 1.2258 (7.37); 1.2081 (3.25); 0.7339 (0.78); 0.721 (2.06); 0.7159 (2.95); 0.7038 (2.68); 0.6979 (2.29); 0.6866 (0.97); 0.5694 (1.02); 0.5588 (2.9); 0.5528 (2.55); 0.5487 (2.38); 0.5431 (2.33); 0.5309 (0.73)

Compound No. 10 [DMSO]

9.7145 (2); 9.6902 (2.06); 9.2888 (4.2); 8.1695 (6.44); 8.0931 (1.53); 8.0887 (1.63); 8.0757 (1.61); 8.0713 (1.59); 7.8166 (0.78); 7.8117 (0.85); 7.8057 (0.93); 7.7958 (1.09); 7.79 (1.08); 7.784 (1.03); 7.7794 (0.9); 7.5671 (1.84); 7.5448 (2.93); 7.5223 (1.58); 7.3585 (6.22); 6.2489 (0.81); 6.2272 (1.23); 6.2048 (0.89); 4.6245 (0.91); 4.6077 (2.3); 4.5887 (2.3); 4.5718 (0.93); 4.0567 (0.42); 4.0389 (1.28); 4.0212 (1.31); 4.0034 (0.45); 3.3257 (27.61); 2.6767 (0.33); 2.6723 (0.42); 2.6278 (16); 2.5078 (41.92); 2.5034 (52.79); 2.499 (39.36); 2.3302 (0.34); 1.9899 (5.48); 1.6034 (1.43); 1.5892 (3.68); 1.5825 (3.97); 1.5695 (1.73); 1.3218 (1.84); 1.3086 (3.88); 1.3019 (4.12); 1.2874 (1.57); 1.2512 (3.83); 1.2338 (7.92); 1.2162 (3.73); 1.1934 (1.63); 1.1756 (3.69); 1.158 (1.9); 1.1127 (0.53); 1.1055 (0.47); 0.8716 (0.46); 0.8642 (0.46); −0.0002 (1.14)

Compound No. 11 [DMSO]

9.9483 (3.5); 9.9243 (3.64); 9.4497 (7.68); 8.3874 (13.73); 8.2043 (5.45); 8.0745 (2.91); 8.055 (3.31); 7.8408 (2.6); 7.8212 (3.78); 7.7459 (2.72); 7.7264 (4.22); 7.7069 (1.82); 7.4523 (12); 6.3726 (0.4); 6.3517 (1.47); 6.3298 (2.25); 6.3073 (1.63); 6.2851 (0.49); 4.579 (1.68); 4.5618 (5.04); 4.5441 (5.17); 4.5269 (1.83); 3.3362 (110.77); 3.3271 (163.79); 2.6761 (0.58); 2.6719 (0.78); 2.6673 (0.61); 2.5072 (81.48); 2.5028 (105.36); 2.4984 (81.54); 2.334 (0.59); 2.3297 (0.77); 2.3253 (0.58); 2.0868 (16); 1.9894 (1.11); 1.6256 (2.61); 1.6112 (6.69); 1.6045 (7.23); 1.5915 (3.23); 1.3451 (0.33); 1.3042 (3.12); 1.2907 (6.87); 1.2841 (7.34); 1.2693 (3.6); 1.261 (7); 1.2435 (14.19); 1.2259 (6.84); 1.1932 (0.49); 1.1755 (0.72); 1.1576 (0.42); −0.0002 (23.51); −0.0084 (1.8)

Compound No. 12 [DMSO]

9.92 (3.13); 9.8959 (3.23); 8.5567 (3.44); 8.5459 (3.41); 8.3758 (0.38); 8.2938 (16); 8.2084 (4.45); 8.0769 (2.41); 8.0574 (2.66); 7.8392 (2.2); 7.8194 (3.14); 7.7443 (2.43); 7.7248 (3.71); 7.7053 (1.53); 7.4372 (12.67); 6.3704 (0.32); 6.3489 (1.25); 6.3269 (1.86); 6.3044 (1.33); 6.282 (0.37); 4.5764 (1.43); 4.5591 (4.49); 4.5414 (4.48); 4.524 (1.4); 3.3255 (25.32); 2.8776 (0.38); 2.8676 (1.03); 2.858 (1.35); 2.8495 (2.18); 2.8392 (2.22); 2.831 (1.33); 2.8211 (1.04); 2.811 (0.38); 2.6771 (0.34); 2.6728 (0.46); 2.6682 (0.34); 2.5261 (1.67); 2.5128 (27.48); 2.5083 (55.12); 2.5038 (72.28); 2.4992 (52.01); 2.4947 (24.78); 2.335 (0.33); 2.3305 (0.44); 2.3262 (0.33); 2.0874 (4.7); 1.2693 (0.6); 1.2556 (6.16); 1.2382 (13.77); 1.2204 (5.93); 0.7445 (1.47); 0.7316 (3.86); 0.7265 (5.49); 0.7144 (5.01); 0.7085 (4.22); 0.6971 (1.72); 0.565 (1.9); 0.5543 (5.2); 0.5484 (4.78); 0.5442 (4.5); 0.5388 (4.36); 0.5266 (1.38); 0.0079 (1.19); −0.0002 (32.49); −0.0085 (1.07)

Compound No. 13 [DMSO]

9.9433 (3.36); 9.9193 (3.46); 8.9655 (1.73); 8.9507 (3.58); 8.9357 (1.7); 8.3251 (16); 8.2081 (4.73); 8.0779 (2.54); 8.0583 (2.8); 7.8407 (2.32); 7.821 (3.29); 7.7454 (2.55); 7.7259 (3.87); 7.7064 (1.58); 7.4517 (12.84); 6.3733 (0.36); 6.352 (1.3); 6.3301 (1.97); 6.3071 (1.58); 6.294 (1.44); 6.2847 (0.96); 6.1643 (1.36); 6.1547 (2.86); 6.1451 (1.3); 6.0249 (0.64); 6.0153 (1.42); 6.0058 (0.67); 4.5814 (1.49); 4.5641 (4.63); 4.5464 (4.65); 4.5288 (1.49); 4.0563 (0.44); 4.0385 (1.32); 4.0207 (1.35); 4.0028 (0.44); 3.7505 (0.99); 3.7406 (1.31); 3.7358 (1.19); 3.7259 (1.12); 3.711 (2.2); 3.7011 (2.5); 3.6962 (2.5); 3.6864 (2.1); 3.6713 (1.19); 3.6615 (1.27); 3.6566 (1.33); 3.6469 (1.05); 3.3675 (6.52); 2.6761 (0.54); 2.6715 (0.75); 2.6671 (0.55); 2.5247 (2.79); 2.5114 (42.05); 2.507 (82.92); 2.5025 (110.74); 2.4979 (82.71); 2.4935 (41.06); 2.3384 (0.34); 2.3338 (0.64); 2.3293 (0.87); 2.3247 (0.69); 2.3203 (0.44); 2.0866 (1.27); 1.9894 (5.75); 1.2987 (0.39); 1.2656 (6.35); 1.2482 (14.06); 1.2305 (6.43); 1.1931 (1.63); 1.1753 (3.2); 1.1575 (1.6); 0.0079 (0.51); −0.0002 (13.31); −0.0085 (0.49)

Compound No. 14 [DMSO]

9.9282 (1.71); 9.9041 (1.77); 8.3942 (1.65); 8.3749 (1.67); 8.2744 (8.1); 8.2121 (2.38); 8.0794 (1.28); 8.06 (1.43); 7.8404 (1.16); 7.8205 (1.65); 7.746 (1.29); 7.7265 (1.97); 7.7069 (0.81); 7.4378 (6.44); 6.3513 (0.65); 6.3294 (0.99); 6.3069 (0.71); 4.5817 (0.73); 4.5644 (2.33); 4.5467 (2.35); 4.529 (0.74); 4.0775 (0.66); 4.0607 (1); 4.0423 (1.01); 4.0256 (0.68); 3.3255 (11.68); 2.5259 (0.55); 2.5127 (9.96); 2.5083 (19.83); 2.5037 (26.54); 2.4992 (19.71); 2.4948 (9.62); 2.0876 (1.68); 1.2602 (3.17); 1.2428 (6.95); 1.2251 (3.12); 1.1798 (16); 1.1633 (15.84); −0.0002 (5.94)

Compound No. 15 [DMSO]
9.9263 (3.23); 9.9022 (3.36); 8.7597 (3.17); 8.7406 (3.24); 8.3009 (16); 8.2109 (4.62); 8.0788 (2.46); 8.0593 (2.77); 7.8401 (2.22); 7.8203 (3.23); 7.7455 (2.49); 7.7261 (3.86); 7.7066 (1.61); 7.4416 (13.38); 6.3729 (0.32); 6.3509 (1.26); 6.3289 (1.89); 6.3064 (1.38); 6.2842 (0.4); 4.5822 (1.41); 4.5648 (4.49); 4.5472 (4.54); 4.5295 (1.45); 4.4102 (1.03); 4.3902 (2.04); 4.3701 (2.04); 4.35 (1.1); 4.0571 (0.38); 4.0393 (1.16); 4.0215 (1.17); 4.0037 (0.39); 3.3251 (34.99); 2.6773 (0.33); 2.6727 (0.45); 2.6681 (0.32); 2.526 (1.38); 2.5127 (25.79); 2.5082 (50.83); 2.5036 (67.33); 2.499 (49.22); 2.4945 (23.43); 2.3349 (0.34); 2.3305 (0.46); 2.3258 (0.34); 2.2919 (0.67); 2.2828 (0.98); 2.2752 (1.46); 2.2632 (2.21); 2.2568 (2.46); 2.2488 (2.34); 2.2458 (2.22); 2.2391 (1.95); 2.2358 (2); 2.2171 (0.88); 2.0873 (4.79); 2.0635 (0.63); 2.0567 (0.53); 2.0403 (2.01); 2.0344 (1.66); 2.0156 (2.93); 2.0097 (2.7); 1.99 (6.71); 1.9705 (0.61); 1.9642 (0.71); 1.7285 (1.23); 1.7155 (2.44); 1.705 (2.71); 1.6909 (3.43); 1.6819 (1.7); 1.6713 (1.58); 1.6646 (1.38); 1.6468 (0.61); 1.2607 (6.25); 1.2433 (13.95); 1.2256 (6.17); 1.1937 (1.48); 1.1759 (2.84); 1.1581 (1.43); 0.008 (0.6); −0.0002 (15.43); −0.0085 (0.46)

Compound No. 16 [DMSO]
9.8037 (3.75); 9.7796 (3.87); 8.5647 (4.12); 8.5538 (4.17); 8.3754 (0.39); 8.2925 (16); 8.0979 (2.9); 8.0931 (3.03); 8.0804 (3.05); 8.0756 (2.95); 7.8218 (1.44); 7.8167 (1.57); 7.8107 (1.7); 7.8008 (1.97); 7.795 (1.92); 7.7889 (1.88); 7.7841 (1.6); 7.5729 (3.61); 7.5506 (5.71); 7.5281 (3.11); 7.4316 (13.38); 6.2785 (0.41); 6.2575 (1.52); 6.2357 (2.29); 6.2132 (1.64); 6.1909 (0.47); 4.5838 (1.77); 4.5664 (5.3); 4.5487 (5.33); 4.5311 (1.77); 3.3311 (62.57); 2.8823 (0.41); 2.8724 (1.14); 2.8632 (1.64); 2.8543 (2.53); 2.8442 (2.51); 2.8358 (1.67); 2.8261 (1.19); 2.8158 (0.44); 2.6828 (0.58); 2.6784 (0.74); 2.674 (0.54); 2.5138 (88.42); 2.5094 (112.46); 2.5049 (82.11); 2.3407 (0.57); 2.3362 (0.73); 2.3317 (0.54); 2.0934 (1.7); 1.2822 (0.73); 1.2684 (7.05); 1.2509 (15.26); 1.2332 (6.95); 0.7501 (1.59); 0.7373 (4.72); 0.7322 (6.25); 0.72 (5.97); 0.7142 (4.96); 0.7028 (1.99); 0.5701 (2.12); 0.5595 (6.23); 0.5533 (5.89); 0.5439 (5.27); 0.5315 (1.61)

Compound No. 17 [DMSO]
9.8033 (1.46); 9.7791 (1.53); 8.3951 (1.4); 8.3757 (1.43); 8.2654 (8.45); 8.0938 (1.07); 8.0888 (1.13); 8.0762 (1.09); 8.071 (1.1); 7.8171 (0.52); 7.8114 (0.57); 7.8058 (0.62); 7.7958 (0.7); 7.7899 (0.69); 7.7842 (0.67); 7.7785 (0.59); 7.5681 (1.62); 7.5454 (2.31); 7.5233 (1.41); 7.424 (6.37); 6.2527 (0.56); 6.2304 (0.82); 6.2083 (0.61); 4.581 (0.64); 4.5634 (2.02); 4.5455 (2); 4.5281 (0.64); 4.0743 (0.62); 4.0577 (0.92); 4.0387 (0.95); 4.0222 (0.64); 3.323 (59.91); 2.6758 (0.46); 2.671 (0.63); 2.6666 (0.45); 2.5245 (2.07); 2.5198 (3.1); 2.5111 (35.88); 2.5066 (72.47); 2.502 (96.15); 2.4974 (69.26); 2.4928 (32.85); 2.3334 (0.48); 2.3288 (0.63); 2.3241 (0.47); 1.2649 (2.88); 1.2474 (6.63); 1.2297 (2.85); 1.1927 (0.35); 1.1778 (16); 1.1613 (15.82)

Compound No. 18 [DMSO]
9.9095 (2.48); 9.8857 (2.57); 8.5658 (2.94); 8.5549 (2.95); 8.3892 (0.35); 8.314 (0.95); 8.3061 (14.67); 8.2715 (1.51); 8.2529 (2.88); 8.2345 (1.45); 7.4666 (0.38); 7.4515 (11.18); 6.8832 (0.63); 6.6867 (0.33); 6.3801 (1.02); 6.3588 (1.47); 6.3367 (1.1); 6.3161 (0.34); 4.5729 (1.22); 4.5556 (3.62); 4.5376 (3.57); 4.5202 (1.16); 4.0561 (0.37); 4.0383 (1.1); 4.0205 (1.11); 4.0027 (0.38); 3.4081 (0.32); 3.3954 (0.46); 3.3354 (679.04); 2.8659 (0.86); 2.8563 (1.17); 2.8477 (1.86); 2.8375 (1.9); 2.8291 (1.16); 2.8193 (0.91); 2.8093 (0.35); 2.6813 (0.84); 2.6767 (0.98); 2.6722 (1.4); 2.6676 (0.96); 2.6631 (0.42); 2.5255 (4.21); 2.5207 (6.65); 2.5122 (72.94); 2.5077 (146.36); 2.5031 (193.35); 2.4984 (139.08); 2.4939 (66.09); 2.339 (0.47); 2.3344 (0.92); 2.3298 (1.27); 2.3252 (0.91); 2.3208 (0.41); 2.0868 (16); 1.9892 (5.05); 1.3528 (5.92); 1.2985 (0.38); 1.2826 (0.61); 1.2694 (5.29); 1.252 (11.83); 1.2342 (6.7); 1.1934 (1.5); 1.1836 (0.53); 1.1756 (2.85); 1.1627 (0.39); 1.1578 (1.45); 0.8534 (0.35); 0.7448 (1.27); 0.732 (3.33); 0.7269 (4.71); 0.7148 (4.33); 0.7089 (3.68); 0.6974 (1.55); 0.5723 (0.37); 0.5626 (1.68); 0.5519 (4.49); 0.5459 (4.01); 0.5418 (3.79); 0.5364 (3.72); 0.5242 (1.21); −0.0002 (0.58)

Compound No. 19 [DMSO]
9.9228 (1.49); 9.8992 (1.53); 8.4109 (1.47); 8.3914 (1.48); 8.324 (0.33); 8.2965 (7.1); 8.2857 (0.97); 8.2672 (1.66); 8.2486 (0.85); 7.4604 (6.04); 6.8988 (0.64); 6.3925 (0.64); 6.3712 (0.92); 6.3491 (0.67); 4.5855 (0.74); 4.5681 (2.16); 4.5502 (2.15); 4.5329 (0.72); 4.0821 (0.65); 4.0654 (1.01); 4.0465 (1.15); 4.0301 (0.71); 3.3323 (129.09); 2.6835 (0.93); 2.6791 (1.12); 2.6745 (0.79); 2.67 (0.41); 2.5321 (3.5); 2.5187 (61.02); 2.5144 (120.78); 2.5099 (158.57); 2.5054 (115.85); 2.501 (56.82); 2.3411 (0.76); 2.3366 (1.05); 2.3321 (0.78); 2.0942 (10.69); 1.9968 (1.09); 1.3611 (5.78); 1.2812 (3.12); 1.2638 (6.83); 1.2459 (3.87); 1.2008 (0.84); 1.1858 (16); 1.1693 (15.76); 1.148 (1.01); 1.0269 (1.31); 1.0105 (1.28)

Compound No. 20 [DMSO]
9.7633 (3.66); 9.7389 (3.77); 8.5616 (4.14); 8.5507 (4.15); 8.3787 (0.41); 8.3169 (0.38); 8.2956 (16); 8.118 (10.2); 8.1022 (10.13); 7.4324 (13.26); 6.3417 (0.41); 6.321 (1.46); 6.2989 (2.16); 6.2767 (1.57); 6.2549 (0.45); 4.5765 (1.78); 4.5591 (5.07); 4.5412 (5.05); 4.5237 (1.72); 4.0385 (0.38); 4.0207 (0.4); 3.3254 (111.87); 2.8766 (0.43); 2.8667 (1.17); 2.8575 (1.64); 2.8486 (2.51); 2.8386 (2.52); 2.83 (1.63); 2.8204 (1.19); 2.8105 (0.46); 2.6765 (0.77); 2.6719 (1.02); 2.6675 (0.77); 2.5115 (62.38); 2.5074 (117.97); 2.503 (152.03); 2.4985 (112.7); 2.4943 (57.24); 2.3342 (0.78); 2.3297 (1.02); 2.3253 (0.76); 1.9897 (1.72); 1.3532 (0.37); 1.2811 (0.77); 1.2673 (7.13); 1.2499 (15.22); 1.2323 (7.43); 1.1934 (0.55); 1.1756 (0.96); 1.1578 (0.52); 0.7446 (1.63); 0.7316 (4.71); 0.7267 (6.28); 0.7145 (5.87); 0.7088 (4.99); 0.6972 (1.98); 0.5635 (2.13); 0.5528 (6.2); 0.5467 (5.87); 0.543 (5.53); 0.5374 (5.28); 0.5251 (1.6); 0.0078 (1.38); −0.0002 (28.95); −0.0084 (1.29)

Compound No. 21 [DMSO]
9.7693 (1.66); 9.745 (1.7); 8.3985 (1.68); 8.3791 (1.68); 8.2755 (7.25); 8.1205 (4.5); 8.1047 (4.43); 7.4321 (5.95); 6.323 (0.66); 6.3014 (0.98); 6.2789 (0.69); 4.5816 (0.79); 4.564 (2.23); 4.5462 (2.22); 4.5288 (0.75); 4.0757 (0.67); 4.059 (1.08); 4.0401 (1.17); 4.0236 (0.75); 3.3231 (49.67); 2.676 (0.48); 2.6715 (0.6); 2.6674 (0.42); 2.5069 (72.31); 2.5025 (91.84); 2.4981 (66.88); 2.3336 (0.48); 2.3293 (0.63); 2.325 (0.45); 1.9893 (1.74); 1.3539 (1.29); 1.2715 (3.25); 1.2541 (6.91); 1.2363 (3.58); 1.193 (0.98); 1.179 (16); 1.1625 (15.69); 1.0195 (0.36); 1.0033 (0.36); 0.0078 (1.78); −0.0001 (37.76); −0.0083 (1.59)

Compound No. 22 [DMSO]
9.8617 (1.49); 9.8376 (1.54); 8.5661 (1.69); 8.5553 (1.69); 8.2964 (7.65); 8.2149 (2.17); 8.0781 (1.19); 8.0585 (1.31); 7.8355 (1.07); 7.8157 (1.54); 7.7393 (1.18); 7.7196 (1.82); 7.7003 (0.77); 7.4791 (6.05); 6.3407 (0.6); 6.3183 (0.91); 6.2962 (0.65); 3.9703 (0.68); 3.9572 (16); 3.3241 (33.1); 2.8657 (0.51); 2.8561 (0.65); 2.8476 (1.02); 2.8375 (1.02); 2.8293 (0.64); 2.8193 (0.49); 2.6758 (0.5); 2.6712 (0.66); 2.6667 (0.47); 2.633 (2.1); 2.5246 (1.91); 2.5197 (3); 2.5111 (35.6); 2.5067 (70.84); 2.5021 (93.88); 2.4976 (68.9); 2.4931 (33.12); 2.3334 (0.45); 2.3289 (0.61); 2.3244 (0.42); 1.2356 (0.38); 1.1406 (0.78); 0.744 (0.66); 0.7313 (1.81); 0.7261 (2.53); 0.7139 (2.34); 0.708 (1.94); 0.6966 (0.8); 0.5682

(0.84); 0.5576 (2.42); 0.5515 (2.23); 0.5475 (2.04); 0.542 (2.03); 0.5297 (0.61); 0.008 (0.55); −0.0002 (16.12); −0.0085 (0.51)

Compound No. 23 [DMSO]

9.9508 (2.99); 9.9268 (3.08); 8.5849 (3.29); 8.574 (3.31); 8.4324 (0.41); 8.3441 (16); 8.2072 (4.25); 8.0779 (2.28); 8.0585 (2.57); 7.8389 (2.11); 7.8193 (3.02); 7.7457 (2.35); 7.7261 (3.59); 7.7066 (1.49); 7.5466 (12.95); 6.3624 (1.16); 6.3404 (1.77); 6.3181 (1.28); 6.2954 (0.37); 5.3654 (7.27); 5.3598 (7.14); 3.3255 (51.09); 3.1764 (0.34); 3.1494 (2.87); 3.1435 (6.36); 3.1375 (2.63); 2.8802 (0.36); 2.8704 (0.99); 2.8607 (1.28); 2.8522 (2.1); 2.842 (2.1); 2.8337 (1.27); 2.8239 (1.01); 2.8138 (0.38); 2.6762 (0.41); 2.6718 (0.56); 2.6672 (0.39); 2.5252 (1.96); 2.5203 (3.03); 2.5118 (31.77); 2.5073 (62.98); 2.5027 (82.39); 2.4981 (58.93); 2.4936 (27.63); 2.334 (0.39); 2.3294 (0.53); 2.3249 (0.39); 1.3538 (0.76); 0.7499 (1.41); 0.737 (3.69); 0.7319 (5.25); 0.7197 (4.85); 0.7138 (4.05); 0.7023 (1.65); 0.5668 (1.82); 0.5562 (4.98); 0.5502 (4.53); 0.5459 (4.2); 0.5407 (4.16); 0.5283 (1.34); 0.008 (1.73); −0.0002 (49.16); −0.0086 (1.53)

Compound No. 24 [DMSO]

9.9577 (1.59); 9.9337 (1.65); 8.4209 (1.56); 8.4016 (1.62); 8.3239 (8.91); 8.2096 (2.15); 8.0796 (1.14); 8.0599 (1.3); 7.8396 (1.05); 7.8199 (1.53); 7.7468 (1.18); 7.7273 (1.83); 7.7078 (0.76); 7.5476 (7.07); 6.3642 (0.58); 6.3422 (0.89); 6.3197 (0.65); 5.3702 (3.58); 5.3645 (3.62); 4.0793 (0.64); 4.0628 (0.94); 4.0439 (0.94); 4.0272 (0.64); 3.3226 (22.52); 3.1493 (1.41); 3.1433 (3.36); 3.1373 (1.32); 2.8911 (1.2); 2.7324 (0.89); 2.7314 (0.91); 2.5248 (0.71); 2.5201 (1.06); 2.5115 (14.53); 2.5069 (30.25); 2.5023 (41.6); 2.4977 (30.61); 2.4931 (14.35); 2.0864 (2.82); 1.3545 (1.01); 1.1823 (16); 1.1658 (15.97); 0.008 (0.46); −0.0002 (15.38); −0.0085 (0.44)

Compound No. 25 [DMSO]

9.9575 (1.66); 9.9335 (1.73); 8.7864 (1.67); 8.7674 (1.71); 8.3517 (8.77); 8.2098 (2.3); 8.0802 (1.22); 8.0608 (1.37); 7.8398 (1.11); 7.8201 (1.61); 7.7471 (1.26); 7.7276 (1.94); 7.708 (0.8); 7.5524 (7.12); 6.3649 (0.62); 6.343 (0.94); 6.3204 (0.69); 5.3721 (3.77); 5.3666 (3.82); 4.413 (0.51); 4.3927 (1.01); 4.3727 (1.01); 4.3526 (0.53); 4.0567 (1.15); 4.0389 (3.52); 4.0211 (3.56); 4.0033 (1.18); 3.3242 (15.18); 3.1524 (1.48); 3.1464 (3.37); 3.1404 (1.39); 2.5254 (0.58); 2.5206 (0.88); 2.512 (11.49); 2.5074 (23.53); 2.5028 (31.97); 2.4982 (23.5); 2.4937 (11.03); 2.2878 (0.47); 2.2802 (0.69); 2.2682 (1.07); 2.2615 (1.19); 2.2539 (1.13); 2.2507 (1.06); 2.2439 (0.92); 2.2408 (0.96); 2.2285 (0.45); 2.222 (0.42); 2.0408 (0.97); 2.0347 (0.8); 2.0161 (1.43); 2.0101 (1.35); 1.9896 (16); 1.9647 (0.33); 1.7327 (0.6); 1.7197 (1.19); 1.7091 (1.33); 1.7024 (0.65); 1.695 (1.73); 1.686 (0.82); 1.6754 (0.73); 1.6688 (0.67); 1.1934 (4.2); 1.1756 (8.29); 1.1578 (4.1); 0.008 (0.37); −0.0002 (11.55)

Compound No. 26 [DMSO]

9.8254 (2.95); 9.8013 (3.06); 9.4514 (7.01); 8.3809 (16); 8.089 (2.13); 8.084 (2.23); 8.0714 (2.21); 8.0663 (2.16); 7.8146 (1.05); 7.8092 (1.12); 7.8032 (1.22); 7.7974 (1.27); 7.7932 (1.4); 7.7876 (1.35); 7.7817 (1.31); 7.7764 (1.16); 7.5687 (3.25); 7.5461 (4.59); 7.5239 (2.79); 7.4432 (11.67); 6.2558 (1.08); 6.2342 (1.62); 6.2113 (1.17); 6.1889 (0.34); 4.582 (1.26); 4.5646 (3.83); 4.5467 (3.82); 4.5292 (1.22); 4.0564 (0.5); 4.0385 (1.54); 4.0208 (1.59); 4.003 (0.53); 3.3233 (80.61); 2.6764 (0.56); 2.6718 (0.75); 2.6672 (0.54); 2.5251 (2.17); 2.5203 (3.58); 2.5118 (42.12); 2.5073 (83.67); 2.5027 (110.2); 2.498 (79.29); 2.4935 (37.02); 2.3341 (0.55); 2.3295 (0.72); 2.3249 (0.52); 1.9894 (7.1); 1.626 (2.34); 1.6119 (5.33); 1.605 (5.73); 1.5919 (2.53); 1.304 (2.78); 1.2904 (5.42); 1.2837 (5.91); 1.2689 (7.63); 1.2513 (12.75); 1.2335 (6.03); 1.1933 (1.98); 1.1755 (3.95); 1.1577 (1.93); 0.008 (1.73); −0.0002 (51.61); −0.0086 (1.55)

Compound No. 27 [DMSO]

9.791 (3.32); 9.7667 (3.43); 9.4559 (7.65); 8.3903 (16); 8.116 (9.1); 8.1002 (9.05); 7.4505 (12.89); 6.3466 (0.34); 6.3256 (1.24); 6.3038 (1.82); 6.2812 (1.32); 6.2596 (0.38); 4.5809 (1.49); 4.5635 (4.26); 4.5455 (4.2); 4.5279 (1.41); 4.0561 (0.33); 4.0384 (0.99); 4.0205 (1.02); 4.0028 (0.34); 3.3233 (75.24); 2.6805 (0.42); 2.6761 (0.85); 2.6716 (1.15); 2.6671 (0.82); 2.6625 (0.39); 2.5248 (4.17); 2.5115 (68.3); 2.5071 (133.47); 2.5025 (173.17); 2.498 (123.58); 2.4935 (58.46); 2.3379 (0.43); 2.3338 (0.87); 2.3293 (1.16); 2.3248 (0.85); 2.3202 (0.39); 1.9894 (4.42); 1.6275 (2.6); 1.6133 (6.13); 1.6064 (6.56); 1.5934 (2.78); 1.3033 (3.11); 1.2897 (6.37); 1.283 (7.09); 1.2744 (7.09); 1.2689 (4.03); 1.2569 (14.11); 1.2392 (6.31); 1.1932 (1.26); 1.1754 (2.43); 1.1576 (1.22); 0.146 (0.36); 0.008 (3.53); −0.0002 (91.23); −0.0085 (2.93); −0.1496 (0.38)

Compound No. 28 [DMSO]

9.8197 (3.4); 9.7956 (3.51); 8.5574 (3.75); 8.5465 (3.79); 8.3705 (0.37); 8.2877 (15.41); 8.1121 (6.48); 7.7879 (0.5); 7.7678 (16); 7.7437 (0.33); 7.4285 (12.42); 6.2881 (0.34); 6.2673 (1.33); 6.2453 (1.99); 6.223 (1.45); 6.2008 (0.41); 4.575 (1.49); 4.5579 (4.58); 4.5401 (4.6); 4.5226 (1.47); 3.3232 (55.75); 2.8756 (0.36); 2.8656 (0.99); 2.8561 (1.39); 2.8474 (2.17); 2.8374 (2.19); 2.8287 (1.39); 2.8194 (1.04); 2.809 (0.39); 2.6761 (0.53); 2.6716 (0.73); 2.6673 (0.51); 2.5248 (1.91); 2.5114 (39.33); 2.5071 (78.76); 2.5026 (105.08); 2.4981 (77.43); 2.4937 (37.73); 2.3338 (0.53); 2.3294 (0.7); 2.3248 (0.51); 1.3533 (0.44); 1.2744 (0.54); 1.2604 (6.24); 1.243 (13.75); 1.2253 (6.17); 0.7434 (1.4); 0.7305 (3.97); 0.7255 (5.46); 0.7132 (5.1); 0.7074 (4.29); 0.696 (1.72); 0.5635 (1.8); 0.5527 (5.35); 0.5467 (4.84); 0.543 (4.55); 0.5372 (4.49); 0.5249 (1.36); 0.008 (1.72); −0.0002 (52.75); −0.0085 (1.82)

Compound No. 29 [DMSO]

9.8878 (3.65); 9.8637 (3.74); 8.5567 (4.06); 8.546 (3.96); 8.375 (0.37); 8.2928 (16); 8.1836 (1.52); 8.1776 (1.67); 8.1696 (1.92); 8.1622 (1.72); 8.1567 (1.66); 7.6886 (2.32); 7.6636 (3.08); 7.6403 (2.15); 7.4218 (12.2); 6.4083 (0.4); 6.387 (1.5); 6.3654 (2.25); 6.3427 (1.59); 6.3207 (0.45); 4.5755 (1.75); 4.5583 (5.24); 4.5406 (5.24); 4.5232 (1.7); 3.3242 (31.48); 2.8767 (0.42); 2.8668 (1.11); 2.8576 (1.61); 2.8487 (2.41); 2.8388 (2.37); 2.8302 (1.61); 2.8206 (1.09); 2.8104 (0.4); 2.6727 (0.61); 2.5079 (69.72); 2.5036 (86.45); 2.4993 (62.85); 2.3348 (0.45); 2.3305 (0.57); 1.2995 (0.56); 1.2922 (0.32); 1.2599 (7.31); 1.2426 (14.36); 1.225 (6.76); 0.7445 (1.5); 0.7314 (4.66); 0.7267 (5.89); 0.7144 (5.71); 0.7087 (4.66); 0.6972 (1.79); 0.5642 (2); 0.5536 (6.08); 0.5473 (5.79); 0.5382 (5.01); 0.5258 (1.45); −0.0002 (37.11); −0.0085 (1.41)

Compound No. 30 [DMSO]

11.9531 (0.38); 9.9776 (2.76); 9.9536 (2.84); 9.4803 (6.2); 8.4395 (11.42); 8.2038 (4.23); 8.076 (2.22); 8.0565 (2.5); 7.8398 (2.04); 7.8202 (2.93); 7.7469 (2.13); 7.7273 (3.26); 7.7078 (1.35); 7.5627 (9.79); 6.3663 (1.12); 6.3444 (1.7); 6.3218 (1.21); 6.2996 (0.33); 5.3707 (6.81); 5.3659 (6.69); 3.3232 (51.63); 3.161 (2.46); 3.1554 (4.97); 3.1495 (2.28); 2.6754 (0.51); 2.6713 (0.67); 2.6669 (0.51); 2.5067 (74.7); 2.5022 (96.93); 2.4978 (73.48); 2.3331 (0.48); 2.3291 (0.64); 2.3246 (0.48); 2.198 (0.52); 2.1796 (1.03); 2.1612 (0.55); 2.1179 (0.34); 1.6318 (1.97); 1.6172 (5.18); 1.6107 (5.46); 1.5976 (2.19); 1.475 (0.37); 1.353 (0.74); 1.309 (2.37); 1.2953 (5.38); 1.2889 (5.57); 1.2742 (2.23); 1.2351 (16); 1.1409 (0.82); 0.8694 (0.58); 0.8537 (1.54); 0.8361 (0.64); −0.0002 (17.04); −0.0084 (0.71)

Compound No. 31 [DMSO]

9.9346 (3.32); 9.9109 (3.44); 9.4589 (7.89); 8.403 (16); 8.3158 (0.41); 8.2683 (1.96); 8.2499 (3.56); 8.2314 (1.9); 7.4709 (13.31); 6.4037 (0.36); 6.3834 (1.36); 6.3622 (2); 6.3401 (1.45); 6.319 (0.43); 4.5785 (1.55); 4.5612 (4.57); 4.5433 (4.56); 4.5256 (1.5); 3.322 (101.6); 2.6759 (0.93); 2.6714 (1.24); 2.6669 (0.88); 2.6624 (0.42); 2.5248 (3.54); 2.5199 (5.61); 2.5113 (67.53); 2.5069 (134.84); 2.5023 (179.11); 2.4978 (131.22); 2.4933 (63.25); 2.3337 (0.9); 2.3291 (1.2); 2.3245 (0.86); 2.1178 (0.37); 1.6275 (2.61); 1.6134 (6.29); 1.6065 (6.78); 1.5935 (2.86); 1.3529 (1.19); 1.3418 (0.34); 1.3023 (3.19); 1.2887 (6.65); 1.2817 (8.12); 1.2771 (8.04); 1.2674 (4.06); 1.2594 (14.6); 1.2416 (6.57); 1.1406 (0.92); 0.008 (1.14); −0.0002 (34.91); −0.0085 (1.14)

Compound No. 32 [DMSO]

11.9697 (0.33); 9.8506 (0.45); 9.8265 (0.46); 9.4531 (1.07); 8.3843 (2.24); 8.1113 (0.82); 7.7703 (2.1); 7.4471 (1.75); 4.5627 (0.59); 4.545 (0.59); 3.327 (1.33); 2.5253 (0.33); 2.5121 (5.88); 2.5076 (11.42); 2.503 (14.99); 2.4985 (10.98); 2.494 (5.31); 1.9095 (16); 1.6269 (0.34); 1.6126 (0.81); 1.6058 (0.87); 1.5927 (0.37); 1.3044 (0.41); 1.2909 (0.83); 1.2842 (0.9); 1.268 (1.04); 1.2502 (1.94); 1.2335 (1.81); 0.008 (0.35); −0.0002 (8.02)

Compound No. 33 [DMSO]

9.9357 (3.15); 9.9116 (3.25); 8.443 (3.09); 8.4222 (3.17); 8.2614 (14.69); 8.2118 (4.53); 8.0785 (2.41); 8.0589 (2.72); 7.8415 (2.22); 7.8219 (3.2); 7.7459 (2.38); 7.7264 (3.71); 7.7067 (1.52); 7.4354 (11.7); 6.3508 (1.23); 6.3293 (1.87); 6.3068 (1.33); 6.2849 (0.38); 4.5785 (1.4); 4.5611 (4.32); 4.5434 (4.37); 4.526 (1.4); 4.038 (0.71); 4.0201 (0.71); 3.5468 (0.99); 3.5273 (1.91); 3.5096 (1.95); 3.4905 (1.02); 3.3418 (53.32); 2.6755 (0.96); 2.671 (1.27); 2.6665 (0.93); 2.5242 (3.88); 2.5108 (72.78); 2.5064 (143.99); 2.5019 (188.35); 2.4974 (137.23); 2.493 (66.47); 2.3375 (0.46); 2.3332 (0.93); 2.3287 (1.28); 2.3242 (0.92); 1.9891 (3.1); 1.7597 (0.39); 1.3555 (1.49); 1.2584 (6.09); 1.2409 (13.54); 1.2269 (16); 1.2103 (13.58); 1.1925 (1.21); 1.1747 (1.99); 1.1569 (1.07); 0.9601 (0.67); 0.9525 (0.95); 0.94 (1.84); 0.9324 (1.19); 0.9279 (1.27); 0.9199 (1.95); 0.9076 (1.13); 0.9001 (0.78); 0.8875 (0.41); 0.4894 (0.38); 0.4806 (0.52); 0.4761 (0.65); 0.4678 (1.48); 0.4598 (1.36); 0.4545 (1.62); 0.4458 (2.11); 0.4397 (0.9); 0.4333 (1.21); 0.4254 (1.67); 0.4167 (1.31); 0.4041 (1.56); 0.3964 (1.69); 0.3835 (2.35); 0.3713 (1.72); 0.3617 (2.46); 0.3488 (2.26); 0.3386 (1.6); 0.3256 (0.66); 0.2956 (0.95); 0.2828 (1.64); 0.2735 (2.19); 0.2611 (1.82); 0.2513 (1.05); 0.2385 (0.45); −0.0002 (3.49)

Compound No. 34 [DMSO]

9.9278 (2.92); 9.9037 (2.95); 8.5128 (1.75); 8.4988 (3.11); 8.4846 (1.47); 8.3034 (1.29); 8.2948 (13.17); 8.2128 (4.1); 8.0806 (2.32); 8.0611 (2.42); 7.8414 (2.1); 7.8221 (2.81); 7.7461 (2.2); 7.7265 (3.25); 7.7071 (1.33); 7.4501 (1.37); 7.4414 (10.55); 6.373 (0.35); 6.3523 (1.21); 6.3305 (1.74); 6.308 (1.22); 6.2858 (0.35); 5.7596 (0.79); 4.5809 (1.53); 4.5636 (4.14); 4.546 (4.03); 4.5286 (1.27); 4.0392 (0.6); 4.0214 (0.6); 3.3354 (2.95); 3.3267 (33.06); 3.2442 (2.21); 3.2274 (4.69); 3.2124 (4.46); 3.1954 (1.98); 2.6727 (0.39); 2.5125 (31.06); 2.5081 (49.65); 2.5036 (60.19); 2.4991 (42.96); 2.4948 (20.9); 2.3349 (0.34); 2.3303 (0.4); 1.9903 (2.64); 1.5936 (0.59); 1.5755 (2.5); 1.5575 (4.75); 1.5397 (4.79); 1.5217 (2.56); 1.5037 (0.59); 1.3544 (0.92); 1.3378 (0.66); 1.2998 (0.38); 1.2619 (5.86); 1.2445 (11.88); 1.2266 (5.73); 1.1934 (0.83); 1.1756 (1.49); 1.1578 (0.76); 0.9589 (8.16); 0.9494 (2.43); 0.9405 (16); 0.9219 (6.87); 0.1809 (0.43); 0.0085 (0.38); −0.0002 (3.44)

Compound No. 35 [DMSO]

9.9469 (3.31); 9.9229 (3.39); 8.9458 (3.59); 8.9259 (3.67); 8.324 (16); 8.2107 (4.74); 8.0794 (2.52); 8.06 (2.81); 7.8425 (2.32); 7.8226 (3.3); 7.7473 (2.55); 7.7277 (3.92); 7.708 (1.69); 7.4518 (13.1); 6.377 (0.34); 6.3552 (1.3); 6.3332 (1.96); 6.3108 (1.41); 6.2887 (0.41); 4.668 (6.49); 4.6561 (7.83); 4.5841 (1.65); 4.5668 (5.29); 4.5499 (10.59); 4.5395 (9.42); 4.5132 (0.66); 4.508 (0.54); 4.5011 (0.84); 4.4879 (0.89); 4.4813 (0.89); 4.4684 (0.91); 4.455 (0.54); 4.4497 (0.48); 4.4417 (0.37); 4.4368 (0.46); 4.4298 (0.44); 4.4167 (0.43); 3.3247 (41.85); 2.6765 (0.5); 2.6719 (0.68); 2.6674 (0.5); 2.5252 (2.4); 2.5119 (38.28); 2.5074 (75.13); 2.5028 (98.09); 2.4983 (70.55); 2.4938 (33.44); 2.3342 (0.46); 2.3296 (0.64); 2.325 (0.45); 1.9898 (0.39); 1.2642 (6.88); 1.2467 (15.33); 1.229 (6.73); −0.0002 (0.93)

Compound No. 36 [DMSO]

9.9373 (3.6); 9.9132 (3.69); 8.6271 (3.73); 8.6074 (3.78); 8.2966 (15.45); 8.2097 (5.22); 8.0778 (2.79); 8.0585 (3.1); 7.8414 (2.55); 7.8217 (3.65); 7.7457 (2.76); 7.7262 (4.24); 7.7066 (1.8); 7.4422 (13.87); 6.3736 (0.38); 6.3519 (1.43); 6.3301 (2.18); 6.3076 (1.56); 6.2855 (0.45); 4.58 (1.71); 4.5627 (5.31); 4.5451 (5.39); 4.5275 (1.73); 4.4887 (4.87); 4.4759 (5.4); 4.3704 (4.65); 4.3575 (5.74); 4.2985 (0.46); 4.2855 (0.81); 4.2816 (0.71); 4.2667 (1.09); 4.249 (1.17); 4.2359 (1.06); 4.2181 (1.03); 4.1996 (0.74); 3.3229 (88.42); 2.6754 (0.98); 2.6709 (1.33); 2.6664 (0.97); 2.6619 (0.47); 2.5241 (4.68); 2.5108 (77.05); 2.5064 (151.7); 2.5019 (198.54); 2.4973 (145.22); 2.4929 (71.15); 2.3331 (1); 2.3287 (1.34); 2.3241 (0.99); 2.3198 (0.49); 1.2596 (7.23); 1.2421 (16); 1.2244 (7.19); 1.1994 (11.98); 1.1977 (12.27); 1.1825 (12.13); 1.1805 (11.97); −0.0002 (1.71)

Compound No. 37 [DMSO]

9.961 (0.33); 9.9445 (2.05); 9.9205 (2.07); 9.1604 (1.17); 9.1455 (2.49); 9.1305 (1.18); 8.5434 (1.96); 8.5317 (1.95); 8.4109 (8.58); 8.2137 (2.88); 8.1457 (0.35); 8.0817 (1.54); 8.0619 (1.72); 7.9533 (2.12); 7.8448 (2.44); 7.841 (2.37); 7.8256 (4.09); 7.8217 (4.11); 7.8067 (1.39); 7.8023 (1.36); 7.7474 (1.54); 7.7278 (2.29); 7.7081 (1.05); 7.4906 (2.78); 7.4709 (2.62); 7.4585 (7.6); 7.3166 (1.48); 7.3043 (1.54); 7.2994 (1.51); 7.2863 (1.32); 6.3565 (0.8); 6.3347 (1.23); 6.3123 (0.89); 4.5892 (5.89); 4.5736 (6.83); 4.5534 (3.15); 4.5359 (1.04); 3.324 (36.18); 2.8908 (16); 2.7313 (13.68); 2.6894 (14.91); 2.6717 (0.7); 2.6669 (0.5); 2.5107 (37.21); 2.5067 (71.69); 2.5023 (93.68); 2.4978 (69.66); 2.3333 (0.46); 2.329 (0.62); 2.3247 (0.48); 1.2718 (4.16); 1.2543 (9.03); 1.2366 (4.22); −0.0002 (0.67)

Compound No. 38 [DMSO]

9.89 (1.53); 9.8659 (1.58); 9.4634 (3.47); 8.395 (7); 8.2154 (2.19); 8.079 (1.16); 8.0597 (1.31); 7.8392 (1.08); 7.8193 (1.54); 7.7423 (1.18); 7.7229 (1.83); 7.7035 (0.78); 7.4968 (5.84); 6.3486 (0.6); 6.3262 (0.91); 6.3038 (0.65); 3.9642 (16); 3.3241 (30.1); 2.891 (1.67); 2.7318 (1.37); 2.6895 (0.69); 2.676 (0.32); 2.6715 (0.44); 2.667 (0.33); 2.5248 (1.51); 2.5113 (25.29); 2.5069 (50.24); 2.5024 (65.89); 2.4978 (47.95); 2.4934 (23.22); 2.3291 (0.42); 1.6269 (1.21); 1.6127 (2.91); 1.6058 (3.13); 1.5928 (1.35); 1.3077 (1.46); 1.2942 (2.99); 1.2875 (3.18); 1.2731 (1.16); 1.2341 (0.38); −0.0002 (0.53)

Compound No. 39 [DMSO]

9.9346 (0.54); 9.9106 (0.55); 9.3035 (0.61); 9.2869 (0.61); 8.3756 (2.58); 8.2115 (0.75); 8.0808 (0.4); 8.0613 (0.45); 7.9543 (2.08); 7.8431 (0.36); 7.8233 (0.52); 7.7481 (0.41); 7.7285 (0.61); 7.4592 (2.1); 5.0022 (0.41); 4.9853 (0.45); 4.8289 (0.99); 4.8124 (1.48); 4.7943 (0.87); 4.5719 (1.79); 4.5556 (2.57); 4.54 (1.08); 4.1023 (0.51); 4.0891 (0.52); 3.3268 (10.17); 3.1766 (2.55); 3.1634 (2.47); 2.8918 (16); 2.7325 (13.4); 2.69 (13.23); 2.5254 (0.33); 2.5121 (6.46); 2.5077 (12.7); 2.5032 (16.54); 2.4986 (12); 2.4942 (5.87); 1.2666 (1.12); 1.2491 (2.47); 1.2314 (1.13)

Compound No. 40 [DMSO]
11.2864 (7.95); 9.9403 (3.79); 9.9163 (3.92); 8.507 (15.66); 8.4348 (5.01); 8.4285 (5); 8.2783 (2.59); 8.256 (3.04); 8.2158 (5.61); 8.0859 (2.98); 8.0665 (3.31); 8.0165 (4.21); 8.0099 (3.95); 7.9943 (3.51); 7.9876 (3.4); 7.8443 (2.69); 7.8248 (3.88); 7.7498 (2.91); 7.7302 (4.5); 7.7109 (1.86); 7.493 (13.84); 7.3376 (0.4); 7.3335 (0.38); 7.1833 (0.73); 7.1777 (0.44); 6.3845 (0.39); 6.3637 (1.5); 6.3417 (2.28); 6.3193 (1.61); 6.2974 (0.45); 5.759 (1.5); 4.6055 (1.68); 4.5883 (5.17); 4.5706 (5.17); 4.553 (1.66); 4.0388 (0.79); 4.021 (0.79); 3.3257 (61.91); 2.6768 (0.57); 2.6723 (0.76); 2.6679 (0.55); 2.5255 (2.62); 2.5121 (44.83); 2.5078 (86.13); 2.5033 (110.64); 2.4988 (79.54); 2.4944 (37.97); 2.3345 (0.55); 2.33 (0.73); 2.3256 (0.51); 2.3005 (0.39); 1.99 (3.42); 1.3369 (7.67); 1.318 (0.35); 1.2876 (7.4); 1.2701 (16); 1.2498 (11.77); 1.2373 (1.86); 1.1932 (1.3); 1.1881 (0.54); 1.1753 (2.28); 1.1576 (1.09); 1.1495 (0.33); 0.8534 (0.62); 0.835 (0.43); 0.0078 (1.76); −0.0002 (45.34); −0.0085 (1.53)

Compound No. 41 [DMSO]
9.9554 (3.22); 9.9313 (3.25); 9.2407 (1.71); 9.225 (3.65); 9.209 (1.7); 8.3397 (16); 8.3301 (1.24); 8.3268 (0.79); 8.2096 (4.82); 8.0783 (2.56); 8.0588 (2.86); 7.9527 (0.65); 7.8421 (2.36); 7.8225 (3.38); 7.7458 (2.58); 7.7262 (3.98); 7.7066 (1.64); 7.4801 (0.33); 7.4654 (0.93); 7.4561 (12.83); 7.4418 (0.92); 6.3749 (0.36); 6.3533 (1.29); 6.3317 (1.93); 6.309 (1.38); 6.2865 (0.4); 4.5828 (1.47); 4.5653 (4.61); 4.5476 (4.67); 4.53 (1.53); 4.1656 (0.88); 4.1413 (2.83); 4.1253 (2.89); 4.117 (3.14); 4.101 (2.86); 4.0929 (1.26); 4.0766 (0.96); 3.3231 (178.23); 2.8908 (4.08); 2.7315 (3.12); 2.6892 (4.66); 2.68 (0.72); 2.6755 (1.51); 2.6709 (2.07); 2.6664 (1.47); 2.6618 (0.69); 2.5242 (6.15); 2.5194 (9.86); 2.5109 (118.38); 2.5064 (236); 2.5019 (308.89); 2.4973 (220.88); 2.4928 (104.15); 2.3376 (0.77); 2.3332 (1.55); 2.3287 (2.12); 2.3241 (1.53); 2.3197 (0.73); 1.3539 (0.92); 1.2983 (2.9); 1.2667 (6.51); 1.2586 (5.61); 1.2492 (14.43); 1.2316 (6.63); 0.008 (1.47); −0.0001 (44.94); −0.0085 (1.4)

Compound No. 42 [DMSO]
9.9557 (3.34); 9.9317 (3.4); 9.2945 (1.95); 9.2806 (4.16); 9.2666 (1.93); 8.3933 (16); 8.2086 (4.76); 8.0783 (2.52); 8.0591 (2.82); 7.9534 (0.54); 7.8422 (2.32); 7.8225 (3.33); 7.7462 (2.55); 7.7268 (3.91); 7.7073 (1.67); 7.4622 (13.37); 6.3756 (0.35); 6.3549 (1.31); 6.3332 (1.98); 6.3106 (1.43); 6.2886 (0.41); 4.583 (1.56); 4.5656 (4.88); 4.5479 (4.93); 4.5304 (1.58); 4.3814 (10.36); 4.3675 (10.31); 4.3551 (0.57); 3.3244 (91.85); 2.9298 (0.47); 2.8911 (4.23); 2.7319 (3.38); 2.6895 (3.46); 2.6761 (0.8); 2.6715 (1.05); 2.6669 (0.76); 2.6625 (0.36); 2.5248 (3.18); 2.5114 (61.5); 2.507 (120.64); 2.5025 (156.78); 2.4979 (112.79); 2.4935 (53.88); 2.3337 (0.78); 2.3293 (1.06); 2.3248 (0.76); 1.355 (0.86); 1.2987 (2.32); 1.2688 (6.77); 1.2584 (4.9); 1.2514 (15.06); 1.2337 (7.03); 0.0079 (0.77); −0.0002 (21.1); −0.0085 (0.69)

Compound No. 43 [DMSO]
9.9308 (1.22); 9.9067 (1.25); 8.5136 (1.08); 8.4935 (1.09); 8.3047 (0.53); 8.2781 (4.83); 8.2106 (1.88); 8.0791 (0.99); 8.0594 (1.09); 7.8416 (0.91); 7.822 (1.28); 7.7458 (0.97); 7.7263 (1.48); 7.7067 (0.64); 7.4441 (3.96); 6.3521 (0.5); 6.3299 (0.75); 6.3071 (0.53); 4.5795 (0.58); 4.5625 (1.71); 4.5447 (1.71); 4.5274 (0.57); 4.1339 (0.59); 4.1166 (0.69); 4.0975 (0.59); 3.325 (17.41); 2.8914 (0.51); 2.7315 (0.39); 2.7191 (0.59); 2.7029 (0.61); 2.6896 (1.3); 2.6863 (1.12); 2.6701 (1.12); 2.5995 (1.2); 2.582 (1.23); 2.5663 (0.82); 2.5488 (0.82); 2.5116 (15.54); 2.5073 (29.67); 2.5028 (38.36); 2.4983 (27.94); 2.494 (13.63); 2.1287 (16); 2.1187 (0.36); 2.105 (1.68); 1.299 (0.75); 1.2789 (0.73); 1.2591 (3.6); 1.2461 (6.97); 1.2424 (6.25); 1.2296 (5.92); −0.0002 (5.22)

Compound No. 44 [DMSO]
9.9541 (1.24); 9.9301 (1.28); 9.0055 (0.68); 8.991 (1.44); 8.9762 (0.68); 8.3111 (6.01); 8.2095 (1.81); 8.08 (0.97); 8.0605 (1.08); 7.842 (0.89); 7.8223 (1.29); 7.7463 (0.97); 7.7269 (1.49); 7.7073 (0.65); 7.4558 (5.02); 6.3534 (0.49); 6.331 (0.75); 6.3086 (0.55); 4.5799 (0.58); 4.5623 (1.83); 4.5446 (1.86); 4.527 (0.6); 4.0633 (3.48); 4.0484 (3.43); 3.6959 (16); 3.3249 (75.81); 2.8908 (0.75); 2.7312 (0.59); 2.6893 (0.36); 2.6757 (0.4); 2.6712 (0.54); 2.6666 (0.39); 2.5245 (1.8); 2.5111 (31.64); 2.5067 (61.92); 2.5021 (80.39); 2.4976 (58.02); 2.4931 (27.75); 2.3333 (0.39); 2.3288 (0.53); 2.3243 (0.38); 1.2985 (0.85); 1.266 (2.59); 1.2585 (1.71); 1.2485 (5.69); 1.2308 (2.55); 0.008 (0.39); −0.0002 (10.82); −0.0085 (0.37)

Compound No. 45 [DMSO]
9.982 (0.76); 9.9579 (0.99); 9.9434 (3.46); 9.9193 (3.52); 8.9942 (1.99); 8.9805 (4.08); 8.9666 (1.95); 8.7294 (3.13); 8.3146 (15.93); 8.2088 (6.02); 8.1404 (0.34); 8.0779 (3.2); 8.0584 (3.56); 7.841 (2.94); 7.8214 (4.19); 7.7452 (3.2); 7.7257 (4.89); 7.7061 (2.08); 7.4797 (2.97); 7.4445 (13.52); 6.3727 (0.44); 6.3515 (1.65); 6.3296 (2.49); 6.3072 (1.79); 6.2852 (0.5); 4.5778 (1.72); 4.5603 (5.33); 4.5516 (2.49); 4.5427 (5.39); 4.5254 (1.83); 4.0838 (6.07); 4.0775 (6.59); 4.07 (6.49); 4.0637 (6.03); 3.3243 (94.98); 3.1988 (3.23); 3.1926 (6.62); 3.1864 (3.05); 2.891 (1.71); 2.7318 (1.39); 2.6895 (1.07); 2.6804 (0.49); 2.6761 (0.97); 2.6716 (1.3); 2.667 (0.96); 2.6626 (0.46); 2.5247 (4.2); 2.5114 (74.67); 2.507 (146.27); 2.5025 (190.08); 2.4979 (137.65); 2.4935 (66.3); 2.3383 (0.48); 2.3337 (0.95); 2.3292 (1.29); 2.3246 (0.96); 1.3552 (1.22); 1.337 (0.36); 1.2986 (2.93); 1.2634 (7.72); 1.2587 (6.43); 1.2523 (6); 1.246 (16); 1.2346 (3.75); 1.2284 (7.17); 0.0079 (0.92); −0.0002 (25.48); −0.0085 (0.87)

Compound No. 46 [DMSO]
9.8971 (3.29); 9.8731 (3.39); 8.763 (3.28); 8.7439 (3.32); 8.3024 (16); 8.2923 (2.51); 8.1882 (1.29); 8.1813 (1.41); 8.1734 (1.65); 8.1658 (1.49); 8.1605 (1.44); 7.6918 (2.1); 7.666 (2.71); 7.6434 (1.96); 7.4274 (12.11); 6.4127 (0.34); 6.3918 (1.31); 6.3699 (1.96); 6.3474 (1.4); 6.3251 (0.4); 4.5818 (1.55); 4.5644 (4.67); 4.5468 (4.68); 4.5292 (1.5); 4.4103 (1.11); 4.3901 (2.16); 4.3702 (2.15); 4.35 (1.14); 3.3266 (16.03); 2.6736 (0.42); 2.5132 (25.49); 2.5089 (48.77); 2.5044 (62.84); 2.4999 (45.55); 2.4956 (22.08); 2.3312 (0.42); 2.3266 (0.32); 2.292 (0.69); 2.2831 (1.07); 2.2754 (1.58); 2.2637 (2.41); 2.2569 (2.64); 2.249 (2.52); 2.2461 (2.42); 2.2394 (2.13); 2.2361 (2.14); 2.2174 (0.89); 2.0634 (0.67); 2.0571 (0.55); 2.04 (2.16); 2.0346 (1.83); 2.0156 (3.14); 2.01 (2.92); 1.9911 (2.58); 1.9869 (2.4); 1.9703 (0.61); 1.9642 (0.73); 1.7289 (1.3); 1.7158 (2.58); 1.7053 (2.87); 1.6913 (3.7); 1.6825 (1.85); 1.6716 (1.68); 1.6651 (1.44); 1.6471 (0.6); 1.2657 (6.45); 1.2483 (13.96); 1.2306 (6.53); 1.1762 (0.4)

Compound No. 47 [DMSO]
9.9441 (2.96); 9.92 (3.11); 9.0864 (1.56); 9.0717 (3.36); 9.0568 (1.6); 8.8271 (15.27); 8.8148 (15.41); 8.3835 (16); 8.3313 (0.4); 8.2135 (4.2); 8.0834 (2.22); 8.064 (2.48); 7.844 (2.04); 7.8242 (2.92); 7.7484 (2.28); 7.7288 (3.48); 7.7092 (1.51); 7.4639 (12.62); 7.4514 (3.32); 7.4392 (6.2); 7.4269 (3.03); 6.3572 (1.14); 6.335 (1.72); 6.3124 (1.26); 6.291 (0.37); 4.6801 (7.5); 4.6654 (7.43); 4.5852 (1.34); 4.5679 (4.24); 4.5502 (4.3); 4.5326 (1.37); 3.3255 (90.78); 2.8911 (0.99); 2.7321 (0.81); 2.6895 (5.02); 2.6809 (0.35); 2.6761 (0.69); 2.6717 (0.92); 2.6671 (0.66); 2.6628 (0.32); 2.525 (2.54); 2.5202 (4.03); 2.5117 (48.81); 2.5072 (97.8); 2.5026 (128.57); 2.498 (92.41); 2.4935 (43.63); 2.334 (0.6); 2.3294 (0.84); 2.3248 (0.58); 1.9098 (0.45); 1.3529 (0.84); 1.2709 (6.04); 1.2534 (13.7); 1.2356 (7.02); 1.0453 (1.4); 1.0301 (1.39); 0.008 (0.34); −0.0002 (9.9)

Compound No. 48 [DMSO]

9.7699 (4.05); 9.7456 (4.19); 8.7654 (4.12); 8.7463 (4.15); 8.3033 (15.75); 8.121 (10.76); 8.1053 (10.82); 7.4364 (13.5); 6.3445 (0.45); 6.3234 (1.62); 6.302 (2.4); 6.2798 (1.75); 6.2578 (0.51); 5.7583 (0.94); 4.5818 (1.91); 4.5644 (5.47); 4.5465 (5.47); 4.529 (1.9); 4.4292 (0.34); 4.4087 (1.36); 4.3887 (2.65); 4.3687 (2.65); 4.3485 (1.43); 4.3286 (0.33); 3.3237 (39.39); 2.6762 (0.62); 2.6719 (0.85); 2.6679 (0.66); 2.5073 (98.49); 2.5029 (130.22); 2.4987 (101.24); 2.3296 (0.91); 2.3254 (0.74); 2.291 (0.91); 2.2813 (1.4); 2.2741 (2.03); 2.263 (3.12); 2.2561 (3.33); 2.2483 (3.2); 2.2359 (2.83); 2.2167 (1.18); 2.0869 (0.7); 2.0623 (0.86); 2.0558 (0.74); 2.038 (2.75); 2.0141 (3.94); 2.0089 (3.83); 1.9911 (2.75); 1.9857 (3); 1.9689 (0.8); 1.9629 (0.94); 1.7282 (1.62); 1.7149 (3.09); 1.7045 (3.53); 1.6906 (4.64); 1.6819 (2.45); 1.6708 (2.15); 1.6648 (1.9); 1.6466 (0.77); 1.4911 (0.35); 1.2724 (7.52); 1.2551 (16); 1.2373 (7.67); 1.1423 (0.46); 1.0454 (0.38); 1.0302 (0.39); −0.0002 (0.46)

Compound No. 49 [DMSO]

9.804 (3.22); 9.7798 (3.32); 8.762 (3.19); 8.743 (3.22); 8.2933 (16); 8.0942 (2.38); 8.0893 (2.54); 8.0765 (2.46); 8.0715 (2.45); 7.8173 (1.18); 7.8121 (1.26); 7.8061 (1.37); 7.7963 (1.6); 7.7906 (1.54); 7.7846 (1.5); 7.7793 (1.31); 7.569 (3.38); 7.5463 (5.06); 7.5242 (2.9); 7.4282 (12.99); 6.2745 (0.33); 6.2537 (1.25); 6.2316 (1.88); 6.209 (1.34); 6.1874 (0.39); 4.5812 (1.45); 4.5638 (4.47); 4.546 (4.47); 4.5285 (1.44); 4.407 (1.05); 4.3868 (2.08); 4.3668 (2.07); 4.3467 (1.09); 3.3229 (85.15); 2.6801 (0.46); 2.6755 (0.97); 2.671 (1.35); 2.6664 (0.98); 2.6619 (0.47); 2.5243 (4.07); 2.5195 (6.48); 2.511 (75.42); 2.5065 (150.85); 2.5019 (198.55); 2.4973 (143.13); 2.4928 (67.94); 2.3379 (0.45); 2.3332 (0.96); 2.3287 (1.33); 2.3241 (0.96); 2.3196 (0.47); 2.2897 (0.66); 2.2805 (0.99); 2.2731 (1.48); 2.2612 (2.23); 2.2545 (2.48); 2.2467 (2.36); 2.2436 (2.24); 2.2367 (1.97); 2.2337 (2.04); 2.215 (0.87); 2.0609 (0.63); 2.0542 (0.51); 2.0375 (2.04); 2.0315 (1.71); 2.0128 (2.96); 2.007 (2.75); 1.9901 (2.1); 1.984 (2.28); 1.9677 (0.59); 1.9614 (0.69); 1.7269 (1.24); 1.714 (2.46); 1.7035 (2.75); 1.6893 (3.56); 1.6802 (1.72); 1.6697 (1.56); 1.6631 (1.4); 1.6453 (0.59); 1.2653 (6.36); 1.2479 (14.38); 1.2302 (6.65); 0.1461 (0.53); 0.008 (4.74); −0.0002 (135.25); −0.0085 (4.27); −0.1496 (0.55)

Compound No. 50 [DMSO]

9.8984 (1.6); 9.8743 (1.66); 8.3971 (1.57); 8.3778 (1.59); 8.3066 (1.12); 8.2891 (1.13); 8.2753 (7.7); 8.1881 (0.6); 8.1818 (0.65); 8.1728 (0.79); 8.1666 (0.68); 8.1603 (0.66); 7.6925 (0.99); 7.6667 (1.27); 7.6442 (0.95); 7.4226 (6.21); 6.3917 (0.61); 6.3698 (0.93); 6.3473 (0.67); 4.5802 (0.72); 4.5628 (2.25); 4.5451 (2.25); 4.5274 (0.73); 4.0764 (0.66); 4.0598 (1); 4.0412 (0.98); 4.0244 (0.66); 3.3261 (10.77); 2.5264 (0.7); 2.5129 (13.3); 2.5085 (26.53); 2.504 (34.81); 2.4994 (25.25); 2.495 (12.21); 1.2641 (3.11); 1.2467 (6.92); 1.229 (3.2); 1.1793 (16); 1.1629 (15.83)

Compound No. 51 [DMSO]

9.9211 (0.56); 9.8971 (0.57); 8.4531 (0.46); 8.4415 (0.46); 8.3135 (2.68); 8.2093 (0.85); 8.0793 (0.44); 8.0599 (0.52); 7.9542 (2.16); 7.8408 (0.41); 7.8215 (0.6); 7.7454 (0.45); 7.726 (0.69); 7.4433 (2.24); 6.3294 (0.35); 4.5615 (0.88); 4.5439 (0.89); 3.3294 (7.19); 3.0477 (0.33); 2.9583 (1.19); 2.8917 (16); 2.8001 (2.71); 2.7886 (2.7); 2.7324 (13.14); 2.6901 (1.52); 2.5258 (0.38); 2.5125 (7.17); 2.508 (14.19); 2.5035 (18.53); 2.4989 (13.43); 2.4945 (6.43); 1.9099 (7.88); 1.2618 (1.29); 1.2444 (2.74); 1.2269 (1.34); −0.0002 (1.4)

Compound No. 52 [DMSO]

9.925 (2.39); 9.9008 (2.45); 8.5136 (1.24); 8.4999 (2.48); 8.486 (1.23); 8.2973 (12.04); 8.2099 (3.38); 8.0781 (1.81); 8.0588 (2); 7.841 (1.65); 7.8214 (2.36); 7.7453 (1.84); 7.7257 (2.83); 7.7061 (1.21); 7.4383 (9.85); 6.3509 (0.94); 6.3291 (1.43); 6.3066 (1.02); 4.5789 (1.12); 4.5614 (3.56); 4.5437 (3.59); 4.5264 (1.12); 3.3241 (57.43); 3.2974 (3.28); 3.2832 (3.52); 3.2793 (3.52); 3.2653 (3.29); 3.2473 (1.01); 2.891 (0.54); 2.7318 (0.42); 2.676 (0.54); 2.6714 (0.72); 2.6668 (0.52); 2.5248 (2.04); 2.5198 (3.27); 2.5114 (40.85); 2.5069 (81.6); 2.5024 (106.87); 2.4978 (76.66); 2.4933 (36.32); 2.3338 (0.52); 2.3291 (0.72); 2.3246 (0.51); 1.3537 (2.07); 1.2599 (5.08); 1.2424 (11.61); 1.2352 (3.73); 1.2248 (5.11); 1.159 (7.51); 1.1409 (16); 1.1229 (7.26); 0.9837 (0.43); 0.8534 (0.4); 0.008 (0.46); −0.0002 (14.26); −0.0085 (0.45)

Compound No. 53 [DMSO]

9.9208 (3.91); 9.8967 (4.01); 9.455 (8.74); 8.3917 (15.7); 8.3018 (2.95); 8.2876 (2.9); 8.1788 (1.86); 8.171 (2.1); 8.1634 (1.9); 7.6937 (2.45); 7.6681 (3.33); 7.6453 (2.28); 7.4417 (13.4); 6.4157 (0.43); 6.3954 (1.59); 6.3733 (2.39); 6.351 (1.7); 6.3293 (0.48); 5.7598 (0.79); 4.581 (1.84); 4.5636 (5.51); 4.546 (5.56); 4.5286 (1.86); 3.3278 (25.49); 2.8793 (2.5); 2.6784 (0.36); 2.6739 (0.47); 2.6697 (0.36); 2.5093 (58.3); 2.5049 (74.13); 2.5004 (55.37); 2.3362 (0.39); 2.3318 (0.5); 2.3272 (0.38); 2.0884 (4.81); 1.6297 (2.95); 1.6154 (7.49); 1.6087 (8.12); 1.5956 (3.39); 1.3461 (0.34); 1.306 (3.61); 1.2924 (7.78); 1.2859 (8.34); 1.2682 (8.57); 1.2505 (16); 1.2329 (7.89); 1.2061 (0.37); 1.1795 (0.57); 1.1583 (0.34); 1.143 (0.5); 1.1264 (1.24); 1.1142 (3.9); 1.107 (4.03); 1.096 (1.69); 0.8838 (1.83); 0.8728 (4.55); 0.8654 (4.55); 0.8534 (1.53); −0.0002 (0.39)

Compound No. 54 [DMSO]

9.8287 (3.19); 9.8046 (3.29); 8.7633 (3.32); 8.7442 (3.38); 8.2962 (15.76); 8.1161 (6.55); 7.7908 (0.52); 7.7715 (16); 7.747 (0.35); 7.433 (13.13); 6.2923 (0.35); 6.2713 (1.33); 6.2494 (1.99); 6.2272 (1.44); 6.205 (0.4); 4.5806 (1.53); 4.5634 (4.61); 4.5455 (4.63); 4.528 (1.5); 4.4085 (1.09); 4.3881 (2.16); 4.3681 (2.14); 4.3479 (1.15); 3.3244 (41.52); 2.6764 (0.51); 2.6718 (0.72); 2.6673 (0.5); 2.5249 (2.3); 2.5117 (42.37); 2.5072 (83.14); 2.5027 (107.95); 2.4981 (77.52); 2.4936 (36.95); 2.334 (0.55); 2.3294 (0.74); 2.3249 (0.53); 2.2905 (0.7); 2.2814 (1.05); 2.274 (1.55); 2.262 (2.38); 2.2554 (2.61); 2.2477 (2.49); 2.2446 (2.37); 2.2377 (2.08); 2.2347 (2.14); 2.2157 (0.92); 2.1772 (0.43); 2.0617 (0.66); 2.0555 (0.54); 2.0385 (2.13); 2.0326 (1.78); 2.0139 (3.13); 2.0081 (2.89); 1.9913 (2.2); 1.9852 (2.38); 1.9688 (0.63); 1.9626 (0.74); 1.7275 (1.31); 1.7146 (2.58); 1.704 (2.87); 1.69 (3.71); 1.6806 (1.84); 1.6703 (1.65); 1.6637 (1.47); 1.646 (0.64); 1.3556 (0.33); 1.3518 (0.41); 1.2987 (0.54); 1.2654 (6.77); 1.2587 (2.49); 1.2479 (15.08); 1.2336 (8.75); 1.2308 (8.71); 0.8531 (0.72); 0.0079 (2.63); −0.0002 (68.24); −0.0085 (2.3)

Compound No. 55 [DMSO]

9.9142 (2.48); 9.8902 (2.54); 9.1616 (1.28); 9.1468 (2.67); 9.1316 (1.25); 8.5436 (2.22); 8.5334 (2.18); 8.4105 (11.02); 8.3082 (1.73); 8.2946 (1.67); 8.1895 (0.94); 8.1839 (1.02); 8.1759 (1.18); 8.168 (1.06); 8.1623 (1.02); 7.8455 (1.35); 7.8411 (1.33); 7.8263 (2.7); 7.8218 (2.63); 7.8071 (1.61); 7.8026 (1.54); 7.6935 (1.55); 7.6678 (2.01); 7.6451 (1.42); 7.4905 (3.17); 7.4709 (2.84); 7.4451 (9.24); 7.3172 (1.65); 7.3047 (1.72); 7.3001 (1.65); 7.2877 (1.45); 6.3957 (0.95); 6.3739 (1.44); 6.3518 (1.02); 4.5899 (6.56); 4.5746 (7.21); 4.5533 (3.52); 4.5361 (1.14); 3.3251 (31.07); 2.8914 (1.96); 2.7321 (1.61); 2.6899 (16); 2.6766 (0.47); 2.6719 (0.6); 2.6676 (0.44); 2.5252 (2.09); 2.5118 (34.9); 2.5075 (67.69); 2.503 (87.83); 2.4984 (63.51); 2.494 (30.49); 2.3342 (0.43); 2.3297 (0.58); 2.3254 (0.42); 1.3368 (0.62); 1.2992 (0.7); 1.2773 (4.86); 1.2598 (11.14); 1.2494 (1.9); 1.2421 (5.02); −0.0002 (0.47)

Compound No. 56 [DMSO]
9.8309 (1.66); 9.8067 (1.71); 8.3983 (1.63); 8.3791 (1.63); 8.2702 (6.43); 8.1177 (3.38); 7.7714 (7.82); 7.4305 (5.83); 6.2724 (0.71); 6.2505 (1.07); 6.228 (0.76); 4.5815 (0.84); 4.5643 (2.41); 4.5465 (2.42); 4.5291 (0.82); 4.0769 (0.69); 4.0601 (1.08); 4.0414 (1.17); 4.0249 (0.76); 4.0221 (0.66); 3.3268 (12.53); 2.5084 (23.63); 2.504 (30.05); 2.4996 (22.63); 2.0877 (0.48); 1.9906 (1.49); 1.3553 (0.41); 1.2663 (3.29); 1.2489 (7.06); 1.2312 (3.49); 1.1936 (0.97); 1.1798 (16); 1.1633 (15.74); −0.0002 (15.73); −0.0084 (0.76)

Compound No. 57 [DMSO]
9.9296 (3.37); 9.9054 (3.42); 9.5319 (0.57); 9.5072 (0.56); 8.6041 (1.75); 8.5901 (3.55); 8.5759 (1.77); 8.4595 (0.59); 8.2905 (14.82); 8.2261 (0.38); 8.21 (5.21); 8.0787 (2.73); 8.0594 (3.29); 8.0449 (0.62); 7.9603 (2.56); 7.8409 (2.47); 7.8214 (3.74); 7.8075 (0.69); 7.7451 (2.66); 7.7256 (4.1); 7.7061 (1.8); 7.6937 (0.35); 7.4398 (12.48); 7.3008 (2.14); 6.3726 (0.37); 6.351 (1.37); 6.329 (2.09); 6.3067 (1.53); 6.2843 (0.53); 6.2759 (0.42); 4.58 (1.63); 4.5628 (4.99); 4.5451 (5.12); 4.5272 (1.92); 4.5044 (0.74); 4.0381 (0.75); 4.0202 (0.77); 3.8057 (0.38); 3.5072 (0.46); 3.3238 (107.99); 3.1806 (4.87); 3.1652 (7.88); 3.1497 (4.92); 3.1325 (0.9); 3.1167 (1.23); 3.1009 (0.81); 2.9878 (12.65); 2.9765 (0.79); 2.6756 (1.18); 2.6712 (1.53); 2.6667 (1.18); 2.6323 (0.39); 2.5243 (4.81); 2.5108 (85.93); 2.5066 (165.84); 2.5021 (213.48); 2.4976 (156.32); 2.3333 (1.11); 2.3289 (1.42); 2.3244 (1.07); 1.9892 (3.21); 1.3544 (3.11); 1.3357 (0.4); 1.2983 (0.63); 1.2615 (7.19); 1.2441 (16); 1.2267 (8.15); 1.2127 (1.58); 1.1926 (1.09); 1.1748 (1.89); 1.157 (0.98); 1.151 (0.42); 1.0845 (0.36); 1.071 (0.4); 1.0588 (0.7); 1.0544 (0.79); 1.0513 (0.81); 1.0391 (1.57); 1.0344 (1.37); 1.0305 (1.24); 1.0223 (2.2); 1.0143 (1.15); 1.01 (1.33); 1.006 (1.37); 1.0024 (1.27); 0.9902 (0.69); 0.9859 (0.53); 0.8676 (0.39); 0.8532 (0.59); 0.8426 (0.33); 0.8352 (0.4); 0.4798 (1.72); 0.4689 (5.44); 0.4647 (5.82); 0.4598 (2.95); 0.4545 (3.58); 0.4487 (5.9); 0.4446 (5.43); 0.4346 (2.74); 0.4218 (0.42); 0.2731 (2.12); 0.2623 (6.43); 0.2596 (6.62); 0.2474 (7.34); 0.2361 (2.52); 0.146 (0.49); 0.0078 (4.22); −0.0003 (109.19); −0.0085 (4.87); −0.1496 (0.48)

Compound No. 58 [DMSO]
9.8235 (3.38); 9.7993 (3.48); 9.1632 (1.72); 9.1484 (3.62); 9.1333 (1.72); 8.5454 (2.86); 8.5435 (2.95); 8.5415 (2.56); 8.5334 (2.93); 8.5315 (2.84); 8.4044 (16); 8.0979 (2.49); 8.0929 (2.63); 8.0803 (2.55); 8.0753 (2.55); 7.8454 (1.88); 7.8409 (1.89); 7.8261 (4.04); 7.8217 (4.83); 7.8069 (3.47); 7.8024 (3.68); 7.7948 (1.7); 7.789 (1.6); 7.7836 (1.39); 7.5709 (3.36); 7.5484 (5.13); 7.5261 (2.92); 7.4909 (4.23); 7.4713 (3.81); 7.4499 (12.78); 7.3184 (2.18); 7.3167 (2.18); 7.3044 (2.31); 7.3001 (2.26); 7.2877 (2.01); 6.2813 (0.35); 6.2599 (1.3); 6.2382 (1.95); 6.2156 (1.4); 6.1936 (0.42); 4.5907 (8.84); 4.5752 (11.43); 4.5565 (4.68); 4.5389 (1.55); 4.3485 (0.47); 4.3382 (0.49); 3.5071 (0.4); 3.3263 (61.58); 2.8914 (0.72); 2.7319 (0.57); 2.6898 (1.11); 2.6766 (0.48); 2.672 (0.63); 2.6675 (0.45); 2.5252 (2.15); 2.5119 (37.31); 2.5075 (73.2); 2.503 (95.43); 2.4984 (69.38); 2.494 (33.78); 2.3341 (0.49); 2.3297 (0.66); 2.3252 (0.48); 1.2992 (1.9); 1.2807 (6.48); 1.2632 (14.47); 1.2455 (6.76); 1.2351 (1.79); 1.0525 (0.39); 1.0457 (3.73); 1.0304 (3.67); 0.8526 (0.44); 0.0079 (1); −0.0002 (25.78); −0.0085 (0.95)

Compound No. 59 [DMSO]
9.9363 (0.6); 9.9125 (0.63); 9.1689 (0.32); 9.1541 (0.68); 9.1391 (0.33); 8.5455 (0.54); 8.5438 (0.55); 8.5336 (0.55); 8.426 (2.85); 8.2789 (0.35); 8.2604 (0.64); 8.242 (0.35); 7.9539 (2.16); 7.8458 (0.34); 7.8413 (0.34); 7.8265 (0.67); 7.8221 (0.67); 7.8074 (0.4); 7.8029 (0.4); 7.4904 (0.85); 7.4802 (2.43); 7.4709 (0.77); 7.3175 (0.41); 7.3054 (0.43); 7.3008 (0.42); 7.2881 (0.37); 6.3677 (0.36); 4.5915 (1.59); 4.5763 (1.68); 4.5535 (0.85); 3.3277 (12.55); 2.8921 (16); 2.7327 (13.31); 2.6903 (7.52); 2.5256 (0.47); 2.5122 (7.4); 2.5078 (14.45); 2.5033 (18.87); 2.4988 (13.83); 2.4945 (6.84); 1.2892 (1.18); 1.2717 (2.57); 1.254 (1.17); −0.0002 (5.03)

Compound No. 60 [DMSO]
9.7887 (3.63); 9.7644 (3.71); 9.164 (1.92); 9.1492 (4); 9.1342 (1.92); 8.5452 (3.17); 8.5434 (3.24); 8.5333 (3.21); 8.5315 (3.11); 8.4127 (16); 8.317 (0.33); 8.1229 (9.71); 8.1071 (9.68); 7.8453 (2); 7.8408 (2); 7.826 (4); 7.8216 (3.92); 7.8069 (2.39); 7.8024 (2.3); 7.4903 (4.69); 7.4706 (4.34); 7.4573 (13.19); 7.3186 (2.46); 7.3045 (2.54); 7.3002 (2.48); 7.2877 (2.15); 6.3495 (0.38); 6.3286 (1.38); 6.3073 (2.02); 6.2845 (1.48); 6.2632 (0.44); 4.5904 (9.73); 4.5749 (12); 4.5555 (4.91); 4.538 (1.69); 3.3237 (89.32); 2.6806 (0.51); 2.6761 (0.99); 2.6715 (1.34); 2.6671 (0.98); 2.5247 (4.8); 2.5114 (76.82); 2.507 (148.45); 2.5025 (191.82); 2.498 (138.95); 2.4936 (67.72); 2.3338 (0.96); 2.3293 (1.28); 2.3247 (0.93); 1.286 (6.99); 1.2685 (15.35); 1.2508 (6.96); 1.0453 (1.84); 1.03 (1.8); 0.0079 (1.99); −0.0001 (48.91); −0.0083 (1.87)

Compound No. 61 [DMSO]
11.3155 (8.54); 9.9694 (3.96); 9.9454 (4.11); 8.5556 (16); 8.4377 (4.99); 8.4313 (5.04); 8.2824 (2.4); 8.2601 (2.8); 8.2153 (5.88); 8.0877 (3.14); 8.0682 (3.49); 8.0219 (4.23); 8.0153 (4.04); 7.9997 (3.54); 7.9931 (3.48); 7.8439 (2.84); 7.8243 (4.12); 7.7514 (3.07); 7.7318 (4.74); 7.7122 (1.97); 7.6017 (14.49); 6.3989 (0.41); 6.3776 (1.57); 6.3557 (2.38); 6.3333 (1.7); 6.311 (0.49); 5.3974 (9.22); 5.3922 (9.23); 4.0388 (0.38); 4.0211 (0.38); 3.3282 (55.17); 3.1862 (3.62); 3.1803 (7.67); 3.1744 (3.49); 2.6768 (0.49); 2.6723 (0.65); 2.668 (0.49); 2.512 (37.52); 2.5079 (72.82); 2.5034 (94.41); 2.4989 (68.92); 2.4949 (33.96); 2.3343 (0.44); 2.3302 (0.61); 2.3256 (0.44); 1.99 (1.69); 1.3374 (2.64); 1.2997 (0.4); 1.2589 (0.78); 1.2498 (1.87); 1.2356 (3.03); 1.1933 (0.62); 1.1882 (0.49); 1.1755 (0.98); 1.1577 (0.51); 0.8701 (0.35); 0.8535 (0.9); 0.8356 (0.53); 0.0079 (1.69); −0.0002 (43.01); −0.0085 (1.56)

Compound No. 62 [DMSO]
11.2935 (7.48); 9.9295 (3.15); 9.9058 (3.22); 8.5193 (14.37); 8.4341 (5.07); 8.4279 (5.08); 8.2772 (4.4); 8.2585 (5.08); 8.2411 (2.21); 8.0161 (4.37); 8.0095 (4.14); 7.9939 (3.64); 7.9872 (3.57); 7.5087 (11.48); 6.413 (0.38); 6.393 (1.37); 6.3718 (2.05); 6.35 (1.49); 6.3288 (0.44); 5.7575 (2.63); 4.6043 (1.65); 4.587 (4.83); 4.5691 (4.82); 4.5517 (1.63); 4.3481 (0.41); 4.0386 (0.69); 4.0208 (0.69); 3.4561 (0.37); 3.4434 (0.4); 3.4387 (0.39); 3.426 (0.37); 3.3246 (86); 2.6765 (0.78); 2.6721 (1.05); 2.6675 (0.77); 2.5252 (3.49); 2.5118 (62.27); 2.5075 (121.58); 2.503 (157.65); 2.4984 (114.22); 2.4941 (55.27); 2.3342 (0.78); 2.3298 (1.04); 2.3253 (0.75); 1.9897 (2.99); 1.3553 (0.34); 1.3363 (2.49); 1.3033 (7.35); 1.2859 (16); 1.2682 (7.37); 1.2496 (3.28); 1.2349 (1.18); 1.1934 (0.97); 1.1879 (0.73); 1.1756 (1.68); 1.1578 (0.85); 1.0738 (0.97); 1.0563 (1.9); 1.0388 (0.93); 0.8601 (0.82); 0.8537 (0.38); 0.8431 (0.35); 0.0079 (1.49); −0.0002 (40.52); −0.0085 (1.4)

Compound No. 63 [DMSO]
9.8884 (3.36); 9.8646 (3.51); 9.7821 (3.16); 9.0064 (7.53); 8.8995 (3.16); 8.6145 (13.27); 8.2645 (1.98); 8.246 (3.61); 8.2276 (1.92); 7.4687 (11.69); 6.8706 (1.24); 6.642 (0.68); 6.4091 (0.36); 6.3886 (1.4); 6.3675 (2.09); 6.3459 (1.53); 6.3248 (0.44); 4.575 (1.56); 4.5576 (4.63); 4.5398 (4.63); 4.5223 (1.55); 3.3226 (66.26); 3.1753 (0.54); 3.1621 (0.52); 2.6759 (0.93); 2.6715 (1.26); 2.6672 (0.93); 2.5244 (3.92); 2.5068 (146.57); 2.5024 (188.14); 2.4981 (138.91); 2.3335 (0.95); 2.3292 (1.26); 2.3249 (0.95); 2.1837 (1.96); 1.8728 (2.65); 1.863 (6); 1.8538 (6.51); 1.8446 (2.7); 1.3556 (13.7);

1.2702 (10.6); 1.2539 (16); 1.2362 (6.87); 0.1461 (0.44); 0.0078 (3.79); −0.0002 (95.53); −0.0083 (3.85); −0.1495 (0.45)

Compound No. 64 [DMSO]

9.7823 (2.5); 9.7464 (2.8); 9.722 (2.81); 9.0044 (5.96); 8.9024 (2.42); 8.6092 (11.87); 8.1155 (7.5); 8.0997 (7.41); 7.4496 (9.98); 6.8709 (1.34); 6.6427 (0.73); 6.3307 (1.06); 6.3092 (1.56); 6.287 (1.14); 6.2654 (0.33); 4.578 (1.26); 4.561 (3.61); 4.5433 (3.58); 4.5259 (1.2); 3.6185 (0.35); 3.6019 (0.84); 3.5959 (0.34); 3.5854 (0.33); 3.3243 (47.11); 2.6764 (0.52); 2.6721 (0.7); 2.6676 (0.49); 2.5119 (44.96); 2.5076 (84.05); 2.5031 (106.31); 2.4985 (76.35); 2.4941 (36.98); 2.3344 (0.55); 2.3298 (0.7); 2.3254 (0.51); 2.1839 (2.11); 1.8743 (2.24); 1.864 (4.85); 1.855 (5.11); 1.8454 (2.14); 1.777 (0.39); 1.7694 (0.41); 1.7605 (1.02); 1.7519 (0.38); 1.744 (0.34); 1.3559 (16); 1.3372 (0.32); 1.279 (2.98); 1.2695 (10.22); 1.2599 (6.87); 1.2522 (12.75); 1.2346 (5.43); 0.0079 (2.99); −0.0002 (64.72); −0.0085 (2.65)

Compound No. 65 [DMSO]

9.7887 (1.71); 9.7816 (1.25); 9.7649 (1.46); 9.0082 (2.79); 8.9087 (1.06); 8.6053 (6.24); 8.0931 (0.93); 8.0881 (0.98); 8.0756 (0.96); 8.0704 (0.94); 7.9543 (2.02); 7.8203 (0.46); 7.8153 (0.5); 7.8092 (0.54); 7.8031 (0.57); 7.7993 (0.62); 7.7936 (0.6); 7.7877 (0.58); 7.7825 (0.5); 7.5727 (1.28); 7.5502 (1.92); 7.528 (1.1); 7.4517 (4.78); 6.8712 (0.46); 6.2628 (0.47); 6.2411 (0.71); 6.2185 (0.51); 5.7575 (0.5); 4.5808 (0.54); 4.5635 (1.63); 4.5458 (1.63); 4.5284 (0.53); 3.6021 (0.45); 3.3266 (16.48); 2.8923 (16); 2.7333 (12.94); 2.7325 (12.61); 2.526 (0.82); 2.5127 (12.84); 2.5083 (24.83); 2.5037 (31.92); 2.4991 (22.76); 2.4946 (10.71); 2.1843 (0.75); 1.8743 (0.99); 1.8639 (2.15); 1.8549 (2.28); 1.8453 (0.93); 1.7604 (0.56); 1.3564 (5.73); 1.2794 (1.13); 1.2687 (2.93); 1.2647 (3.6); 1.261 (3.03); 1.2473 (5.58); 1.2295 (2.38); 0.0079 (0.87); −0.0002 (20.39); −0.0085 (0.65)

Compound No. 66 [DMSO]

9.8757 (3.1); 9.8516 (3.24); 9.7841 (2.6); 9.0037 (6.89); 8.9027 (2.59); 8.6104 (14.89); 8.2985 (2.11); 8.285 (2.03); 8.1909 (1.08); 8.1854 (1.15); 8.1795 (1.25); 8.1704 (1.45); 8.1641 (1.3); 8.1576 (1.28); 7.9548 (1.96); 7.696 (1.89); 7.6701 (2.4); 7.6476 (1.77); 7.4381 (11.86); 6.8718 (0.78); 6.6441 (0.44); 6.3995 (1.16); 6.3775 (1.73); 6.3551 (1.25); 6.3329 (0.36); 5.7584 (1.18); 4.5772 (1.29); 4.5598 (4.04); 4.5422 (4.06); 4.5247 (1.31); 3.6024 (0.76); 3.5858 (0.33); 3.327 (35.67); 3.1771 (0.59); 3.164 (0.57); 2.8927 (16); 2.7336 (12.88); 2.6908 (4.63); 2.6779 (0.39); 2.6732 (0.52); 2.6686 (0.38); 2.5265 (1.68); 2.5132 (30.07); 2.5087 (59.46); 2.5041 (77.53); 2.4995 (55.44); 2.4951 (26.23); 2.3355 (0.38); 2.3309 (0.51); 2.3264 (0.37); 2.1846 (1.24); 1.8752 (2.42); 1.8649 (5.32); 1.8559 (5.73); 1.8463 (2.31); 1.7771 (0.33); 1.7691 (0.33); 1.7607 (0.93); 1.7518 (0.32); 1.7441 (0.32); 1.3567 (9.64); 1.2789 (2.66); 1.2686 (6.48); 1.2617 (9.83); 1.2448 (13.53); 1.2271 (5.9); −0.0002 (6.51)

Compound No. 67 [DMSO]

9.8374 (1.73); 9.8133 (1.77); 8.4493 (1.85); 8.4385 (1.86); 8.2107 (2.5); 8.1242 (6.89); 8.0786 (1.45); 8.0594 (1.5); 7.8351 (1.24); 7.8155 (1.79); 7.7437 (1.37); 7.7242 (2.09); 7.7047 (0.86); 7.4666 (7.1); 7.3099 (0.47); 6.3538 (0.69); 6.3317 (1.04); 6.3093 (0.76); 5.3976 (4.38); 5.3919 (4.35); 3.3281 (14); 3.0686 (1.63); 3.0626 (3.6); 3.0568 (1.52); 2.8817 (0.58); 2.8719 (0.77); 2.8636 (1.24); 2.8534 (1.25); 2.8452 (0.77); 2.8353 (0.61); 2.6209 (16); 2.5981 (0.38); 2.5259 (0.54); 2.5211 (0.81); 2.5124 (10.25); 2.5079 (20.98); 2.5034 (27.77); 2.4988 (19.87); 2.4942 (9.38); 1.99 (1.05); 1.9111 (0.52); 1.1757 (0.6); 0.7405 (0.82); 0.7277 (2.11); 0.7225 (3.07); 0.7105 (2.76); 0.7044 (2.39); 0.6931 (1); 0.5753 (1.05); 0.5648 (3); 0.5588 (2.66); 0.5546 (2.51); 0.5492 (2.43); 0.5369 (0.76); −0.0002 (5.64)

Compound No. 68 [DMSO]

9.8059 (3.22); 9.7816 (3.33); 8.5909 (3.59); 8.5801 (3.63); 8.4343 (0.41); 8.3454 (16); 8.2931 (0.33); 8.114 (9.23); 8.0982 (9.3); 7.5455 (0.63); 7.5352 (13.62); 6.3549 (0.34); 6.3345 (1.25); 6.313 (1.85); 6.2905 (1.38); 6.2691 (0.44); 5.3635 (8.17); 5.3579 (8.09); 4.0394 (0.56); 4.0216 (0.57); 3.3264 (18.57); 3.1703 (2.96); 3.1645 (6.39); 3.1586 (2.83); 2.8826 (0.39); 2.8727 (1.09); 2.863 (1.45); 2.8545 (2.35); 2.8444 (2.39); 2.836 (1.45); 2.8263 (1.11); 2.8163 (0.43); 2.6733 (0.4); 2.5266 (1.23); 2.5217 (1.93); 2.5132 (23.29); 2.5087 (47.34); 2.5041 (62.4); 2.4996 (44.59); 2.4951 (21.03); 2.3309 (0.39); 2.1808 (0.6); 2.1623 (0.33); 1.9904 (2.5); 1.911 (0.61); 1.2341 (8.49); 1.1943 (0.74); 1.1765 (1.39); 1.1587 (0.68); 0.8704 (0.33); 0.8535 (0.98); 0.8358 (0.38); 0.752 (1.53); 0.739 (4.11); 0.734 (5.86); 0.7218 (5.34); 0.7159 (4.61); 0.7045 (1.82); 0.5688 (1.99); 0.5581 (5.6); 0.5522 (5.13); 0.548 (4.79); 0.5427 (4.75); 0.5303 (1.46); 0.008 (0.42); −0.0002 (12.41); −0.0085 (0.4)

Compound No. 69 [DMSO]

9.9646 (3.1); 9.9409 (3.18); 8.5912 (3.76); 8.5804 (3.75); 8.4428 (0.46); 8.3539 (16); 8.3159 (0.66); 8.2578 (1.89); 8.2393 (3.41); 8.2208 (1.84); 7.5554 (0.52); 7.5415 (12.82); 6.3953 (0.37); 6.375 (1.29); 6.3539 (1.87); 6.332 (1.37); 6.3107 (0.41); 5.3478 (8.2); 5.3422 (8.07); 4.0379 (0.51); 4.0201 (0.52); 3.6181 (1.05); 3.6118 (0.69); 3.6077 (0.91); 3.6015 (2.56); 3.5954 (0.96); 3.5913 (0.68); 3.5849 (1.06); 3.3227 (145.55); 3.1787 (3.25); 3.1728 (7.46); 3.1668 (3.08); 2.879 (0.38); 2.8691 (1.07); 2.8597 (1.46); 2.8508 (2.35); 2.8407 (2.32); 2.8325 (1.46); 2.8227 (1.11); 2.8125 (0.42); 2.6755 (1.3); 2.6709 (1.78); 2.6664 (1.29); 2.662 (0.61); 2.5243 (5.17); 2.5194 (8.06); 2.5109 (103.14); 2.5064 (208.96); 2.5019 (275.02); 2.4973 (197.11); 2.4928 (93.66); 2.3377 (0.62); 2.3332 (1.27); 2.3286 (1.74); 2.3241 (1.24); 2.3194 (0.61); 2.1795 (0.44); 1.9889 (2.29); 1.9086 (0.56); 1.7768 (1.09); 1.769 (1.09); 1.7603 (3.12); 1.7515 (1.1); 1.7438 (1.05); 1.3552 (1.37); 1.235 (8.03); 1.1928 (0.66); 1.175 (1.25); 1.1572 (0.59); 0.8538 (0.9); 0.8368 (0.33); 0.75 (1.46); 0.7372 (4.09); 0.732 (5.78); 0.7199 (5.36); 0.714 (4.56); 0.7025 (1.8); 0.5645 (1.89); 0.5539 (5.49); 0.5478 (5.09); 0.5437 (4.73); 0.5383 (4.72); 0.5261 (1.47); 0.008 (1.31); −0.0002 (42.33); −0.0085 (1.47)

Compound No. 70 [DMSO]

9.9235 (3.36); 9.8994 (3.48); 8.5867 (3.74); 8.5749 (3.8); 8.4312 (0.41); 8.3428 (16); 8.3167 (0.32); 8.2987 (2.37); 8.286 (2.48); 8.1875 (1.21); 8.182 (1.29); 8.176 (1.43); 8.1682 (1.66); 8.1604 (1.5); 8.1548 (1.46); 7.69 (2.2); 7.6644 (2.79); 7.6415 (2.06); 7.5261 (13.25); 6.4214 (0.38); 6.3999 (1.34); 6.3782 (2.01); 6.3558 (1.46); 6.3333 (0.44); 5.7571 (0.33); 5.3612 (8.2); 5.3559 (8.14); 4.0388 (0.7); 4.0209 (0.71); 3.3249 (33.99); 3.1602 (3.13); 3.1543 (6.71); 3.1484 (2.94); 2.8801 (0.38); 2.87 (1.08); 2.8607 (1.48); 2.8519 (2.35); 2.8418 (2.38); 2.8335 (1.51); 2.8238 (1.11); 2.8136 (0.41); 2.6766 (0.48); 2.672 (0.66); 2.6676 (0.48); 2.5254 (1.93); 2.5119 (39.68); 2.5075 (78.82); 2.503 (102.48); 2.4985 (73.55); 2.4941 (35.22); 2.3344 (0.5); 2.3298 (0.68); 2.3252 (0.5); 1.9896 (3.1); 1.2347 (1.04); 1.1934 (0.85); 1.1756 (1.67); 1.1578 (0.82); 0.7501 (1.5); 0.7372 (4.25); 0.7321 (5.94); 0.7199 (5.5); 0.7141 (4.71); 0.7026 (1.84); 0.5664 (1.97); 0.5558 (5.69); 0.5498 (5.37); 0.5458 (4.95); 0.5403 (4.91); 0.5279 (1.49); 0.0079 (2.14); −0.0002 (61.37); −0.0085 (2.13)

Compound No. 71 [DMSO]

9.7857 (1.7); 9.7618 (1.77); 8.4237 (1.85); 8.413 (1.87); 8.2923 (1.02); 8.2736 (1.82); 8.2552 (0.99); 8.0908 (6.7); 7.3749 (6.76); 6.3872 (0.7); 6.366 (1.01); 6.344 (0.75); 4.6176 (0.74); 4.6013 (1.79); 4.5972 (1.71); 4.5836 (1.66); 4.5794 (1.81); 4.5628 (0.7); 4.0388 (0.78); 4.021 (0.8);

3.3249 (22.24); 2.8766 (0.55); 2.8672 (0.77); 2.8585 (1.2); 2.8485 (1.22); 2.8398 (0.76); 2.8304 (0.58); 2.6723 (0.33); 2.607 (16); 2.5255 (0.98); 2.5121 (19.48); 2.5078 (38.83); 2.5032 (50.8); 2.4987 (36.66); 2.4943 (17.65); 2.3301 (0.33); 1.9899 (3.44); 1.2508 (3.35); 1.2335 (7.39); 1.2158 (3.27); 1.1938 (0.98); 1.176 (1.85); 1.1582 (0.93); 0.7355 (0.77); 0.7227 (2.14); 0.7176 (2.99); 0.7055 (2.74); 0.6995 (2.34); 0.6883 (0.98); 0.5688 (1.02); 0.5582 (2.99); 0.5521 (2.63); 0.5483 (2.5); 0.5426 (2.39); 0.5305 (0.74); −0.0002 (2.08)

Compound No. 72 [DMSO]

9.6406 (1.69); 9.6164 (1.76); 8.4181 (1.79); 8.4074 (1.8); 8.121 (4.76); 8.1051 (4.78); 8.0796 (6.7); 7.3506 (6.55); 6.3115 (0.66); 6.2898 (0.96); 6.2673 (0.71); 4.6202 (0.71); 4.6041 (1.72); 4.5998 (1.62); 4.5865 (1.59); 4.5819 (1.72); 4.5652 (0.68); 3.3236 (22.6); 2.8762 (0.54); 2.8667 (0.75); 2.8582 (1.19); 2.8482 (1.2); 2.8395 (0.75); 2.83 (0.57); 2.6765 (0.39); 2.6718 (0.53); 2.6672 (0.37); 2.6063 (16); 2.5252 (1.43); 2.5203 (2.19); 2.5117 (30.73); 2.5073 (62.02); 2.5028 (81.32); 2.4982 (58.17); 2.4937 (27.68); 2.334 (0.38); 2.3294 (0.53); 2.3251 (0.37); 1.9895 (0.88); 1.2481 (3.32); 1.2307 (7.39); 1.213 (3.27); 1.1756 (0.5); 0.7346 (0.76); 0.7219 (2.1); 0.7166 (2.93); 0.7046 (2.69); 0.6986 (2.27); 0.6874 (0.93); 0.5689 (0.99); 0.5584 (2.94); 0.5524 (2.56); 0.5483 (2.41); 0.5428 (2.33); 0.5306 (0.71); −0.0002 (4.74)

Compound No. 73 [DMSO]

10.0673 (3.67); 10.0433 (3.77); 8.6092 (3.98); 8.5989 (3.97); 8.3976 (11.28); 8.3166 (0.44); 8.217 (5.15); 8.0872 (2.78); 8.0675 (3.08); 7.846 (2.57); 7.8262 (3.69); 7.751 (2.82); 7.7317 (4.34); 7.7121 (1.79); 7.4876 (0.86); 7.4795 (14.66); 6.3969 (0.39); 6.3753 (1.44); 6.3534 (2.17); 6.3312 (1.54); 6.3093 (0.43); 4.6408 (1.65); 4.6234 (5.23); 4.6057 (5.26); 4.5881 (1.64); 4.0562 (0.34); 4.0384 (1.03); 4.0206 (1.04); 4.0029 (0.34); 3.3241 (74.45); 2.8537 (0.39); 2.8437 (1.17); 2.8343 (1.7); 2.8255 (2.55); 2.8158 (2.57); 2.8071 (1.67); 2.7977 (1.2); 2.7879 (0.43); 2.6763 (0.74); 2.6717 (1.02); 2.6672 (0.74); 2.6626 (0.36); 2.525 (3.19); 2.5201 (4.9); 2.5116 (59.1); 2.5072 (119.7); 2.5026 (157.89); 2.498 (113.46); 2.4935 (54.31); 2.3383 (0.38); 2.3339 (0.77); 2.3294 (1.06); 2.3248 (0.79); 1.9893 (4.58); 1.2938 (0.55); 1.2754 (7.19); 1.2579 (16); 1.2402 (7.21); 1.1932 (1.29); 1.1754 (2.5); 1.1576 (1.24); 0.7443 (1.68); 0.7315 (4.65); 0.7264 (6.35); 0.7142 (6.06); 0.7085 (4.98); 0.6969 (2.01); 0.5386 (2.07); 0.5278 (5.94); 0.5219 (5.61); 0.5179 (5.27); 0.5124 (5.24); 0.5002 (1.67); 0.3876 (0.33); −0.0002 (8.43)

Compound No. 74 [DMSO]

10.0981 (2.64); 10.074 (2.67); 9.5205 (5.72); 8.4803 (7.88); 8.3161 (0.73); 8.2138 (3.92); 8.0848 (2.09); 8.0648 (2.31); 7.8471 (1.9); 7.8275 (2.73); 7.7526 (2.03); 7.7328 (3.08); 7.7132 (1.29); 7.4884 (9.62); 6.3799 (1.07); 6.3574 (1.59); 6.3356 (1.14); 5.7565 (3.57); 4.6442 (1.2); 4.6269 (3.67); 4.6091 (3.69); 4.5914 (1.19); 3.5043 (0.85); 3.3217 (113.32); 2.6752 (1.93); 2.6708 (2.56); 2.6665 (1.89); 2.5239 (8.04); 2.5103 (154.2); 2.5062 (301.12); 2.5018 (390.67); 2.4973 (287.28); 2.3329 (1.89); 2.3285 (2.56); 2.3239 (1.88); 1.6262 (1.97); 1.6118 (4.91); 1.6052 (5.28); 1.5921 (2.19); 1.3522 (2.07); 1.3178 (0.4); 1.2978 (0.72); 1.2824 (5.76); 1.2651 (16); 1.2588 (7.86); 1.2472 (6.64); 1.2357 (3.97); 1.2087 (0.39); 0.8707 (0.56); 0.8534 (0.75); 0.8365 (0.34); 0.0078 (0.68); −0.0002 (18.93); −0.0084 (0.8)

Compound No. 75 [DMSO]

9.8082 (1.76); 9.7841 (1.82); 9.2852 (3.73); 8.3009 (1.24); 8.2876 (1.19); 8.1761 (7.15); 8.1531 (0.95); 7.687 (1.11); 7.6613 (1.42); 7.6387 (1.04); 7.3538 (6.41); 6.8717 (1.03); 6.6426 (0.58); 6.3822 (0.71); 6.3603 (1.04); 6.3381 (0.75); 5.7571 (1.79); 4.6217 (0.81); 4.6045 (2.24); 4.5864 (2.2); 4.5689 (0.77); 3.6271 (0.51); 3.6229 (1.12); 3.6192 (4.44); 3.6129 (2.98); 3.6088 (4.12); 3.6026 (10.84); 3.5966 (4.16); 3.5925 (2.88); 3.5861 (4.46); 3.5823 (1.07); 3.3259 (16.96); 2.673 (0.37); 2.6404 (1.05); 2.6291 (16); 2.5264 (1.18); 2.5215 (1.76); 2.5129 (20.06); 2.5085 (39.79); 2.504 (51.74); 2.4994 (36.91); 2.495 (17.56); 2.3307 (0.33); 2.1845 (1.65); 1.7949 (0.46); 1.7775 (4.66); 1.7697 (4.89); 1.761 (13.17); 1.7559 (3.42); 1.7523 (4.77); 1.7445 (4.35); 1.7273 (0.42); 1.6039 (1.33); 1.5897 (3.28); 1.5829 (3.57); 1.5699 (1.59); 1.3569 (12.4); 1.3213 (1.86); 1.308 (3.52); 1.3012 (3.7); 1.2869 (1.53); 1.2719 (0.41); 1.2488 (3.62); 1.2314 (7.92); 1.2137 (3.35); 1.1362 (0.39); 1.1071 (0.43); −0.0002 (5.67)

Compound No. 76 [DMSO]

9.7718 (1.83); 9.7476 (1.88); 8.4157 (1.95); 8.405 (1.96); 8.3037 (1.29); 8.2897 (1.26); 8.1844 (0.71); 8.1785 (0.78); 8.17 (0.9); 8.1627 (0.81); 8.1568 (0.8); 8.0778 (6.78); 7.6853 (1.14); 7.6595 (1.47); 7.6369 (1.06); 7.3398 (6.68); 6.3773 (0.72); 6.3554 (1.09); 6.3329 (0.78); 4.6185 (0.84); 4.6013 (2.33); 4.5831 (2.31); 4.5658 (0.81); 3.3265 (11.88); 2.8771 (0.57); 2.8676 (0.8); 2.8588 (1.23); 2.8489 (1.25); 2.8405 (0.8); 2.8307 (0.6); 2.6075 (16); 2.5262 (0.95); 2.5129 (16.71); 2.5085 (32.73); 2.504 (42.39); 2.4995 (30.7); 2.4951 (15.03); 1.9904 (1.05); 1.2411 (3.48); 1.2237 (7.47); 1.2061 (3.35); 1.1941 (0.45); 1.1763 (0.6); 0.7348 (0.79); 0.7219 (2.22); 0.7169 (3.06); 0.7048 (2.83); 0.6989 (2.41); 0.6876 (0.99); 0.5702 (1.04); 0.5595 (3.08); 0.5535 (2.78); 0.5497 (2.63); 0.544 (2.51); 0.5317 (0.75); −0.0002 (1.51)

Compound No. 77 [DMSO]

9.9406 (3.45); 9.9163 (3.55); 9.526 (7.93); 8.4825 (10.77); 8.3157 (0.52); 8.1236 (9.37); 8.1078 (9.36); 7.4922 (14.5); 6.3718 (0.35); 6.3518 (1.26); 6.33 (1.87); 6.3073 (1.38); 6.286 (0.42); 4.649 (1.52); 4.6317 (4.37); 4.6134 (4.33); 4.5959 (1.45); 3.3218 (69.46); 2.6763 (0.73); 2.6719 (0.98); 2.6673 (0.71); 2.542 (0.58); 2.5253 (2.61); 2.5205 (4.08); 2.5119 (56.36); 2.5074 (115.12); 2.5028 (151.85); 2.4982 (108.25); 2.4937 (51.49); 2.3387 (0.33); 2.3341 (0.69); 2.3296 (0.99); 2.325 (0.69); 2.3205 (0.36); 1.6289 (2.74); 1.6147 (6.31); 1.608 (6.89); 1.5949 (2.91); 1.319 (0.39); 1.2999 (6.82); 1.2823 (16); 1.265 (12.46); 1.2593 (8); 1.2446 (2.65); 0.146 (0.66); 0.0079 (5.65); −0.0002 (162.34); −0.0085 (6.03); −0.1496 (0.64)

Compound No. 78 [DMSO]

9.8974 (3.95); 9.8732 (4.1); 9.8091 (3.66); 9.0988 (8.44); 8.8524 (12.7); 8.8402 (3.73); 8.1248 (10.61); 8.109 (10.56); 7.4885 (13.9); 6.3806 (0.4); 6.3597 (1.5); 6.3379 (2.23); 6.3157 (1.61); 6.2938 (0.47); 4.6488 (1.71); 4.6318 (5.13); 4.6141 (5.15); 4.5965 (1.7); 3.325 (44.46); 2.6779 (0.41); 2.6734 (0.56); 2.6689 (0.41); 2.5264 (1.48); 2.5129 (33.2); 2.5087 (66.16); 2.5043 (86.4); 2.4998 (62.51); 2.4956 (30.23); 2.3354 (0.4); 2.3311 (0.53); 2.3266 (0.38); 1.9903 (0.36); 1.8679 (2.95); 1.8574 (6.76); 1.8487 (7.3); 1.8389 (2.9); 1.2978 (7.49); 1.2804 (16); 1.2626 (7.4); 1.2252 (3.12); 1.2149 (7.08); 1.2062 (7.06); 1.1955 (2.7); 1.1771 (0.37); 0.1459 (0.41); 0.0077 (3.37); −0.0002 (87.7); −0.0084 (3.1); −0.1498 (0.42)

Compound No. 79 [DMSO]

10.0148 (0.33); 9.9923 (0.35); 9.9461 (4.26); 9.922 (4.4); 8.6421 (4.83); 8.6319 (4.78); 8.6084 (0.43); 8.4569 (12.78); 8.3972 (0.34); 8.3159 (0.51); 8.1206 (11.81); 8.1047 (11.96); 8.0857 (0.72); 7.6081 (0.8); 7.6008 (0.83); 7.587 (16); 7.3206 (1.04); 7.3083 (2.76); 6.3788 (0.54); 6.357 (1.74); 6.3356 (2.62); 6.3131 (1.88); 6.2922 (0.62); 5.4444 (0.37); 5.4184 (11.24); 5.4131 (10.99); 5.17 (0.34); 5.1557 (0.68); 5.1414 (0.4); 4.4972 (1.09); 4.4829 (1.05); 4.3787 (0.4); 4.3613 (0.4); 4.3504 (0.41); 4.3446 (0.49); 4.334 (0.51); 3.3212 (69.74); 3.2075 (0.44); 3.202 (0.53); 3.1762 (4.11); 3.1704 (8.54); 3.1645 (3.77); 2.859 (0.55); 2.849 (1.4); 2.8398 (2.1); 2.8311 (3.05); 2.8214 (3.05); 2.813 (2.02); 2.8034 (1.44); 2.7935 (0.49); 2.6753 (1.22); 2.6712 (1.64); 2.6667 (1.23);

2.5849 (0.33); 2.5501 (0.95); 2.5414 (1.64); 2.511 (101.78); 2.5067 (194); 2.5022 (247.87); 2.4977 (180.17); 2.4935 (88.99); 2.4406 (0.37); 2.3333 (1.16); 2.3291 (1.58); 2.3242 (1.19); 1.3558 (0.56); 1.3377 (1.05); 1.3234 (0.89); 1.306 (1.35); 1.2882 (0.79); 1.2608 (0.34); 1.2338 (1.31); 1.1275 (0.36); 1.0452 (2.38); 1.03 (2.38); 0.8864 (0.34); 0.7513 (1.9); 0.7384 (5.68); 0.7336 (7.63); 0.7213 (7.17); 0.7157 (6.16); 0.7041 (2.32); 0.5807 (0.33); 0.5408 (2.48); 0.5298 (7.2); 0.5242 (7.23); 0.5202 (6.85); 0.5148 (6.54); 0.5025 (1.94); 0.1459 (1.03); 0.0078 (12.74); −0.0002 (246.69); −0.0084 (11.52); −0.1497 (1.1)

Compound No. 80 [DMSO]

9.9904 (2.84); 9.9668 (2.97); 9.4877 (6.88); 8.4489 (16); 8.3154 (0.72); 8.2534 (1.7); 8.2349 (3.06); 8.2163 (1.64); 7.5584 (12.51); 6.3979 (0.35); 6.3776 (1.18); 6.3565 (1.68); 6.3345 (1.27); 6.3131 (0.4); 5.7556 (0.71); 5.3547 (7.12); 5.349 (7.12); 4.0979 (0.88); 4.0847 (0.92); 3.8538 (0.39); 3.321 (144.69); 3.1899 (3.07); 3.1839 (7.15); 3.1778 (3.2); 3.1752 (4.69); 3.162 (3.93); 2.787 (0.37); 2.6796 (0.56); 2.6754 (1.21); 2.6708 (1.66); 2.6663 (1.17); 2.6617 (0.56); 2.5643 (0.4); 2.5411 (1.12); 2.5241 (4.35); 2.5108 (96.06); 2.5063 (196.65); 2.5017 (259.13); 2.4972 (184.73); 2.4926 (87.94); 2.3331 (1.21); 2.3285 (1.65); 2.324 (1.2); 1.633 (2.37); 1.6188 (5.45); 1.6119 (5.92); 1.5989 (2.63); 1.3597 (0.37); 1.3526 (0.36); 1.3475 (0.38); 1.342 (0.34); 1.3073 (2.76); 1.2937 (5.56); 1.2871 (5.98); 1.2727 (2.33); 1.2588 (0.51); 1.2331 (1.69); 0.8531 (0.33); 0.1459 (1.21); 0.0207 (0.56); 0.0156 (0.71); 0.0079 (9.47); −0.0002 (289.05); −0.0086 (11.11); −0.0179 (0.69); −0.0245 (0.47); −0.1498 (1.2)

Compound No. 81 [DMSO]

9.8686 (0.77); 9.8449 (0.81); 9.3199 (1.67); 8.2198 (2.84); 8.2049 (1.23); 8.0752 (0.63); 8.0557 (0.74); 7.8351 (0.58); 7.8153 (0.86); 7.7439 (0.62); 7.7243 (0.97); 7.7048 (0.42); 7.4765 (2.86); 6.3553 (0.32); 6.3333 (0.5); 6.3108 (0.36); 5.3989 (2.01); 5.3933 (2.01); 4.038 (0.41); 4.0202 (0.42); 3.9277 (1.59); 3.8811 (0.32); 3.8518 (0.67); 3.3217 (5.67); 3.0814 (0.78); 3.0754 (1.66); 3.0696 (0.73); 2.9625 (12.03); 2.7835 (0.67); 2.671 (0.41); 2.6664 (0.33); 2.6388 (6.81); 2.5108 (23.78); 2.5064 (46.82); 2.5019 (60.88); 2.4973 (43.79); 2.4929 (21.14); 2.3334 (0.34); 2.3286 (0.44); 2.3242 (0.32); 1.9887 (1.89); 1.6066 (0.6); 1.5924 (1.47); 1.5855 (1.58); 1.5726 (0.68); 1.327 (0.77); 1.3137 (1.58); 1.307 (1.64); 1.2925 (0.65); 1.2346 (0.7); 1.1929 (0.56); 1.1751 (1.07); 1.1575 (0.71); 1.0689 (16); 0.0079 (3.02); −0.0002 (65.77); −0.0085 (2.39)

Compound No. 82 [DMSO]

10.0382 (2.8); 10.0147 (2.95); 9.81 (2.85); 9.6566 (0.65); 9.6464 (0.59); 9.0954 (6.51); 8.8565 (9.23); 8.8331 (2.85); 8.2634 (1.74); 8.2451 (3.16); 8.2267 (1.72); 7.9536 (1.25); 7.5039 (10.74); 6.8706 (1.36); 6.6405 (0.77); 6.4048 (1.18); 6.3833 (1.79); 6.3619 (1.3); 6.3404 (0.39); 4.6458 (1.35); 4.6286 (4.07); 4.6108 (4.1); 4.5932 (1.34); 4.1124 (0.7); 4.0992 (2.13); 4.0861 (2.18); 4.073 (0.76); 3.3237 (39.23); 3.1764 (9.84); 3.1633 (9.54); 2.8922 (9.13); 2.7331 (7.68); 2.6767 (0.56); 2.6721 (0.74); 2.6679 (0.55); 2.5424 (0.49); 2.5253 (2.07); 2.5119 (42.62); 2.5077 (84.2); 2.5032 (109.28); 2.4987 (78.96); 2.4944 (38.53); 2.3345 (0.68); 2.3299 (0.84); 2.3254 (0.66); 2.1839 (2.27); 1.8662 (2.31); 1.8561 (5.23); 1.847 (5.71); 1.8377 (2.34); 1.5813 (2.77); 1.5735 (6.72); 1.5635 (7.18); 1.5559 (3); 1.3561 (16); 1.2979 (5.74); 1.2805 (12.34); 1.2627 (5.78); 1.2232 (2.63); 1.2134 (5.48); 1.2043 (5.57); 1.1941 (2.28); 0.9919 (3.03); 0.9841 (7.25); 0.9741 (6.83); 0.9662 (2.8); 0.1461 (0.34); 0.0079 (3.04); −0.0002 (77.4); −0.0085 (3.09); −0.1496 (0.33)

Compound No. 83 [DMSO]

9.947 (3.92); 9.923 (3.98); 9.4503 (8.85); 8.3886 (16); 8.3391 (5.89); 8.316 (0.43); 8.1077 (2.85); 8.0871 (3.34); 7.8933 (5.64); 7.8723 (4.62); 7.4407 (13.17); 6.4297 (0.47); 6.409 (1.63); 6.3873 (2.38); 6.365 (1.67); 6.3426 (0.47); 4.577 (1.99); 4.5596 (5.56); 4.542 (5.46); 4.5244 (1.79); 3.3242 (115.57); 3.1763 (1.05); 3.1632 (1.01); 2.6765 (0.8); 2.6721 (1); 2.6676 (0.71); 2.5117 (75.83); 2.5076 (128.69); 2.5031 (155.34); 2.4987 (109.96); 2.3343 (0.82); 2.3298 (1.02); 2.3255 (0.74); 2.1844 (0.44); 1.6263 (3.24); 1.6121 (7.86); 1.6054 (7.97); 1.5923 (3.24); 1.3561 (3.15); 1.3444 (0.41); 1.3036 (3.92); 1.2902 (8.07); 1.2836 (8.19); 1.2647 (8.38); 1.2471 (15.93); 1.2294 (7.44); 1.1047 (0.34); 0.8712 (0.34); 0.8637 (0.32); 0.0077 (2.97); −0.0002 (34.8); −0.0084 (1.54)

Compound No. 84 [DMSO]

9.9026 (3.47); 9.8787 (3.57); 9.7795 (2.98); 8.9999 (7.75); 8.8983 (2.96); 8.6082 (16); 8.3364 (4.82); 8.3331 (4.88); 8.3155 (0.59); 8.1085 (2.28); 8.1056 (2.27); 8.0878 (2.7); 8.0841 (2.68); 7.8962 (5.02); 7.8752 (4.17); 7.4369 (12.39); 6.87 (1.19); 6.6408 (0.7); 6.4353 (0.35); 6.4137 (1.32); 6.3918 (1.98); 6.3698 (1.41); 6.3472 (0.41); 4.5726 (1.53); 4.5555 (4.55); 4.5379 (4.55); 4.5202 (1.46); 4.0991 (0.58); 4.086 (0.58); 3.3231 (218.87); 3.1757 (2.17); 3.1625 (2.08); 2.6759 (1.03); 2.6714 (1.4); 2.6668 (1.03); 2.5417 (1.06); 2.5111 (82.23); 2.5068 (161.97); 2.5023 (212.35); 2.4978 (153.16); 2.4934 (73.83); 2.3336 (0.97); 2.3291 (1.34); 2.3246 (0.97); 2.2896 (0.37); 2.1834 (1.9); 1.8726 (2.69); 1.8622 (5.94); 1.8533 (6.39); 1.8438 (2.57); 1.3555 (13.88); 1.2761 (3); 1.2659 (7.15); 1.2581 (11.96); 1.2414 (14.75); 1.2236 (6.5); 0.0079 (2.07); −0.0002 (48.52); −0.0084 (1.76)

Compound No. 85 [DMSO]

10.0897 (3.28); 10.0662 (3.43); 9.5311 (8.43); 8.4974 (11.02); 8.316 (0.36); 8.2672 (2.01); 8.2487 (3.67); 8.2302 (1.95); 7.5113 (13.18); 6.42 (0.36); 6.4002 (1.37); 6.379 (2.02); 6.3572 (1.47); 6.3364 (0.44); 5.7563 (0.41); 4.6476 (1.62); 4.6302 (4.79); 4.6123 (4.75); 4.5948 (1.55); 3.324 (142.52); 2.6765 (0.67); 2.672 (0.89); 2.6674 (0.65); 2.5422 (0.53); 2.5252 (2.4); 2.5119 (52.96); 2.5074 (107.77); 2.5029 (141.6); 2.4983 (99.77); 2.4939 (46.34); 2.3388 (0.33); 2.3342 (0.65); 2.3297 (0.9); 2.3251 (0.64); 2.1837 (0.46); 1.63 (2.85); 1.6159 (6.79); 1.609 (7.3); 1.5959 (3.05); 1.3558 (3.58); 1.3173 (0.51); 1.3014 (7.19); 1.2839 (16); 1.2782 (5.41); 1.2657 (12.32); 1.2575 (7.71); 1.243 (2.76); 0.0079 (0.7); −0.0002 (22.06); −0.0086 (0.7)

Compound No. 86 [DMSO]

9.9117 (3.76); 9.8875 (3.88); 8.6154 (4.17); 8.6051 (4.21); 8.402 (11.36); 8.3893 (0.44); 8.128 (10.22); 8.1122 (10.19); 7.4955 (0.61); 7.4818 (13.91); 6.3692 (0.39); 6.3486 (1.44); 6.3272 (2.13); 6.3044 (1.53); 6.2831 (0.45); 4.6453 (1.74); 4.628 (5.03); 4.61 (5.01); 4.5924 (1.71); 4.0394 (0.77); 4.0216 (0.76); 3.5695 (1.91); 3.3249 (51.07); 3.0512 (0.8); 2.8563 (0.4); 2.8465 (1.18); 2.8373 (1.74); 2.8284 (2.6); 2.8188 (2.62); 2.81 (1.72); 2.8007 (1.23); 2.7905 (0.55); 2.7856 (0.74); 2.6775 (0.42); 2.6729 (0.59); 2.6684 (0.43); 2.5262 (1.39); 2.5128 (34.86); 2.5084 (70.67); 2.5039 (92.51); 2.4994 (66.08); 2.495 (31.38); 2.3352 (0.45); 2.3307 (0.63); 2.3262 (0.46); 1.9902 (3.42); 1.3105 (0.56); 1.2923 (7.38); 1.2748 (16); 1.257 (7.13); 1.1942 (0.95); 1.1764 (1.84); 1.1586 (0.91); 0.7467 (1.65); 0.7337 (4.82); 0.7289 (6.5); 0.7166 (6.16); 0.7109 (5.15); 0.6993 (1.99); 0.5401 (2.05); 0.5293 (6.13); 0.5233 (5.88); 0.5194 (5.5); 0.5139 (5.44); 0.5017 (1.65); 0.008 (0.65); −0.0002 (19.99); −0.0085 (0.68)

Compound No. 87 [DMSO]

10.0601 (3.7); 10.0365 (3.83); 8.6181 (4.13); 8.6078 (4.13); 8.4158 (11.61); 8.2748 (2.18); 8.2564 (3.93); 8.2379 (2.12); 7.5181 (0.47); 7.5004 (14.65); 6.4185 (0.4); 6.3984

(1.51); 6.3773 (2.21); 6.3553 (1.62); 6.3345 (0.49); 4.6424 (1.78); 4.6251 (5.19); 4.6072 (5.15); 4.5898 (1.71); 3.3241 (53.84); 2.8556 (0.41); 2.8455 (1.18); 2.8362 (1.74); 2.8274 (2.62); 2.8177 (2.62); 2.8089 (1.73); 2.7997 (1.23); 2.7897 (0.44); 2.677 (0.45); 2.6725 (0.62); 2.6679 (0.45); 2.5425 (0.32); 2.5123 (37.24); 2.5079 (73.88); 2.5034 (96.74); 2.4988 (69.29); 2.4944 (33.03); 2.3345 (0.48); 2.3301 (0.64); 2.3257 (0.48); 1.3112 (0.58); 1.2934 (7.4); 1.276 (16); 1.2583 (7.13); 1.232 (0.49); 0.7463 (1.71); 0.7335 (4.86); 0.7285 (6.51); 0.7163 (6.17); 0.7107 (5.14); 0.6991 (2.02); 0.5386 (2.18); 0.5278 (6.2); 0.5218 (5.86); 0.518 (5.47); 0.5124 (5.34); 0.5002 (1.64); 0.0078 (0.71); −0.0002 (18.43); −0.0085 (0.66)

Compound No. 88 [DMSO]
9.9191 (3.88); 9.8952 (3.92); 8.5565 (4.51); 8.5459 (4.3); 8.3752 (0.44); 8.342 (6.49); 8.3166 (0.37); 8.2932 (13.56); 8.1094 (3.09); 8.0886 (3.68); 7.8914 (5.56); 7.8704 (4.57); 7.4238 (11.65); 6.872 (1.33); 6.6422 (0.75); 6.425 (0.47); 6.4047 (1.68); 6.383 (2.51); 6.3606 (1.74); 6.3384 (0.49); 5.7568 (0.36); 4.5737 (2); 4.5564 (5.71); 4.5388 (5.67); 4.5212 (1.89); 3.3248 (66.67); 2.8766 (0.45); 2.8666 (1.24); 2.8572 (1.82); 2.8488 (2.59); 2.8387 (2.57); 2.8304 (1.79); 2.8206 (1.3); 2.8106 (0.43); 2.673 (0.74); 2.5078 (96.4); 2.5038 (107.95); 2.3307 (0.71); 2.1848 (2.1); 1.3568 (14.55); 1.3321 (0.35); 1.2988 (0.41); 1.2901 (0.46); 1.2584 (7.7); 1.2409 (16); 1.2234 (7.22); 1.183 (0.78); 0.8543 (0.39); 0.7446 (1.64); 0.7312 (5.74); 0.7269 (6.31); 0.7144 (6.54); 0.7093 (5.09); 0.6975 (1.89); 0.5644 (2.31); 0.5538 (7.08); 0.5477 (6.9); 0.5389 (5.55); 0.5263 (1.53); −0.0001 (15.88)

Compound No. 89 [DMSO]
9.7897 (1.99); 9.7656 (2.05); 9.673 (1.78); 8.9808 (1.77); 8.8298 (4.22); 8.3687 (6.55); 8.3377 (2.96); 8.1078 (1.38); 8.0885 (1.65); 7.8932 (2.84); 7.8722 (2.37); 7.3473 (6.28); 6.4041 (0.78); 6.3823 (1.18); 6.3599 (0.85); 4.6221 (0.89); 4.605 (2.56); 4.5872 (2.56); 4.5701 (0.89); 3.3561 (4.54); 3.1707 (1.88); 2.6725 (0.34); 2.6149 (16); 2.5081 (39.51); 2.5038 (50.11); 2.4996 (36.59); 1.9901 (0.46); 1.8699 (1.51); 1.8597 (3.45); 1.8508 (3.68); 1.8414 (1.52); 1.2633 (1.7); 1.2534 (3.87); 1.2431 (6.34); 1.2343 (2.61); 1.2246 (7.84); 1.2069 (3.61); 1.1762 (0.34); −0.0002 (25.42); −0.0083 (1.15)

Compound No. 90 [DMSO]
9.8414 (1.78); 9.8173 (1.84); 9.2864 (3.78); 8.343 (2.42); 8.3393 (2.44); 8.1792 (6.58); 8.1112 (1.15); 8.1076 (1.12); 8.0903 (1.39); 8.0868 (1.34); 7.8915 (2.65); 7.8705 (2.22); 7.358 (6.58); 6.8726 (0.51); 6.4014 (0.68); 6.3795 (1.02); 6.3571 (0.73); 4.6209 (0.78); 4.6037 (2.25); 4.5857 (2.22); 4.5682 (0.75); 3.603 (0.35); 3.3277 (14.06); 2.631 (16); 2.5276 (0.48); 2.5142 (12.06); 2.5097 (24.39); 2.5052 (31.85); 2.5006 (22.39); 2.4961 (10.38); 2.1853 (0.84); 1.7609 (0.46); 1.6053 (1.34); 1.5912 (3.26); 1.5843 (3.43); 1.5714 (1.48); 1.3578 (6.47); 1.3235 (1.74); 1.3101 (3.47); 1.3034 (3.63); 1.2889 (1.36); 1.2483 (3.47); 1.2309 (7.68); 1.2132 (3.37); 0.0079 (0.53); −0.0002 (14.35); −0.0085 (0.45)

Compound No. 91 [DMSO]
9.803 (1.61); 9.7791 (1.7); 8.4144 (1.79); 8.4039 (2.03); 8.341 (2.61); 8.1089 (1.26); 8.085 (2.03); 8.078 (5.86); 8.0684 (1.1); 7.8876 (2.5); 7.8765 (0.69); 7.8667 (2.2); 7.8564 (0.43); 7.3421 (5.13); 7.3323 (0.96); 6.8715 (1.53); 6.6419 (0.81); 6.394 (0.74); 6.3722 (1.12); 6.3499 (0.84); 4.6162 (0.88); 4.5988 (2.44); 4.581 (2.55); 4.5644 (1.06); 3.326 (13.06); 3.3164 (3.3); 3.1778 (1.06); 3.1771 (1.06); 3.1649 (1.15); 2.8769 (0.55); 2.8673 (0.85); 2.8587 (1.27); 2.8489 (1.37); 2.8399 (1.06); 2.8316 (1.24); 2.821 (0.43); 2.6078 (13.48); 2.5982 (2.76); 2.5077 (28.44); 2.5037 (35.83); 2.4995 (28.62); 2.1843 (2.41); 2.1747 (0.49); 1.3568 (16); 1.3471 (2.99); 1.2589 (0.44); 1.2391 (3.62); 1.2219 (7.03); 1.2043 (3.55); 1.1835 (0.57); 0.7343 (0.75); 0.7216 (2.25); 0.7165 (2.86); 0.7044 (3.06); 0.6986 (2.5); 0.6877 (1.31); 0.5703 (1.01); 0.5599 (3.04); 0.5504 (2.99); 0.5444 (2.86); 0.5325 (1.15); 0.0066 (0.58); −0.0002 (6.66); −0.0015 (6.77); −0.0101 (1.08)

Compound No. 92 [DMSO]
9.694 (1.78); 9.6697 (1.83); 8.4783 (0.79); 8.4652 (1.58); 8.4519 (0.77); 8.2073 (2.61); 8.0749 (1.41); 8.0557 (1.55); 7.9278 (5.34); 7.8323 (1.3); 7.8125 (1.84); 7.7385 (1.42); 7.7189 (2.15); 7.6995 (0.89); 7.311 (6.57); 6.3306 (0.71); 6.3087 (1.08); 6.2859 (0.78); 4.6142 (0.82); 4.5969 (2.37); 4.5789 (2.37); 4.5614 (0.82); 4.3731 (3.74); 4.3597 (3.75); 3.9198 (1.18); 3.9112 (0.4); 3.3372 (8.17); 2.6771 (0.38); 2.6723 (0.39); 2.5776 (16); 2.5423 (0.33); 2.5254 (1.3); 2.5121 (22.95); 2.5077 (45.25); 2.5032 (58.67); 2.4987 (41.94); 2.4943 (20.06); 2.3869 (0.32); 2.3649 (0.34); 2.3345 (0.32); 2.33 (0.42); 2.3255 (0.32); 1.6556 (0.42); 1.6434 (0.86); 1.6363 (0.95); 1.6244 (1.67); 1.6125 (0.98); 1.6049 (1.1); 1.593 (0.5); 1.5092 (0.43); 1.5022 (0.5); 1.4987 (0.41); 1.4903 (0.72); 1.4838 (0.37); 1.4785 (0.43); 1.4707 (0.5); 1.4588 (0.34); 1.3565 (1.01); 1.3371 (0.53); 1.3124 (0.46); 1.299 (1.98); 1.2795 (0.58); 1.2589 (3.03); 1.235 (9.25); 1.2179 (8.1); 1.2002 (3.61); 0.9479 (0.48); 0.9295 (0.83); 0.9113 (0.47); 0.8976 (0.43); 0.8808 (0.47); 0.8708 (0.55); 0.8537 (1.28); 0.8356 (0.76); 0.8191 (0.87); 0.8119 (1.7); 0.8062 (0.83); 0.7992 (0.69); 0.7919 (1.54); 0.7868 (1.38); 0.7808 (1.4); 0.7737 (1.25); 0.7694 (1.6); 0.7619 (0.69); 0.7212 (0.5); 0.7089 (1.87); 0.7018 (3.64); 0.6972 (3.12); 0.6903 (2.93); 0.6852 (1.96); 0.6799 (1.91); 0.6747 (3.45); 0.6676 (1.57); 0.6604 (1.97); 0.6549 (2.91); 0.6477 (1.42); 0.6358 (0.51); 0.0079 (2.82); −0.0002 (69.56); −0.0085 (2.62)

Compound No. 93 [DMSO]
9.6921 (1.74); 9.6678 (1.78); 8.2055 (2.59); 8.1845 (1.43); 8.1712 (0.72); 8.0726 (1.29); 8.053 (1.43); 7.9107 (5.14); 7.8312 (1.22); 7.8118 (1.68); 7.7368 (1.29); 7.7172 (2.01); 7.6977 (0.83); 7.3035 (6.82); 6.3282 (0.68); 6.3059 (1.01); 6.2834 (0.73); 4.6094 (0.77); 4.5925 (2.26); 4.5745 (2.23); 4.5572 (0.74); 4.3465 (3.75); 4.3327 (3.64); 3.6106 (0.33); 3.3246 (56.33); 2.676 (0.38); 2.6715 (0.51); 2.6668 (0.37); 2.5647 (16); 2.5417 (0.46); 2.5247 (1.62); 2.5115 (31.18); 2.507 (61.72); 2.5025 (80.29); 2.4979 (56.67); 2.4933 (26.39); 2.3338 (0.43); 2.3291 (0.54); 2.3246 (0.4); 2.1835 (1.51); 2.1644 (4.91); 2.1454 (5.04); 2.1264 (1.65); 1.2325 (3.62); 1.2151 (7.72); 1.1974 (3.36); 1.1842 (0.52); 1.052 (6.16); 1.0454 (1.76); 1.033 (12.83); 1.0225 (0.77); 1.014 (5.93); 0.9921 (0.47); 0.146 (0.39); 0.0079 (3.83); −0.0002 (93.32); −0.0086 (3.12); −0.1498 (0.42)

Compound No. 94 [DMSO]
See Synthesis Example 3

Compound No. 95 [DMSO]
20.0114 (0.79); 8.4005 (1.01); 8.3142 (1.93); 8.1244 (0.5); 7.9516 (2.16); 7.4164 (0.99); 4.5139 (0.53); 3.8379 (1.19); 3.3229 (1081.78); 3.1749 (1.25); 3.1617 (1.16); 2.8908 (16); 2.7312 (12.97); 2.6895 (0.91); 2.6706 (5.04); 2.506 (570.38); 2.5015 (743.97); 2.4971 (554.79); 2.4928 (278.03); 2.3283 (5.62); 1.9079 (4.78); 1.7415 (1.52); 1.3626 (1.79); 1.3447 (2.73); 1.3268 (1.74); 1.2979 (4.72); 1.2587 (6.63); 1.2356 (7.05); 1.148 (1.55); 0.8536 (1.91); 0.7286 (1.12); 0.5659 (1.2); 0.1461 (0.85); −0.0001 (138.02); −0.0084 (3.8); −0.1497 (0.59)

Compound No. 97 [DMSO]
9.4227 (4.95); 8.2465 (8.77); 7.9518 (0.39); 7.909 (1.75); 7.8905 (3.74); 7.8726 (2.34); 7.8128 (2.2); 7.7926 (3.42); 7.7835 (2.67); 7.0109 (0.78); 6.7983 (0.34); 3.9626 (0.33); 3.8007 (16); 3.7603 (0.47); 3.4233 (0.51); 3.3404 (686.45);

3.0144 (11.75); 2.891 (2.63); 2.7316 (2.2); 2.6895 (0.48); 2.6762 (0.94); 2.6718 (1.18); 2.6674 (0.89); 2.5071 (132.01); 2.5028 (164.06); 2.4984 (122.49); 2.3337 (0.83); 2.3295 (1.07); 2.3251 (0.8); 1.6092 (1.95); 1.5951 (4.81); 1.5883 (5.06); 1.5754 (2.13); 1.3449 (0.37); 1.305 (2.31); 1.2916 (4.83); 1.285 (4.88); 1.2705 (1.84); 1.2345 (2.96); 0.8537 (0.45); −0.0001 (1.92)

Compound No. 98 [DMSO]

10.3045 (1.87); 10.2807 (1.93); 9.6625 (1.61); 9.1047 (1.58); 8.9483 (3.83); 8.3261 (9.26); 8.0985 (1.2); 8.095 (1.19); 8.0776 (1.42); 8.074 (1.4); 7.9061 (2.69); 7.8851 (2.23); 6.8715 (0.33); 6.4124 (0.71); 6.3909 (1.04); 6.3689 (0.76); 4.3885 (0.43); 4.3705 (0.81); 4.3533 (1.29); 4.3355 (1.22); 4.3262 (1.21); 4.3082 (1.3); 4.2909 (0.79); 4.2734 (0.43); 4.0567 (0.67); 4.039 (2.03); 4.0211 (2.06); 4.0033 (0.69); 3.3246 (23.88); 2.6169 (16); 2.5121 (16.07); 2.5076 (31.58); 2.5031 (41.32); 2.4985 (29.66); 2.494 (14.3); 2.1841 (0.53); 1.9896 (9.09); 1.8701 (1.46); 1.8597 (3.12); 1.8507 (3.32); 1.8412 (1.38); 1.3566 (4.19); 1.2617 (1.62); 1.2517 (3.42); 1.2427 (3.55); 1.2326 (1.9); 1.1938 (5.42); 1.176 (10.25); 1.1582 (5.1); 0.0079 (1.05); −0.0002 (24.67); −0.0085 (0.96)

a) The determination of the W by LC-MS in the acidic range is effected at pH 2.7, acetonitrile (contains 0.1% formic acid) and water as eluents; linear gradient from 10% acetonitrile to 95% acetonitrile, instrument: Agilent 1100 LC-System, Agilent MSD System, HTS PAL.

The log P values reported in the tables and Preparation Examples above were determined in accordance with EEC directive 79/831 Annex V.A8 by HPLC (High Performance Liquid Chromatography) using a reversed-phase column (C18). Temperature 43° C. The calibration is effected with unbranched alkan-2-ones (having 3 to 16 carbon atoms), for which the log P values are known.

b) The $^1$H NMR data are determined with a Bruker Avance 400 equipped with a flow probe head (volume 60 nl), with tetramethylsilane as a reference (0.0) and the solvents $CD_3CN$, $CDCl_3$, $D_6$-DMSO.

The NMR data for selected examples are listed either in conventional form (δ values, multiplet splitting, number of hydrogen atoms) or as NMR peak lists.

NMR peak list method:

When the $^1$H NMR data for selected examples are noted in the form of $^1$H NMR peak lists, first the δ-value in ppm and then the signal intensity in Y brackets were listed for each signal peak. The δ value signal intensity number pairs for different signal peaks are listed with separation from one another by semicolons.

The peak list for one example therefore takes the form of:
$\delta_1$ (intensity$_1$); $\delta_2$ (intensity$_2$); . . . ; $\delta_i$(intensity$_i$); . . . ; $\delta_a$(intensity$_a$)

The solvent in which the NMR spectrum was recorded is listed in square brackets after the number of the example and before the NMR peak list or the conventional NMR interpretation list.

Use Examples

The examples which follow demonstrate the insecticidal and acaricidal action of the compounds according to the invention. In these examples, the compounds according to the invention cited relate to the compounds listed in Table 1 with the corresponding reference numerals (No.):

Example A

*Boophilus microplus* Test (BOOPMI Injection)

| Solvent: | dimethyl sulphoxide |
|---|---|

To produce a suitable active compound formulation, 10 mg of active compound are mixed with 0.5 ml of solvent and the concentrate is diluted with solvent to the desired concentration.

The active compound solution is injected into the abdomen (*Boophilus microplus*), and the animals are transferred into dishes and stored in a climate-controlled room.

After 7 days, the efficacy in % is determined. The activity is assessed by laying of fertile eggs. 100% means that none of the ticks has laid any fertile eggs.

In this test, for example, the following compounds from the preparation examples show an efficacy of 100% at an application rate of 20 µg/animal: 1, 6, 10, 11, 12, 16, 22, 23, 26, 27, 28, 29, 30, 32, 41, 42, 53, 58, 60, 63, 64, 65.

Example B

*Ctenocephalides felis*; Oral (CTECFE)

| Solvent: | 1 part by weight of dimethyl sulphoxide |
|---|---|

To produce a suitable active compound formulation, 10 mg of active compound are mixed with 0.5 ml of dimethyl sulphoxide. A portion of the concentrate is diluted with citrated cattle blood, and the desired concentration is prepared.

About 20 unfed adult fleas (*Ctenocephalides felis*) are placed into a chamber which is closed at the top and bottom with gauze. A metal cylinder whose bottom end is closed with parafilm is placed onto the chamber. The cylinder contains the blood/active compound preparation, which can be imbibed by the fleas through the parafilm membrane.

After 2 days, the kill in % is determined 100% means that all fleas have been killed; 0% means that none of the fleas have been killed.

In this test, for example, the following compounds from the preparation examples show an efficacy of 100% at an application rate of 100 ppm: 1, 6, 10, 11, 12, 16, 26, 27, 30, 32, 41, 42, 53, 58, 63, 64, 65.

In this test, for example, the following compounds from the preparation examples show an efficacy of 95% at an application rate of 100 ppm: 22, 28, 29, 60.

Example C

*Lucilia cuprina* Test (LUCICU)

| Solvent: | dimethyl sulphoxide |
|---|---|

To produce a suitable active compound formulation, 10 mg of active compound are mixed with 0.5 ml of dimethyl sulfoxide, and the concentrate is diluted with water to the desired concentration.

Vessels containing horse meat treated with the active compound formulation of the desired concentration are populated with about 20 *Lucilia cuprina* larvae.

After 2 days, the kill in % is determined 100% means that all the larvae have been killed; 0% means that none of the larvae have been killed.

In this test, for example, the following compounds from the preparation examples show an efficacy of 100% at an application rate of 100 ppm: 1, 6, 10, 11, 12, 16, 22, 23, 26, 27, 28, 29, 30, 32, 41, 42, 53, 58, 60, 63, 64, 65.

Example D

*Musca domestica* Test (MUSCDO)

| Solvent: | dimethyl sulphoxide |
|---|---|

To produce a suitable active compound formulation, 10 mg of active compound are mixed with 0.5 ml of dimethyl sulfoxide, and the concentrate is diluted with water to the desired concentration.

Vessels containing a sponge treated with the active compound formulation of the desired concentration are populated with adult *Musca domestica*.

After 2 days, the kill in % is determined 100% means that all flies have been killed; 0% means that no flies have been killed.

In this test, for example, the following compounds from the preparation examples show an efficacy of 100% at an application rate of 100 ppm: 1, 6, 10, 11, 12, 16, 22, 26, 27, 28, 29, 32, 41, 42, 53, 63, 64.

In this test, for example, the following compounds from the preparation examples show an efficacy of 80% at an application rate of 100 ppm: 65

Example E

*Myzus persicae*-Spray Test (MYZUPE)

| Solvent: | 78 parts by weight of acetone |
|---|---|
| | 1.5 parts by weight of dimethylformamide |
| Emulsifier: | 0.5 part by weight of alkylaryl polyglycol ether |

To produce a suitable active compound formulation, 1 part by weight of active compound is mixed with the stated amounts of solvent and emulsifier, and the concentrate is diluted with emulsifier-containing water to the desired concentration.

Discs of Chinese cabbage leaves (*Brassica pekinensis*) infested by all stages of the green peach aphid (*Myzus persicae*) are sprayed with an active compound formulation of the desired concentration.

After 6 days, the efficacy in % is determined 100% means that all the aphids have been killed; 0% means that none of the aphids have been killed.

In this test, for example, the following compounds from the preparation examples show an efficacy of 100% at an application rate of 100 g/ha: 6, 11, 26.

In this test, for example, the following compounds from the preparation examples show an efficacy of 90% at an application rate of 100 g/ha: 10, 15, 75.

Example F

*Phaedon cochleariae*—Spray Test (PHAECO)

| Solvent: | 78.0 parts by weight of acetone |
|---|---|
| | 1.5 parts by weight of dimethylformamide |
| Emulsifier: | 0.5 part by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Discs of Chinese cabbage leaves (*Brassica pekinensis*) are sprayed with an active compound formulation of the desired concentration and, after drying, populated with larvae of the mustard beetle (*Phaedon cochleariae*).

After 7 days, the efficacy in % is determined. 100% means that all the beetle larvae have been killed; 0% means that no beetle larvae have been killed.

In this test, for example, the following compounds from the preparation examples show an efficacy of 100% at an application rate of 500 g/ha: 24, 40, 74.

In this test, for example, the following compounds from the preparation examples show an efficacy of 100% at an application rate of 100 g/ha: 1, 3, 4, 5, 6, 8, 10, 11, 12, 13, 14, 15, 16, 18, 20, 22, 23, 24, 25, 26, 27, 28, 29, 30, 31, 32, 33, 34, 37, 38, 39, 41, 42, 45, 46, 47, 50, 51, 52, 53, 57, 58, 59, 60, 63, 64, 65, 66, 67, 68, 69, 70, 71, 72, 73, 74, 75, 76, 93, 94, 96, 97.

In this test, for example, the following compounds from the preparation examples show an efficacy of 83% at an application rate of 100 g/ha: 40, 55, 61.

In this test, for example, the following compounds from the preparation examples show an efficacy of 100% at an application rate of 20 g/ha: 9

Example G

*Spodoptera frugiperda*—Spray Test (SPODFR)

| Solvent: | 78.0 parts by weight of acetone |
|---|---|
| | 1.5 parts by weight of dimethylformamide |
| Emulsifier: | 0.5 part by weight of alkylaryl polyglycol ether |

To produce a suitable active compound formulation, 1 part by weight of active compound is mixed with the stated amounts of solvent and emulsifier, and the concentrate is diluted with emulsifier-containing water to the desired concentration.

Leaf discs of maize (*Zea mays*) are sprayed with an active compound formulation of the desired concentration and, after drying, populated with caterpillars of the armyworm (*Spodoptera frugiperda*).

After 7 days, the efficacy in % is determined. 100% means that all the caterpillars have been killed; 0% means that no caterpillars have been killed.

In this test, for example, the following compounds from the preparation examples show an efficacy of 100% at an application rate of 500 g/ha: 74.

In this test, for example, the following compounds from the preparation examples show an efficacy of 100% at an application rate of 100 g/ha: 1, 6, 9, 10, 11, 12, 22, 23, 26, 27, 28, 29, 30, 31, 32, 38, 41, 53, 63, 64, 65, 66, 67, 68, 69, 70, 71, 72, 73, 74, 75, 76.

Example H

*Tetranychus urticae*—Spray Test, OP-Resistant (TETRUR)

| Solvent: | 78.0 parts by weight of acetone |
| | 1.5 parts by weight of dimethylformamide |
| Emulsifier : | 0.5 part by weight of alkylaryl polyglycol ether |

To produce a suitable active compound formulation, 1 part by weight of active compound is mixed with the stated amounts of solvent and emulsifier, and the concentrate is diluted with emulsifier-containing water to the desired concentration.

Discs of bean leaves (*Phaseolus vulgaris*) infested by all stages of the greenhouse red spider mite (*Tetranychus urticae*) are sprayed with an active compound formulation of the desired concentration.

After 6 days, the efficacy in % is determined 100% means that all the spider mites have been killed; 0% means that none of the spider mites have been killed.

In this test, for example, the following compounds from the preparation examples shows an efficacy of 100% at an application rate of 100 g/ha: 10, 11, 12, 17, 22, 26, 27, 32, 53, 58, 64, 66, 75, 76.

In this test, for example, the following compounds from the preparation examples shows an efficacy of 90% at an application rate of 100 g/ha: 1, 5, 6, 7, 16, 23, 25, 29, 30, 39, 42, 60, 63, 65, 67.

Example I

*Phaedon cochleariae*—Spray Test (PHAECO)

| Solvent: | 78.0 parts by weight of acetone |
| | 1.5 parts by weight of dimethylformamide |
| Emulsifier: | 0.5 part by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Discs of Chinese cabbage leaves (*Brassica pekinensis*) are sprayed with an active compound preparation of the desired concentration and, after drying, populated with larvae of the mustard beetle (*Phaedon cochleariae*).

After the stated period of time, the effect in % is determined 100% means that all the beetle larvae have been killed; 0% means that no beetle larvae have been killed.

In this test, for example, the following compounds of the Preparation Examples show superior efficacy to the prior art: see table

*Spodoptera frugiperda*—Spray Test (SPODFR)

| Solvent: | 78.0 parts by weight of acetone |
| | 1.5 parts by weight of dimethylformamide |
| Emulsifier: | 0.5 part by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Leaf discs of maize (*Zea mays*) are sprayed with an active compound preparation of the desired concentration and, after drying, populated with caterpillars of the armyworm (*Spodoptera frugiperda*).

After the stated period of time, the effect in % is determined. 100% means that all the caterpillars have been killed; 0% means that no caterpillars have been killed.

In this test, for example, the following compounds of the Preparation Examples show superior efficacy to the prior art: see table

*Tetranychus urticae*—Spray Test OP-Resistant (TETRUR)

| Solvent: | 78.0 parts by weight of acetone |
| | 1.5 parts by weight of dimethylformamide |
| Emulsifier: | 0.5 part by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Discs of bean leaves (*Phaseolus vulgaris*) infested by all stages of the greenhouse red spider mite (*Tetranychus urticae*) are sprayed with an active compound formulation of the desired concentration.

After the stated period of time, the effect in % is determined 100% means that all the spider mites have been killed; 0% means that none of the spider mites have been killed.

In this test, for example, the following compounds of the Preparation Examples show superior efficacy to the prior art: see table

| Active compound | Object | Concentration | % Efficacy dat |
|---|---|---|---|
| Known (WO2011054436) | PHAECO | 0.8 g of ai/ha | 0 7 d |
| | SPODFR | 4 g of ai/ha | 17 7 d |
| | TETRUR | 4 g of ai/ha | 0 6 d |

-continued

| Active compound | Object | Concentration | % Efficacy dat |
|---|---|---|---|
| According to the invention (Ex. 22) | PHAECO<br>SPODFR<br>TETRUR | 0.8 g of ai/ha<br>4 g of ai/ha<br>4 g of ai/ha | 100 7 d<br>100 7 d<br>90 6 d |
| Known (WO2011054436) | PHAECO | 20 g of ai/ha | 0 7 d |
| According to the invention (Ex. 14) | PHAECO | 20 g of ai/ha | 100 7 d |
| Known (WO2011054436) | PHAECO | 20 g of ai/ha | 67 7 d |
| According to the invention (Ex. 34) | PHAECO | 20 g of ai/ha | 100 7 d |

| Active compound | Object | Concentration | % Efficacy dat |
|---|---|---|---|
| 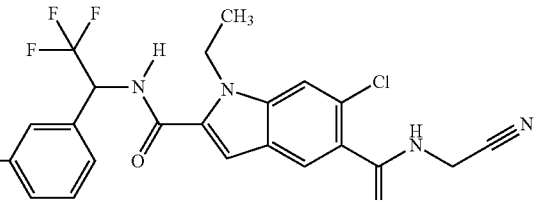 Known (WO2012119984) | TETRUR | 100 g of ai/ha | 0 6 d |
| 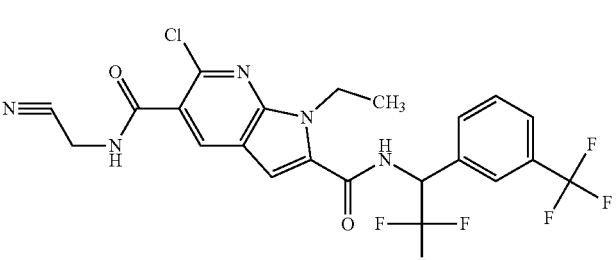 According to the invention (Ex. 42) | TETRUR | 100 g of ai/ha | 90 6 d |

The invention claimed is:

1. A compound of formula (I)

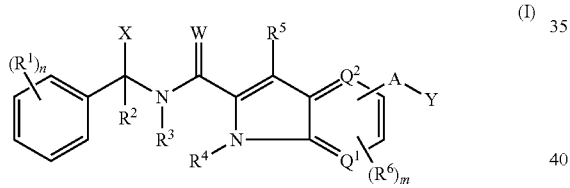

where $R^1$ represents cyano, fluorine, chlorine, bromine, iodine, methyl, ethyl, 2-methylethyl, difluoromethyl, dichlorofluoromethyl, chlorodifluoromethyl, trifluoromethyl, pentafluoroethyl, chlorotetrafluoroethyl, methoxy, difluoromethoxy, trifluoromethoxy, methylthio, trifluoromethylthio, trifluoromethylsulphinyl, or trifluoromethylsulphonyl, n represents 1, 2, 3, 4, or 5, $R^2$ represents hydrogen, $R^3$ represents hydrogen or methyl, $R^4$ represents methyl, ethyl, prop-1-yl, prop-2-en-1-yl, propyn-3-yl, ethenyl, but-2-yn-1-yl, cyclopropyl, cyclopropylmethyl, or cyclobutyl, $R^5$ represents hydrogen or bromine, $R^6$ represents cyano, fluorine, chlorine, bromine, iodine, methyl, ethyl, or trifluoromethyl, m represents 0 or 1, X represents trifluoromethyl, W represents O, A represents a bivalent chemical moiety —C(=O)NR$^{13}$— or —CH$_2$—NH—C(=O)—, where the first (left-hand) point of attachment connects to the ring and the second (right-hand) point of attachment connects to Y, and where $R^{13}$ represents hydrogen, methyl, or ethyl, Y represents methyl, ethyl, propan-1-yl, propan-2-yl, propyn-3-yl, butan-1-yl, butan-2-yl, 2-methylpropan-1-yl, 2-methylpropan-2-yl, cyclopropyl, cyclobutyl, cyanomethyl, 1-methoxycarbonylmethyl, 1-cyanoethyl, 2-cyanoethyl, 1-cyanoprop-1-yl, 2-cyanoprop-1-yl, 3-cyanoprop-1-yl, 1-cyanoprop-2-yl, 2-cyanoprop-2-yl, 1-cyanocyclopropyl, 2-cyanoprop-2-en-1-yl, 2-cyanocyclopropyl, 1-cyanocyclobutyl, 2-cyanocyclobutyl, 3-cyanocyclobutyl, 2-fluoroethyl, 2,2-difluoroethyl, 2,2,2-trifluoroethyl, 1-fluoropropan-2-yl, 2,2-difluoroprop-1-yl, 1,3-difluoropropan-2-yl, 1-methylcyclopropyl, 2-methylcyclopropyl, 1-ethylcyclopropyl, 1-ethynylcyclopropyl, 1-ethynylcyclobutyl, 1-methoxycyclopropyl, 1-ethoxycyclopropyl, 1-methoxycarbonylcyclopropyl, 1-ethoxycarbonylcyclopropyl, cyclopropylmethyl, 1-cyclopropyleth-1-yl, 1-trifluoromethylcyclopropyl, pyridin-2-yl, 5-chloropyridin-2-yl, 5-fluoropyridin-2-yl, 1-(aminothiocarbonyl)cyclopropyl, 1-cyano-2-methylpropan-1-yl, 1-cyanobut-3-yn-1-yl, 1-cyano-2-methylpropan-1-yl, 1-cyanopropan-2-yl, 1-cyano-1-cyclopropylethyl, 1-cyano-1-ethylprop-1-yl, 1-cyano-1-methylcyclopropylmethyl, (2-R)-1-(methylthio)propan-2-yl, (2-R)-1-(methylsulphinyl)propan-2-yl or 1,3-dimethoxy-2-cyanopropan-2-yl, 3-oxetan-1-yl, pyridin-2-ylmethyl, 1,3-pyrimidin-2-yl-methyl, $Q^1$ represents N, where simultaneously $Q^2$ represents a carbon atom, which is substituted by hydrogen, and/or a salt and/or N-oxide of a compound of formula (I).

2. A process for preparing a compound according to claim 1, in which A represents —C(=O)NR$^{13}$—, which comprises a) initially reacting one or more carboxylic acid derivatives of formula (IIa)

[Structure IIa shown]

where
L¹ represents hydroxyl or halogen and
L⁴ represents C₁-C₄-alkyl
with one or more amines of formula (III)

(III)
[Structure III shown]

giving one or more carboxylic esters of formula (IVa)

(IVa)
[Structure IVa shown]

and
b) then reacting one or more resulting carboxylic esters of formula (IVa)

(IVa)
[Structure IVa shown]

with one or more alkylating agents of formula (V)

R⁴-L²     (V), where L² represents a leaving group,
in the presence of a base, giving one or more compounds of formula (VIa)

(VIa)
[Structure VIa shown]

and
c) then reacting one or more compounds of formula (VIa)

(VIa)
[Structure VIa shown]

with one or more amines of formula (VII)

(VII)
$$H\underset{R^{13}}{\overset{}{N}}Y$$

giving one or more compound of formula (I) and/or a salt and/or N-oxide of a compound of formula (I).

3. A process for preparing one or more compounds according to claim 1, in which A represents —CH₂—NH—C(=O)—, which comprises
a) initially reacting one or more carboxylic acid derivatives of formula (IIc)

(IIc)
[Structure IIc shown]

where
L¹ represents halogen or represents a hydroxyl group,
Boc represents t-BuO—C(O)—
with one or more amines of formula (III)

(III)
[Structure III shown]

giving one or more compounds of formula (IVc)

(IVc)
[Structure IVc shown]

and subsequently b) reacting one or more resulting compounds of formula (IVc)

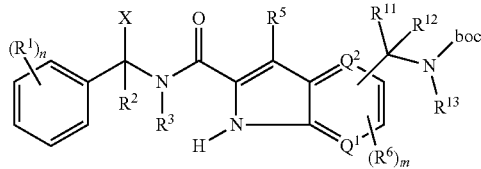
(IVc)

with one or more alkylating agents of formula (V)

R⁴-L² (V), where L² represents a leaving group, in the presence of a base, giving one or more compounds of formula (VIc)

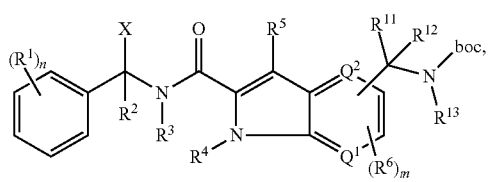
(VIc)

and subsequently c) removing the Boc protective group with an acid, giving one or more amines of formula (VIIb)

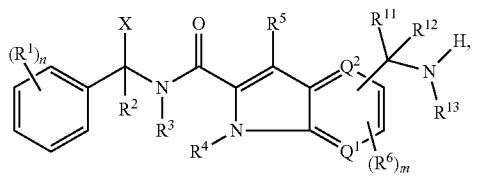
(VIIb)

and subsequently d) acylating one or more resulting amines of formula (VIIb)

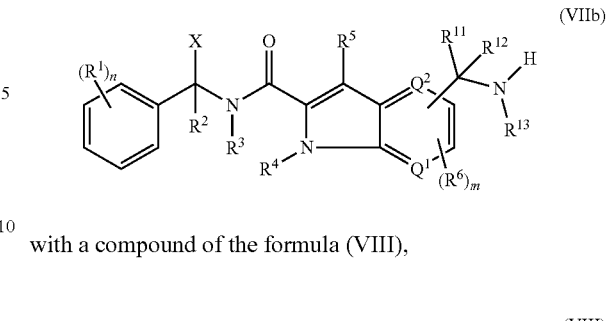
(VIIb)

with a compound of the formula (VIII),

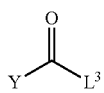
(VIII)

where L³ represents hydroxy, halogen or YC(O)O—.

4. A process for producing a pesticide comprises mixing one or more compounds of formula (I) and/or salt and/or N-oxide thereof according to claim 1 with one or more extenders and/or surfactants.

5. A compound of formula (I) and/or salt and/or N-oxide thereof according to claim 1 capable of being used for producing a pesticide.

6. Pesticide comprising one or more compounds of formula (I) and/or a salt and/or an N-oxide thereof according to claim 1 in a biologically effective amount of from 0.00000001 to 95% by weight, based on the weight of the pesticide.

7. Pesticide according to claim 6, additionally comprising a further active agrochemical ingredient.

8. A method for controlling one or more animal pests comprises allowing one or more compounds of formula (I) and/or salt and/or N-oxide thereof according to claim 1 to act on one or more animal pests and/or a habitat thereof, excluding methods for treatment of the human or animal body.

9. The process according to claim 2, wherein L² represents a leaving group comprising chlorine, bromine, or iodine.

10. The process according to claim 3, wherein L² represents a leaving group comprising chlorine, bromine, or iodine.

11. The compound of claim 1, wherein R³ is hydrogen.

12. The compound of claim 1, wherein R³ is methyl.

13. The compound of claim 1, wherein R⁵ is hydrogen.

14. The compound of claim 1, wherein R⁵ is bromine.

15. The compound of claim 1, wherein m is 0.

16. The compound of claim 1, wherein m is 1.

17. The compound of claim 1, wherein A is —C(=O)NR¹³—.

18. The compound of claim 1, wherein A is —CH₂—NH—C(=O)—.

* * * * *